US012747265B2

(12) United States Patent
Yamashita et al.

(10) Patent No.: US 12,747,265 B2
(45) Date of Patent: Sep. 29, 2026

(54) FOXM1-DERIVED PEPTIDE, AND VACCINE INCLUDING SAME

(71) Applicant: OncoTherapy Science, Inc., Kawasaki (JP)

(72) Inventors: Sachiko Yamashita, Kawasaki (JP); Tetsuro Hikichi, Kawasaki (JP)

(73) Assignee: OncoTherapy Science, Inc., Kawasaki (JP)

( * ) Notice: Subject to any disclaimer, the term of this patent is extended or adjusted under 35 U.S.C. 154(b) by 1244 days.

(21) Appl. No.: 17/559,991

(22) Filed: Dec. 22, 2021

(65) Prior Publication Data

US 2022/0112241 A1 Apr. 14, 2022

Related U.S. Application Data

(63) Continuation of application No. 15/762,436, filed as application No. PCT/JP2016/079717 on Oct. 6, 2016, now Pat. No. 11,242,365.

(30) Foreign Application Priority Data

Oct. 8, 2015 (JP) ................................ 2015-200221

(51) Int. Cl.

| | |
|---|---|
| ***C07K 7/06*** | (2006.01) |
| ***A61K 35/12*** | (2015.01) |
| ***A61K 35/15*** | (2025.01) |
| ***A61K 35/17*** | (2025.01) |
| ***A61K 38/00*** | (2006.01) |
| ***A61K 39/00*** | (2006.01) |
| ***C07K 14/47*** | (2006.01) |
| ***C07K 16/30*** | (2006.01) |
| ***C07K 16/32*** | (2006.01) |
| ***C12N 5/0783*** | (2010.01) |
| ***C12N 5/0784*** | (2010.01) |
| ***C12N 5/10*** | (2006.01) |
| ***G01N 33/50*** | (2006.01) |

(52) U.S. Cl.

CPC ................ *C07K 7/06* (2013.01); *A61K 35/12* (2013.01); *A61K 35/15* (2013.01); *A61K 35/17* (2013.01); *A61K 38/00* (2013.01); *A61K 39/0011* (2013.01); *C07K 14/4705* (2013.01); *C07K 16/30* (2013.01); *C07K 16/32* (2013.01); *C12N 5/0638* (2013.01); *C12N 5/0639* (2013.01); *C12N 5/10* (2013.01); *G01N 33/5047* (2013.01); *G01N 33/505* (2013.01); *A61K 39/00* (2013.01); *A61K 2039/5154* (2013.01)

(58) Field of Classification Search

CPC .... A61K 39/0011; A61K 38/00; A61K 35/17; C07K 7/06; C12N 5/0638

See application file for complete search history.

(56) References Cited

U.S. PATENT DOCUMENTS

| | | | |
|---|---|---|---|
| 5,861,278 | A | 1/1999 | Wong et al. |
| 8,569,244 | B2 | 10/2013 | Nishimura et al. |
| 9,056,890 | B2 | 6/2015 | Nakamura et al. |
| 2004/0063907 | A1 | 4/2004 | Zauderer et al. |
| 2005/0260639 | A1 | 11/2005 | Nakamura et al. |
| 2006/0014686 | A1 | 1/2006 | Wonsey et al. |
| 2006/0024692 | A1 | 2/2006 | Nakamura et al. |
| 2007/0083334 | A1 | 4/2007 | Mintz et al. |
| 2007/0269432 | A1 | 11/2007 | Nakamura et al. |
| 2008/0050378 | A1 | 2/2008 | Nakamura et al. |
| 2009/0047306 | A1 | 2/2009 | Nash et al. |
| 2009/0162361 | A1 | 6/2009 | Nakamura et al. |
| 2009/0175844 | A1 | 7/2009 | Nakamura et al. |
| 2009/0208514 | A1 | 8/2009 | Nakamura et al. |
| 2009/0286856 | A1 | 11/2009 | Nakamura et al. |
| 2009/0317392 | A1 | 12/2009 | Nakamura et al. |
| 2010/0173317 | A1 | 7/2010 | Nakamura et al. |
| 2011/0195081 | A1 | 8/2011 | Nakamura et al. |
| 2011/0223687 | A1 | 9/2011 | Nakamura et al. |
| 2012/0010090 | A1 | 1/2012 | Nakamura et al. |

(Continued)

FOREIGN PATENT DOCUMENTS

| | | |
|---|---|---|
| CN | 101835792 | 9/2010 |
| CN | 102405285 | 4/2012 |

(Continued)

OTHER PUBLICATIONS

Van Elsas et al, European Journal of Immunology, 1996, vol. 26, pp. 1683-1689 (Year: 1996).*

(Continued)

*Primary Examiner* — Karen A. Canella

(74) *Attorney, Agent, or Firm* — Kilpatrick Townsend & Stockton LLP

(57) ABSTRACT

The present invention provides FOXM1-derived epitope peptides having the ability to induce cytotoxic T cells. The present invention further provides polynucleotides encoding the peptides, antigen-presenting cells presenting the peptides, and cytotoxic T cells targeting the peptides, as well as methods of inducing the antigen-presenting cells or CTLs. The present invention also provides compositions and pharmaceutical compositions containing them as an active ingredient. Further, the present invention provides methods of treating and/or preventing cancer, and/or preventing post-operative recurrence thereof, using the peptides, polynucleotides, antigen-presenting cells, cytotoxic T cells or pharmaceutical compositions of the present invention. Methods of inducing an immune response against cancer are also provided.

10 Claims, 10 Drawing Sheets

Specification includes a Sequence Listing.

(56) References Cited

U.S. PATENT DOCUMENTS

| | | | |
|---|---|---|---|
| 2012/0014996 A1 | 1/2012 | Nakamura et al. |
| 2012/0021946 A1 | 1/2012 | Nakamura et al. |
| 2012/0156231 A1 | 6/2012 | Tsunoda et al. |
| 2013/0011933 A1 | 1/2013 | Nakamura et al. |
| 2014/0023672 A1 | 1/2014 | Nishimura et al. |
| 2015/0224182 A1 | 8/2015 | Hunt et al. |
| 2015/0265689 A1 | 9/2015 | Nishimura et al. |

FOREIGN PATENT DOCUMENTS

| | | | |
|---|---|---|---|
| CN | 105837678 | 8/2016 | |
| EP | 0846761 | 6/1998 | |
| EP | 1806413 | 7/2007 | |
| EP | 2189471 | 5/2010 | |
| JP | 2012-517799 | 8/2012 | |
| RU | 2487886 | 7/2013 | |
| TW | 200922616 | 6/2009 | |
| TW | 201032821 | 9/2010 | |
| WO | 2002099076 | 12/2002 | |
| WO | 2004019761 | 3/2004 | |
| WO | 2004031412 | 4/2004 | |
| WO | 2004031413 | 4/2004 | |
| WO | 2004100977 | 11/2004 | |
| WO | 2005028676 | 3/2005 | |
| WO | 2005090603 | 9/2005 | |
| WO | 2006085684 | 8/2006 | |
| WO | 2007013665 | 2/2007 | |
| WO | 2007013671 | 2/2007 | |
| WO | 2009022652 | 2/2009 | |
| WO | 2009025196 | 2/2009 | |
| WO | 2010095428 | 8/2010 | |
| WO | WO-2011149909 A2 * | 12/2011 | ....... G01N 33/57492 |
| WO | 2014036562 | 3/2014 | |
| WO | 2015/034519 A1 | 3/2015 | |
| WO | 2016172722 | 10/2016 | |

OTHER PUBLICATIONS

U.S. Appl. No. 15/762,436 , Final Office Action, Mailed On Jul. 22, 2021, 14 pages.
U.S. Appl. No. 15/762,436 , Non-Final Office Action, Mailed On Dec. 23, 2020, 22 pages.
U.S. Appl. No. 15/762,436 , Non-Final Office Action, Mailed On Oct. 28, 2021, 7 pages.
U.S. Appl. No. 15/762,436 , Notice of Allowance, Mailed On Nov. 17, 2021, 10 pages.
Adams, et al.; Prediction of binding to MHC class I molecules; J. Immunol. Methods; Sep. 25, 1995; 185(2):181-90.
Bae et al., “Heteroclitic CD33 Peptide With Enhanced Anti-Acute Myeloid Leukemic Immunogenicity”, Clinical Cancer Research, vol. 10, Oct. 15, 2004, pp. 7043-7052.
Belli, et al; Vaccination of Metastatic Melanoma Patients with Autologous Tumor-Derived Heat Shock Protein; J. Clin. Oncology; Oct. 15, 2002; 20(20):4169-80.
Boon; Tumor Antigens Recognized by Cytolytic T Lymphocytes; Int. J. Cancer; May 8, 1993; 54(2):177-180.
Boon et al; Human Tumor Antigens Recognized by T Lymphocytes; J. Exp. Med.; Mar. 1, 1996; 183(3):725-9.
Butterfield, et al; Generation of Human T-cell Responses to an HLA-A2.1-restricted Peptide Epitope; Cancer Res.; Jul. 1, 1999; 59(13):3134-42.
Cao et al., “Analysis of the Frequencies of Hla-A, B, and C Alleles and Haplotypes in the Five Major Ethnic Groups of the United States Reveals High Levels of Diversity in These Loci and Contrasting Distribution Patterns in These Populations”, Human Immunology, vol. 62, 2001, pp. 1009-1030.
Coulie, et al; Cytolytic T-cell responses of cancer patients vaccinated with a MAGE antigen; Immunol. Rev.; Oct. 2002; 188:33-42.
Database GenBank Accession No. NM_2002002.
Dionne, et al; Functional characterization of CTL against gp100 altered peptide ligands; Cancer Immunol. Immunother.; Apr. 2003; 52(4):199-206; Epub Feb. 18, 2003.
Dionne, et al; Her-2/neu altered peptide ligand-induced CTL responses; Cancer Immunol. Immunother.; Apr. 2004; 53(4):307-14.
Engelhard; Structure of peptides associated with MHC Class I molecules; Current Opinion in Immumology; Feb. 1994; 6(1):13-23.
Ezzell; Cancer “Vaccines”: An Idea Whose Time Has Come?; J. NIH Res.; 1995; 7:46.
Falk et al., “Peptide Motifs of HLA-A1, -A11, -A31, and -A33 Molecules”, Immunogenetics, vol. 40, No. 3, 1994, pp. 238-241.
Falk, et al; Allele-specific motifs revealed by sequencing of self-peptides eluted from MHC molecules; Nature; May 23, 1991; 351(6324):290-6.
Fujie, et al; A MAGE-1-Encoded HLA-A24-Binding Synthetic Peptide Induces Specific Anti-Tumor Cytotoxic T Lymphocytes; Int. J. Cancer; Jan. 18, 1999; 80(2):169-72.
Gambacorti-Passerini et al., “Mapping of HLA Class I Binding Motifs in Forty-Four Fusion Proteins Involved in Human Cancers”, Clinical Cancer Research, vol. 3, No. 5, May 1997, pp. 675-683.
Gusarova, et al; A cell-penetrating AFR peptide inhibitor of FoxM1 in mouse hepatocellular carcinoma treatment; J. Clin. Invest.; Jan. 2007; 117(1):99-111. Epub Dec. 14, 2006.
Halasi et al., “Targeting FOXM1 in Cancer”, Biochemical Pharmacology, vol. 85, Mar. 1, 2013, pp. 644-652.
Harris; Structure and Function of the p53 Tumor Suppressor Gene; J. Natl. Cancer Inst .; Oct. 16, 1996; 88(20):1442-55.
Hartman et al., “Increasing Vaccine Potency Through Exosome Antigen Targeting”, Vaccine, vol. 29, 2011, pp. 9361-9367.
Hoffmann, et al; The Ability of Variant Peptides to Reverse the Nonresponsiveness of T Lymphocytes, etc.; J. Immunol; Feb.1, 2002; 168(3):1338-47.
Iseki et al., “Evaluation of a New Oil Adjuvant For Use In Peptide-Based Cancer Vaccination”, Cancer Science, vol. 101, No. 10, Oct. 2010, pp. 2110-2114.
Kalinichenko, et al; Foxm1b transcription factor is essential for development of hepatocellular carcinomas etc; Genes Dev. Apr. 1, 2004; 18(7):830-50.
Kikuchi, et al; Ident. of a SART-1-Derived Peptide Capable of Inducing HLA-A24-Restricted and Tumor-Specific Cytotoxic T Lymphocytes; Int. J. Cancer; May 5, 1999; 81(3):459-66.
Kim, et al; The Forkhead Box m1 Transcription Factor Stimulates the Proliferation of Tumor Cells etc.; J. Cancer Res.; Feb. 15, 2006; 15:66(4): 2153-61.
Kondo, et al; Prominent Roles of Secondary Anchor Residues in Peptide Binding to HLA-A24 Human Class I Molecules; J. Immunol.; Nov. 1, 1995; 155(9):4307-12.
Kubo et al., “Definition of Specific Peptide Motifs for Four Major HLA-A Alleles”, The Journal of Immunology, vol. 152, No. 8, Apr. 15, 1994, pp. 3913-3924.
Laoukili, et al; FoxM1: At the crossroads of ageing and cancer; Biochimica et Biophysica Acta; Jan. 2007; 1775(1):92-102; Epub Aug. 30, 2006.
Laoukili, et al; FoxM1 is required for execution of the mitotic programme and chromosome stability; Nat. Cell Biol.; Feb. 2005; 7(2): 126-36; Epub Jan. 16, 2005.
Marsh et al., “The HLA FactsBook”, Academic Press, 2000, 4 pages.
PCT/JP2016/079717 , “Partial European Supplementary Search Report”, Feb. 4, 2019, 15 pages.
European Patent Office, Supplementary Partial European Search Report of EP 16 85 3677, Jan. 18, 2019, 15 pgs.
Obama, et al; Genome-Wide Analysis of Gene Expression in Human Intrahepatic Cholangiocarcinoma; Hepatology; Jun. 2005; 41(6): 1339-48.
Oiso, et al; A Newly Identified MAGE-3-Derived Epitope Recognized by HLA-A24-Restricted Cytotoxic T Lymphocytes; Int. J. Cancer; May 5, 1999; 81(3):387-94.
Parker, et al; Scheme for Ranking Potential HLA-A2 Binding Peptides etc.; J. Immunol. Jan. 1, 1994; 152(1):163-75.
Priller, et al; Expression of FoxM1 is Required for the Proliferation of Medulloblastoma Cells, etc.; Clin. Cancer Res.; Nov. 1, 2011; 17(21): 6791-801; Epub Sep. 14, 2011.

(56) References Cited

OTHER PUBLICATIONS

Radhakrishnan, et al; Identification of a Chemical Inhibitor of the Oncogenic Transcription Factor Forkhead Box M1; Cancer Res.; Oct. 2006; 1:66(19): 9731-35.
Rammensee, et al; MHC ligands and peptide motifs: first listing; Immunogenetics; 1995; 41(4):178-228.
Roitt , "Antigen Recognition", Immunology, 2000, 4 pages.
Rosenberg et al., "Cancer Immunotherapy: Moving Beyond Current Vaccines", Nature Medicine, vol. 10, No. 9, Sep. 2004, 7 pages.
Schijns et al., "Trends in Vaccine Adjuvants", Expert Review of Vaccines, vol. 10, Issue 4, 2011, pp. 539-550.
Schueler-Furman, et al;Structure-based prediction of binding peptides to MHC class I molecules, etc.; Protein Sci.; Sep. 2000; 9(9):1838-46.
Shastri, et al.; Presentation of Endogenous Peptide/MHC Class I Complexes is Profoundly Influenced etc.; J. Immunol.; Nov. 1, 1995; 155(9):4339-46.
Sugiura, et al; Treatment Outcome of Peptide Vaccination for Advanced Colorectal Cancer; Gan To Kagaku Ryoho; Nov. 2013; 40(12): 1584-86.
Takiguchi et al., "Analysis of Three HLA-A*3303 Binding Peptide Anchors Using an HLA-A*3303 Stabilization Assay", Tissue Antigens, vol. 55, No. 4, Apr. 2000, pp. 296-302.
Takiguchi et al., "Polarity of the P1 Anchor Residue Determines Peptide Binding Specificity Between HLA-A*3101 and HLA-A*3303", Tissue Antigens, vol. 56, No. 6, Dec. 2000, pp. 501-506.
Tanaka, et al; Induction of Antitumor Cytotoxic T Lymphocytes with a MAGE-3-encoded Synthetic Peptide, etc.; Cancer Res.; Oct. 15, 1997; 57(20):4465-68.
Van Der Burg, et al; Immunogenicity of Peptides Bound to MHC Class I Molecules etc.; J. Immunol.; May 1, 1996; 156(9):3308-14.
Vissers, et al; The Renal Cell Carcinoma-associated Antigen G250 Encodes a Human Leukocyte Antigen-A2.1-restricted Epitope, etc.; Cancer Res.; Nov. 1, 1999; 59(21):5554-59.
Wang, et al; The Forkhead Box m1b transcription factor is essential for hepatocyte DNA replication, etc.; PNAS; Dec. 24, 2002; 99(26):16881-86; Epub Dec. 13, 2002.
Williams et al., "Drug Development and Industrial Pharmacy", 1998, vol. 24, Previously presented. 157-162.
Wonsey, et al; Loss of the Forkhead Transcription Factor FoxM1 Causes Centrosome Amplification, etc.; Cancer Res.; Jun. 15, 2005; 65(12):5181-89.
Yokomine et al., "The Forkhead Box M1 Transcription Factor as a Candidate of Target for Anti-Cancer Immunotherapy", International Journal of Cancer, vol. 126, 2010, pp. 2153-2163.
Yokomine, et al; FOXM1, a novel cancer-associated antigen useful for immunotherapy, etc.; Abst. of 66th Annual Meeting of JP Cancer Assn.; 2007: 164(#p. 295).
Yoshida, et al; The Forkhead Box M1 Transcription Factor Contributes to the Development, etc.; Gastroenterology; Apr. 2007; 132(4):1420-31; Epub Jan. 25, 2007.
Zaremba, et al; Identification of an Enhancer Agonist Cytotoxic T Lymphocyte Peptide from Human Carcinoembryonic Antigen; Cancer Res.; Oct. 15, 1997; 57(20):4570-77.
ISA—Japan Patent Office; International Search Report; PCT/JP2016/079717; date of mailing Dec. 20, 2016.
English language translation of CN 105837678 A (Zang Xin) (Year: 2021).
Marsh et al., The HLA FactsBook; Academic Press, 2000, 4 pages (see pp. 100, 138).
Roitt, et al., Antigen Recognition; Immunology, translation from English-Mowcow: Mir, 2000, Fifth Edition; pp. 159,161-3.
Rosenberg, et al.; Cancer immunotherapy: moving beyond current vaccines; Nature Medicine, vol. 10, No. 9, Sep. 2004; pp. 909-915.
Database GenBank Accession No. NM_202002, Nov. 13, 2006.

* cited by examiner

FOXM1-DERIVED PEPTIDE, AND VACCINE INCLUDING SAME

CROSS-REFERENCE TO RELATED APPLICATIONS

The present application is a divisional of U.S. application Ser. No. 15/762,436, filed Mar. 22, 2018, which is a § 371 National Phase Application of PCT/JP2016/079717, filed Oct. 6, 2016, which application claims the benefit of Japanese Patent Application No. JP 2015-200221, filed on Oct. 8, 2015, the entire contents of which are incorporated by reference in their entireties for all purposes herein.

TECHNICAL FIELD

The present invention relates to the field of biological science, more specifically to the field of cancer therapy. In particular, the present invention relates to novel peptides that are effective as cancer vaccines, methods for either or both of treating and preventing tumors using the peptide(s), and pharmaceutical compositions comprising the peptide(s).

BACKGROUND ART

CD8-positive cytotoxic T lymphocytes (CTLs) have been known to recognize epitope peptides derived from the tumor-associated antigens (TAAs) presented on the major histocompatibility complex (MHC) class I molecule expressed on cell surface, and then kill the tumor cells. Since the discovery of the melanoma antigen (MAGE) family, many TAAs have been discovered through immunological approaches (NPL1: Boon T, Int J Cancer 1993, 54(2): 177-80; NPL2: Boon T & van der Bruggen P, J Exp Med 1996, 183(3): 725-9). Some of these TAAs are currently undergoing clinical development as immunotherapeutic targets.

In several of these TAAs, epitope peptides that can be recognized by CTLs are identified and their application in immunotherapy for various types of cancer is anticipated (NPL3: Harris C C, J Natl Cancer Inst 1996, 88(20): 1442-55; NPL4: Butterfield L H et al., Cancer Res 1999, 59(13): 3134-42; NPL5: Vissers J L et al., Cancer Res 1999, 59(21): 5554-9; NPL6: van der Burg S H et al., J Immunol 1996, 156(9): 3308-14; NPL7: Tanaka F et al., Cancer Res 1997, 57(20): 4465-8; NPL8: Fujie T et al., Int J Cancer 1999, 80(2): 169-72; NPL9: Kikuchi M et al., Int J Cancer 1999, 81(3): 459-66; NPL10: Oiso M et al., Int J Cancer 1999, 81(3): 387-94). Until now, several clinical trials using these TAA-derived epitope peptides have been reported. However, unfortunately, the response rate is not high in many clinical trials (NPL11: Belli F et al., J Clin Oncol 2002, 20(20): 4169-80; NPL12: Coulie P G et al., Immunol Rev 2002, 188: 33-42; NPL13: Rosenberg S A et al., Nat Med 2004, 10(9): 909-15). Therefore, there is still demand for identification of novel CTL epitope peptides that can be applied to cancer immunotherapy.

FOXM1 (GenBank accession Number: NM_202003; Forkhead box M1) is identified and reported as a gene whose expression is upregulated in intrahepatic cholangiocarcinoma, non-small cell lung cancer and esophageal cancer tissues from the result of genome wide gene expression profile by a cDNA microarray targeting 27,648 genes (NPL14: Obama K et al., Hepatology 2005, 41(6): 1339-48; NPL15: Yokomine K et al., Int J Cancer 2010, 126(9): 2153-63; PTL1: WO2005/090603). On the other hand, FOXM1 expression level in normal tissue is very low compared to these cancer tissues. Furthermore, when FOXM1 expression was inhibited, proliferation of medulloblastoma cells was suppressed (NPL16: Priller M et al., Clin Cancer Res 2011, 17(21): 6791-801), FOXM1 is suggested to be a gene involved in the regulation of cancer cell proliferation. More specifically, FOXM1 is a TAA for many cancers repeating proliferation and thus epitope peptides derived from FOXM1 are considered to be applicable to immunotherapy targeting cancer patients.

Recently, FOXM1-derived HLA-A02-restricted epitope peptides (PTL2: WO2009/025196) and HLA-A24-restricted epitope peptides (PTL3: WO2010/095428) have been identified. Therapeutic effects by these peptides can be expected in cancer patients having the HLA-A02 type or HLA-A24 type, but cannot be expected on other cancer patients.

CITATION LIST

Patent Literature

[PTL 1] WO2005/090603

[PTL 2] WO2009/025196

[PTL 3] WO2010/095428

Non Patent Literature

[NPL 1] Boon T, Int J Cancer 1993, 54(2): 177-80

[NPL 2] Boon T & van der Bruggen P, J Exp Med 1996, 183(3): 725-9

[NPL 3] Harris C C, J Natl Cancer Inst 1996, 88(20): 1442-55

[NPL 4] Butterfield L H et al., Cancer Res 1999, 59(13): 3134-42

[NPL 5] Vissers J L et al., Cancer Res 1999, 59(21): 5554-9

[NPL 6] van der Burg S H et al., J Immunol 1996, 156(9): 3308-14

[NPL 7] Tanaka F et al., Cancer Res 1997, 57(20): 4465-8

[NPL 8] Fujie T et al., Int J Cancer 1999, 80(2): 169-72

[NPL 9] Kikuchi M et al., Int J Cancer 1999, 81(3): 459-66

[NPL 10] Oiso M et al., Int J Cancer 1999, 81(3): 387-94

[NPL 11] Belli F et al., J Clin Oncol 2002, 20(20): 4169-80

[NPL 12] Coulie P G et al., Immunol Rev 2002, 188: 33-42

[NPL 13] Rosenberg S A et al., Nat Med 2004, 10(9): 909-15

[NPL 14] Obama K et al., Hepatology 2005, 41(6): 1339-48

[NPL 15] Yokomine K et al., Int J Cancer 2010, 126(9): 2153-63

[NPL 16] Priller M et al., Clin Cancer Res 2011, 17(21): 6791-801

SUMMARY OF THE INVENTION

The present invention relates to peptides that can induce CTLs that specifically react to FOXM1-expressing cells. When these peptides form complex with the human leukocyte antigen (HLA) and are presented to CD8-positive T cells by antigen-presenting cells (APCs) which presents on their surface the complex, CTLs that show a peptide-specific cytotoxic activity are induced. FOXM1-derived peptides that have been identified so far to have CTL-inducing ability (CTL inducibility) are HLA-A02-restricted peptides and HLA-A24-restricted peptides, and cannot induce CTLs when antigen-presenting cells do not express these HLAs. Therefore, conventional peptides are not suitable for performing immunotherapy in subjects that do not have these HLAs. HLA-A33 is an allele commonly seen in Asians, and HLA-A01 is an HLA allele commonly seen in Caucasians (Cao K, et al., Hum Immunol 2001, 62(9): 1009-30). It is desirable to administer HLA-A33-restricted peptides to HLA-A33-positive subjects and HLA-A01-restricted peptides to HLA-A01-positive subjects. Hence, the present invention relates to FOXM1-derived peptides with CTL-inducing ability that are restrictive to HLA-A33 or HLA-A01. Based on results disclosed herein, the peptides of the present invention have been proven to be epitope peptides that can induce a potent and specific immune response against cancer cells expressing FOXM1 and HLA-A33 or HLA-A01.

Therefore, one of the objectives of the present invention is to provide FOXM1-derived peptides that can induce CTLs in an HLA-A33- or HLA-A01-restrictive manner. These peptides can be used to induce CTLs in vitro, ex vivo or in vivo, or can be used to administer to subjects for the purpose of inducing an immune response against FOXM1-expressing cancer cells. Preferable peptides are peptides comprising the amino acid sequence selected from among SEQ ID NOs: 1, 2, 3, 6, 7, 11, 12, 17, 18, 20, 22, 24, 26, 32, 33, 36, 39, 41, 42, 45, 46, 48, 49, 50, 52, 53, 55, 56, 57, 58, 59, 60, and 61; more preferable peptides are nonapeptides or decapeptides; and even more preferable peptides are peptides consisting of the amino acid sequence selected from among SEQ ID NOs: 1, 2, 3, 6, 7, 11, 12, 17, 18, 20, 22, 24, 26, 32, 33, 36, 39, 41, 42, 45, 46, 48, 49, 50, 52, 53, 55, 56, 57, 58, 59, 60, and 61.

The peptides of the present invention encompass peptides in which one, two or more amino acid(s) is/are substituted, deleted, inserted and/or added, as long as the resultant modified peptides retain the CTL-inducing ability of the original peptide.

The present invention further provides isolated polynucleotides encoding any one of the peptides of the present invention. Similar to the peptides of the present invention, these polynucleotides can be used for inducing APCs with CTL-inducing ability, and can be administered to subjects for inducing an immune response against FOXM1-expressing cancer cells.

The present invention also provides compositions comprising one or more types of peptides of the present invention, one or more types of polynucleotides encoding one or more types of peptides of the present invention, APCs of the present invention, exosomes presenting peptides of the present invention, and/or CTLs of the present invention. The compositions of the present invention are preferably pharmaceutical compositions. The pharmaceutical compositions of the present invention can be used for treating and/or preventing cancer, as well as preventing postoperative recurrence thereof. They can also be used for inducing an immune response against cancer. When administered to a subject, a peptide of the present invention is presented on the surface of an APC, and as a result CTLs targeting the peptide are induced. Therefore, another objective of the present invention is to provide compositions for inducing CTLs, wherein the compositions comprise one or more types of peptides of the present invention, one or more types of polynucleotides encoding one or more types of peptides of the present invention, APCs of the present invention, and/or exosomes presenting peptides of the present invention.

A further objective of the present invention is to provide methods of inducing APCs having CTL-inducing ability, wherein the methods comprise a step of contacting one or more types of peptides of the present invention with an APC, or a step of introducing a polynucleotide encoding any one peptide of the present invention into an APC.

The present invention further provides a method of inducing CTLs, comprising a step of co-culturing a CD8-positive T cell with an APC that presents on its surface a complex of an HLA antigen and a peptide of the present invention, a step of co-culturing a CD8-positive T cell with an exosome that presents on its surface a complex of an HLA antigen and a peptide of the present invention, or a step of introducing into a CD8-positive T cell a vector comprising a polynucleotide encoding each subunit of a T cell receptor (TCR) capable of binding to a peptide of the present invention presented by an HLA antigen on a cell surface. The preferred HLA antigen in the present invention is HLA-A33 or HLA-A01.

A further objective of the present invention is to provide isolated APCs that present on their surface a complex of an HLA antigen and a peptide of the present invention. The present invention further provides isolated CTLs targeting a peptide of the present invention. These APCs and CTLs can be used in immunotherapy for FOXM1-expressing cancers. In the present invention, the cancer to be subjected to immunotherapy is, for example, a cancer present in patients who have a homozygote or heterozygote of HLA-A33 or HLA-A01. Thus, the APCs or CTLs are also cells having a homozygote or heterozygote of HLA-A33 or HLA-A01. That is, the present invention provides immunotherapy for cancers expressing FOXM1 and at least one HLA antigen selected from HLA-A33 and HLA-A01.

Another objective of the present invention is to provide methods of inducing an immune response against cancer in a subject, wherein the methods comprise a step of administering to the subject a composition comprising a peptide(s) of the present invention or a polynucleotide(s) encoding the peptide(s), an APC(s) of the present invention, an exosome(s) presenting a peptide(s) of the present invention, and/or a CTL(s) of the present invention. Another objective of the present invention is to provide methods of treating and/or preventing cancer, as well as preventing postoperative recurrence thereof in a subject, wherein the methods comprise a step of administering to the subject a peptide(s) of the present invention, a polynucleotide(s) encoding the peptide(s), an APC(s) of the present invention, an exosome(s) presenting a peptide(s) of the present invention, and/or a CTL(s) of the present invention.

In addition to the above, other objects and features of the present invention will become more fully apparent when the following detailed description is read in conjunction with the accompanying figures and examples. However, it is to be understood that both the foregoing summary of the present invention and the following detailed description are of exemplified embodiments, and not restrictive of the present invention or other alternate embodiments of the present invention. In particular, while the present invention is described herein with reference to a number of specific embodiments, it will be appreciated that the description is illustrative of the present invention and is not constructed as limiting of the present invention. Various modifications and applications may occur to those who are skilled in the art, without departing from the spirit and the scope of the present invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

Cells that showed a reaction, boxed in the photos, were proliferated to establish a CTL line. Meanwhile, FOXM1-A33-10-288 (SEQ ID NO: 25) (v) is shown as an example of typical negative data in which peptide-specific IFN-gamma production was not observed.

Figure 1:
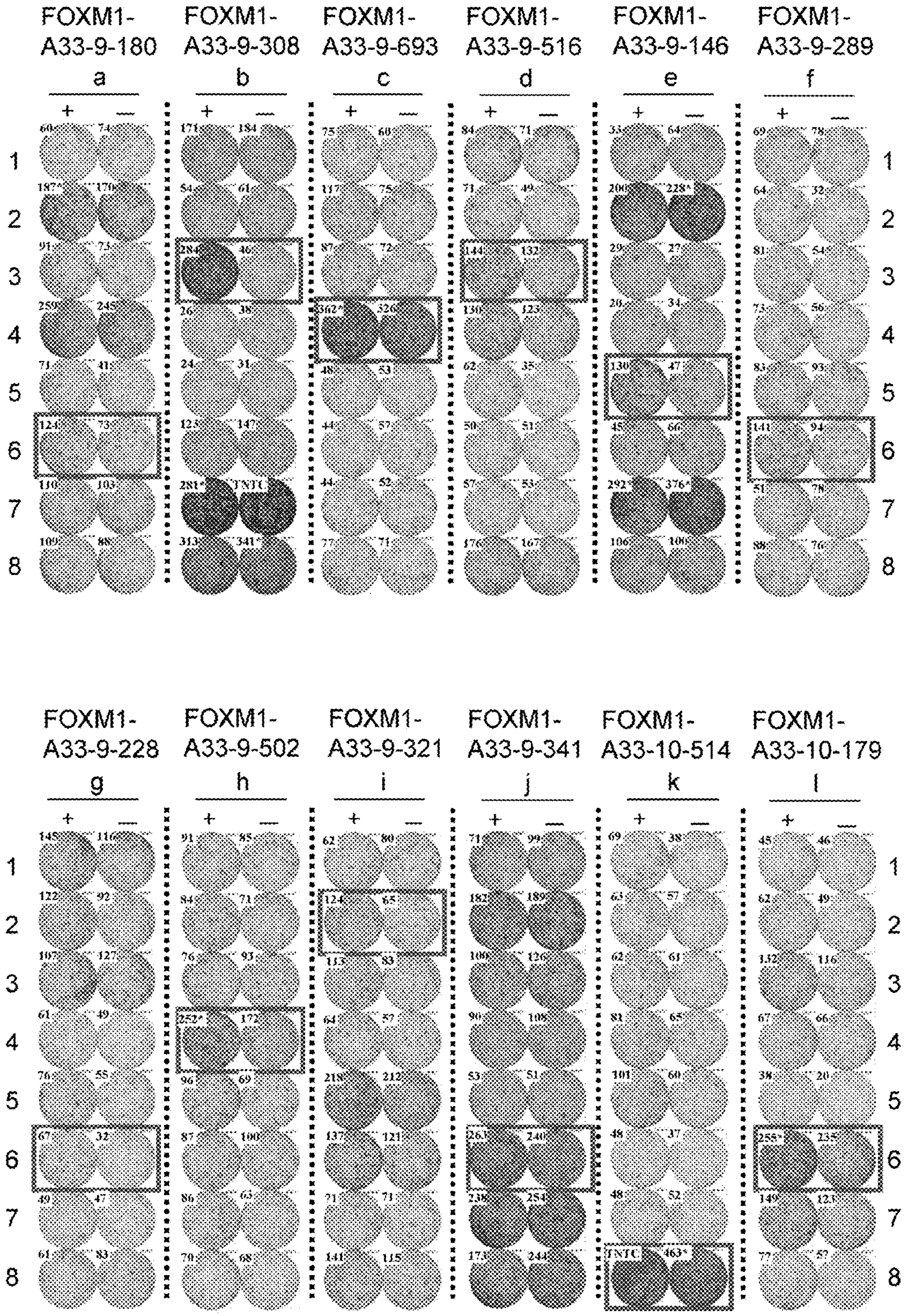
FIG. 1 consists of photos (a) to (v) showing results of an interferon (IFN)-gamma enzyme-linked immunospot (ELISPOT) assay performed using cells induced with peptides derived from FOXM1. In the figure, "+" shows IFN-gamma production against target cells pulsed with a peptide of interest; and "−" shows IFN-gamma production against target cells that have not been pulsed with any peptide (negative controls). It can be seen by comparison with the negative controls that peptide-specific IFN-gamma production was observed in Well #6 with FOXM1-A33-9-180 (SEQ ID NO: 1) (a),
Well #3 with FOXM1-A33-9-308 (SEQ ID NO: 2) (b),
Well #4 with FOXM1-A33-9-693 (SEQ ID NO: 3) (c),
Well #3 with FOXM1-A33-9-516 (SEQ ID NO: 6) (d),
Well #5 with FOXM1-A33-9-146 (SEQ ID NO: 7) (e),
Well #6 with FOXM1-A33-9-289 (SEQ ID NO: 11) (f),
Well #6 with FOXM1-A33-9-228 (SEQ ID NO: 12) (g),
Well #4 with FOXM1-A33-9-502 (SEQ ID NO: 17) (h),
Well #2 with FOXM1-A33-9-321 (SEQ ID NO: 18) (i),
Well #6 with FOXM1-A33-9-341 (SEQ ID NO: 20) (j).
Well #8 with FOXM1-A33-10-514 (SEQ ID NO: 22) (k),
Well #6 with FOXM1-A33-10-179 (SEQ ID NO: 24) (l),
Well #5 with FOXM1-A33-10-501 (SEQ ID NO: 26) (m),
Well #5 with FOXM1-A33-10-124 (SEQ ID NO: 32) (n),
Well #3 with FOXM1-A33-10-595 (SEQ ID NO: 33) (o),
Well #5 with FOXM1-A33-10-546 (SEQ ID NO: 36) (p),
Well #6 with FOXM1-A33-10-391 (SEQ ID NO: 39) (q),
Well #3 with FOXM1-A33-10-607 (SEQ ID NO: 41) (r),
Well #2 with FOXM1-A33-10-265 (SEQ ID NO: 42) (s),
Well #6 with FOXM1-A33-10-4 (SEQ ID NO: 45) (t) and
Well #5 with FOXM1-A33-10-388 (SEQ ID NO: 46) (u).
Figure 1:
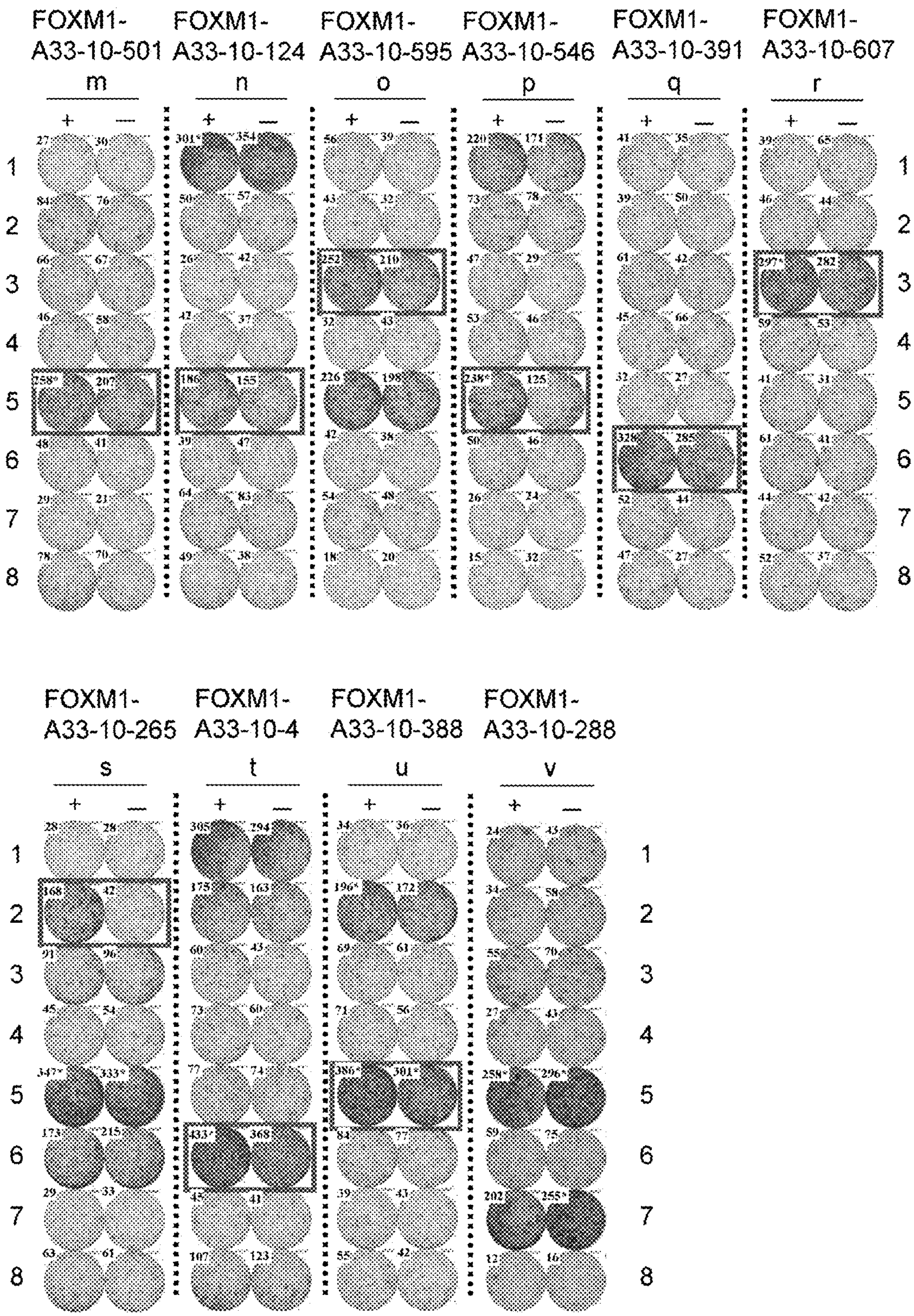

FIG. 1 (cont.) shows the continuation of FIG. 1.

Figure 2:
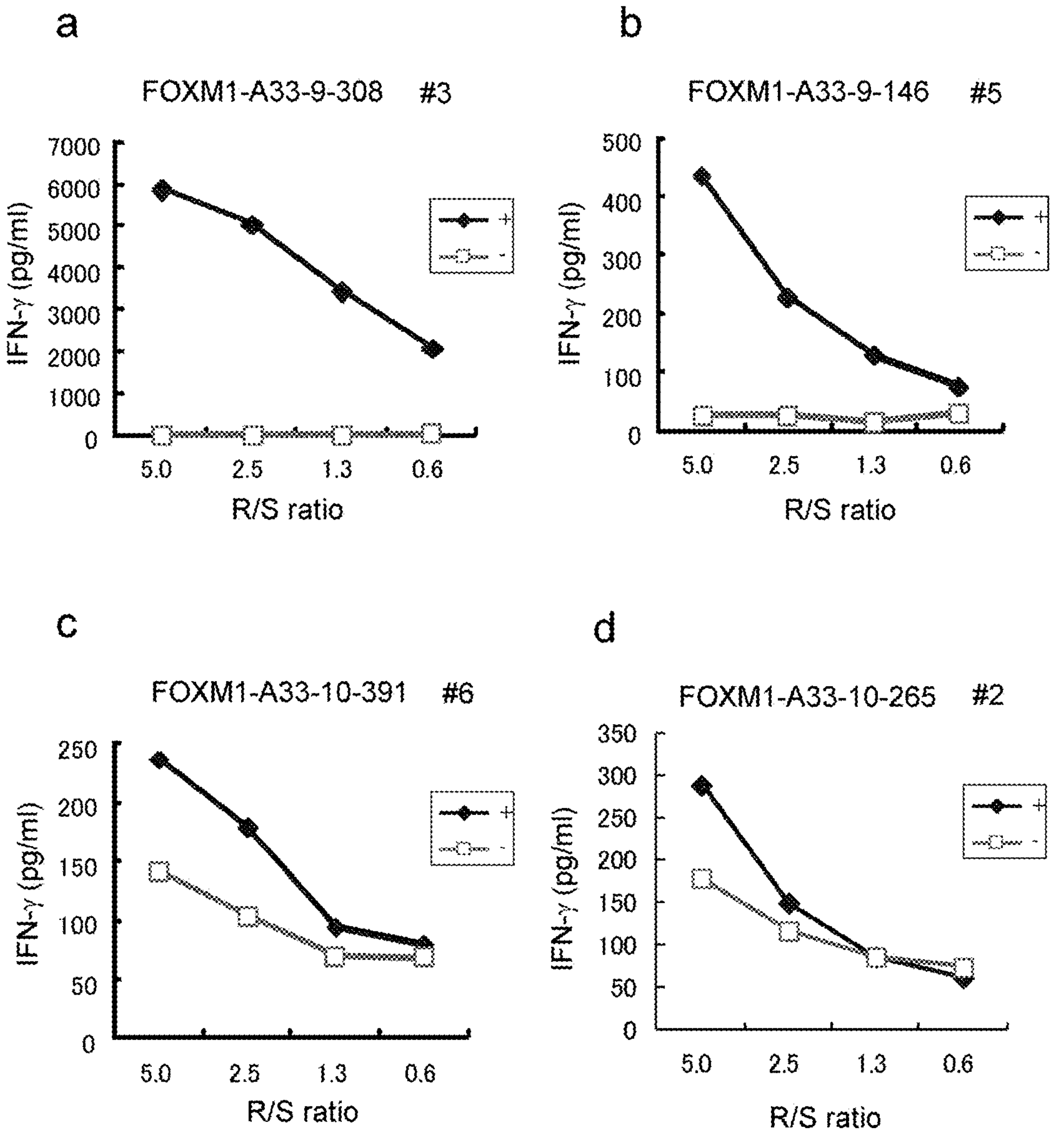

FIG. 2 consists of line graphs (a) to (d) showing results of measuring IFN-gamma produced by a CTL line stimulated with FOXM1-A33-9-308 (SEQ ID NO: 2) (a), FOXM1-A33-9-146 (SEQ ID NO: 7) (b), FOXM1-A33-10-391 (SEQ ID NO: 39) (c) or FOXM1-A33-10-265 (SEQ ID NO: 42) (d), using IFN-gamma enzyme-linked immunosorbent assay (ELISA). These results show that CTL lines that produce IFN-gamma in a peptide-specific manner were established after induction with each of the peptides. In the figure, "+" shows IFN-gamma production of the CTL line against target cells pulsed with a peptide of interest; and "−" shows IFN-gamma production of the CTL line against target cells that have not been pulsed with any peptide. The R/S ratio indicates the ratio of the cell number of CTL line (Responder cells) and the cell number of target cells that stimulate them (Stimulator cells).

Figure 3:
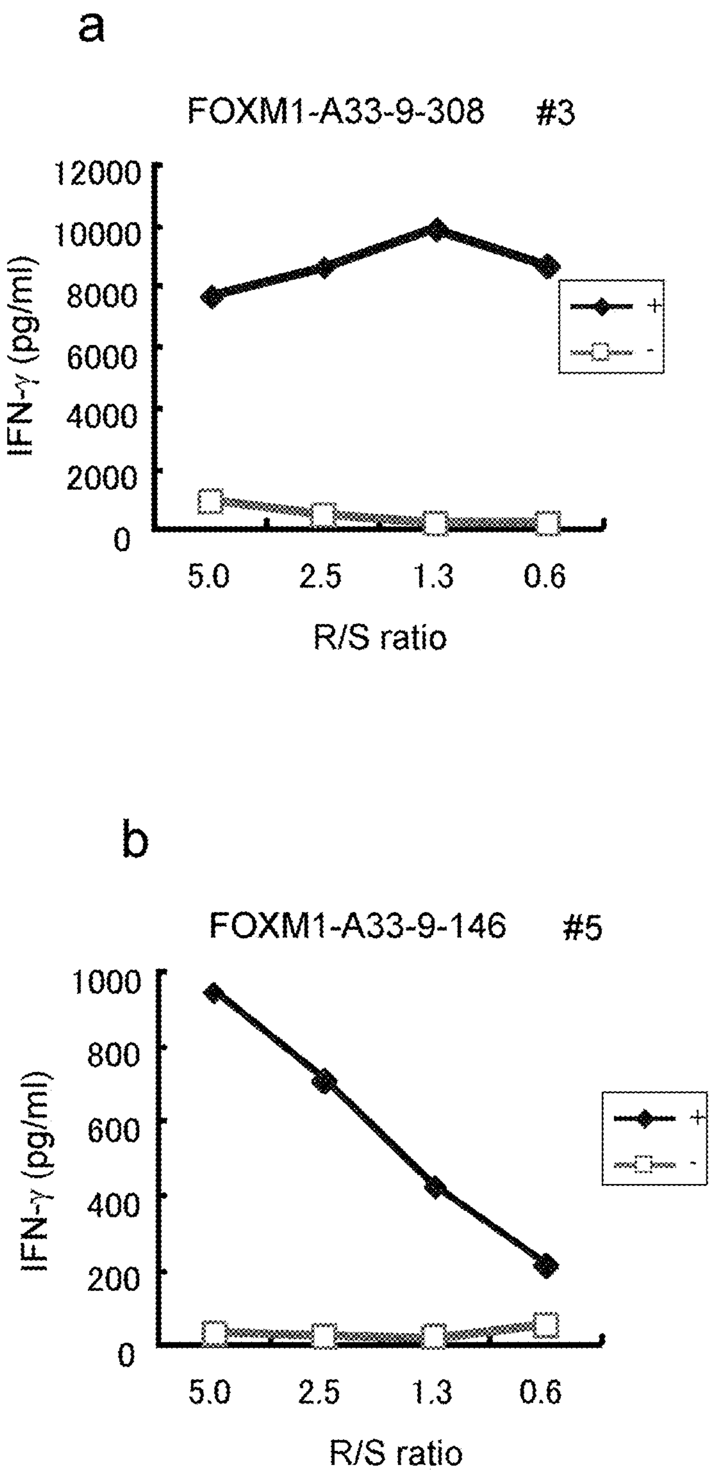

FIG. 3 consists of a series of line graphs (a) to (b) showing IFN-gamma production in a CTL clone established by the limiting dilution method following induction with FOXM1-A33-9-308 (SEQ ID NO: 2) (a) or FOXM1-A33-9-146 (SEQ ID NO: 7) (b). These results show the peptide-specific IFN-gamma production of the CTL clones. In the figure, "+" shows IFN-gamma production of the CTL clones against target cells pulsed with the peptide of interest; and "−" shows IFN-gamma production of the CTL clones against target cells that have not been pulsed with any peptide. The R/S ratio indicates the ratio of the cell number of CTL clone (Responder cells) and the cell number of target cells that stimulate them (Stimulator cells).

Figure 4:
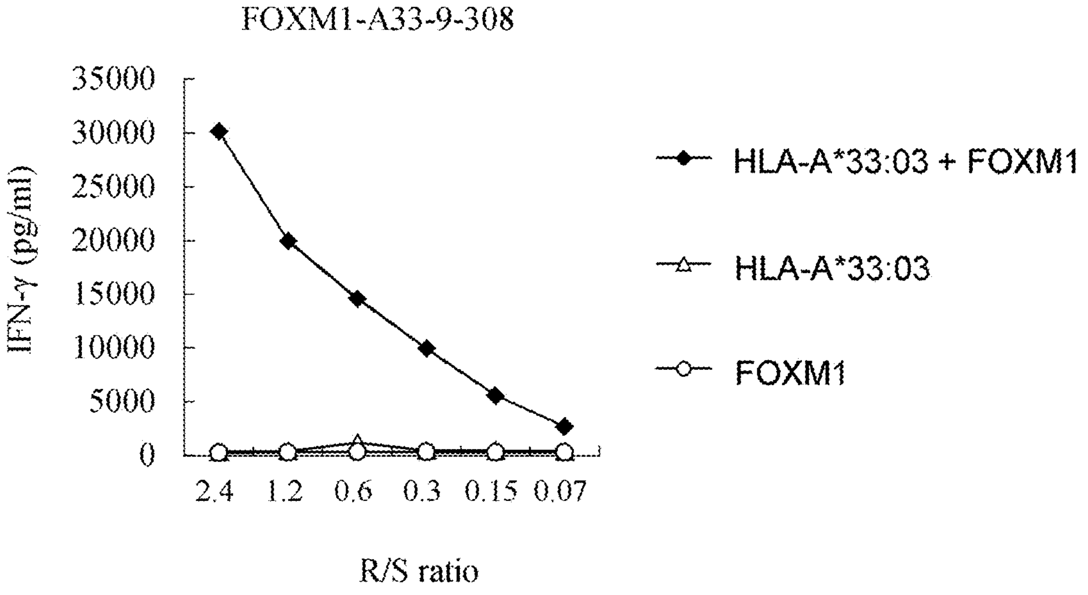

FIG. 4 is a line graph showing IFN-gamma production of CTL clones against target cells expressing both FOXM1 and HLA-A*33:03. Target cells introduced with either HLA-A*33:03 or the full-length FOXM1 gene were used as the negative control. The CTL clone established by induction using FOXM1-A33-9-308 (SEQ ID NO: 2) showed IFN-gamma production against COS7 cells introduced with both the FOXM1 and HLA-A*33:03 genes (black diamond). On the other hand, a significant IFN-gamma production was not shown against COS7 cells introduced with either one of HLA-A*33:03 (triangle) and FOXM1 (white circle).

Figure 5:
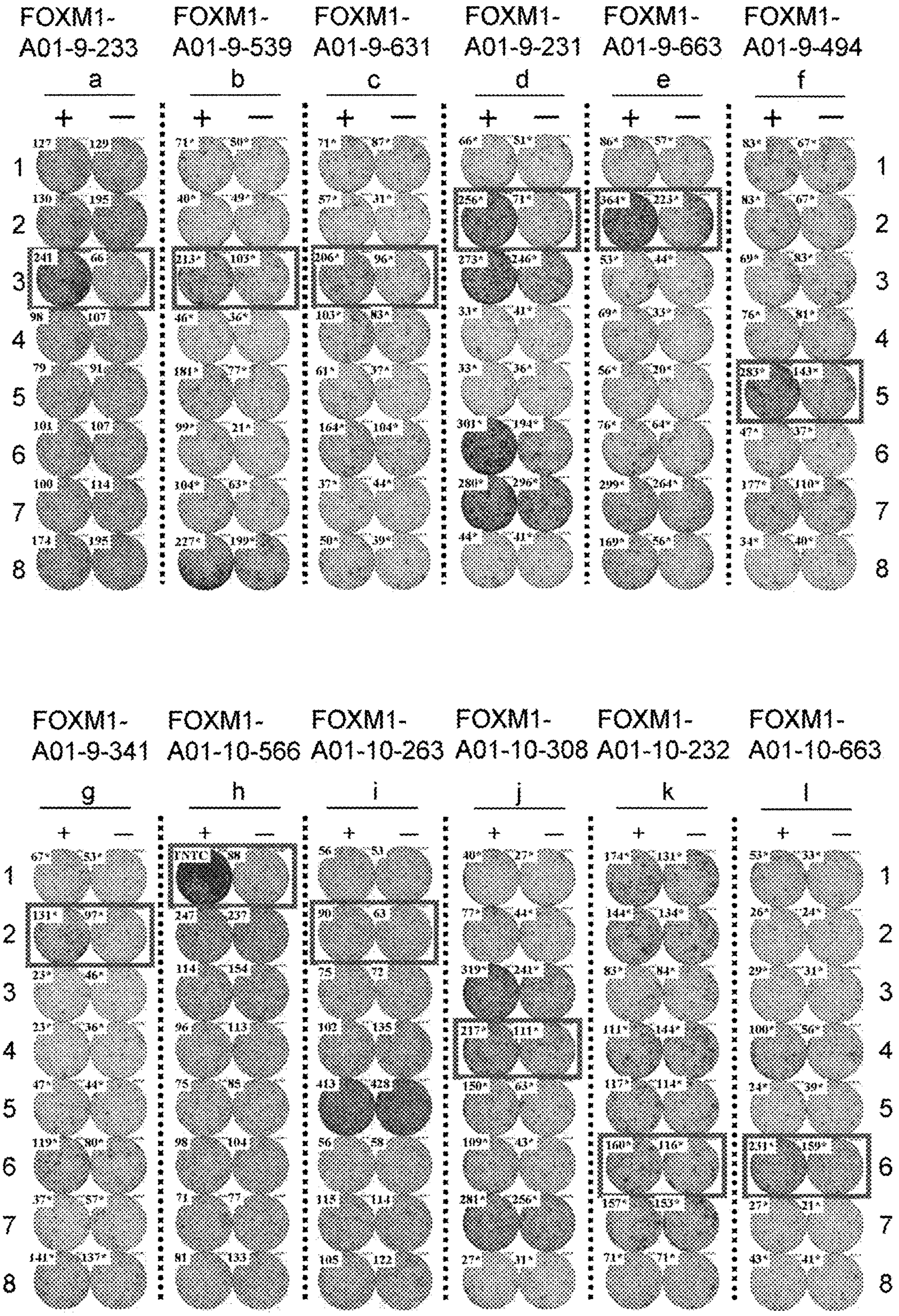
Figure 5:
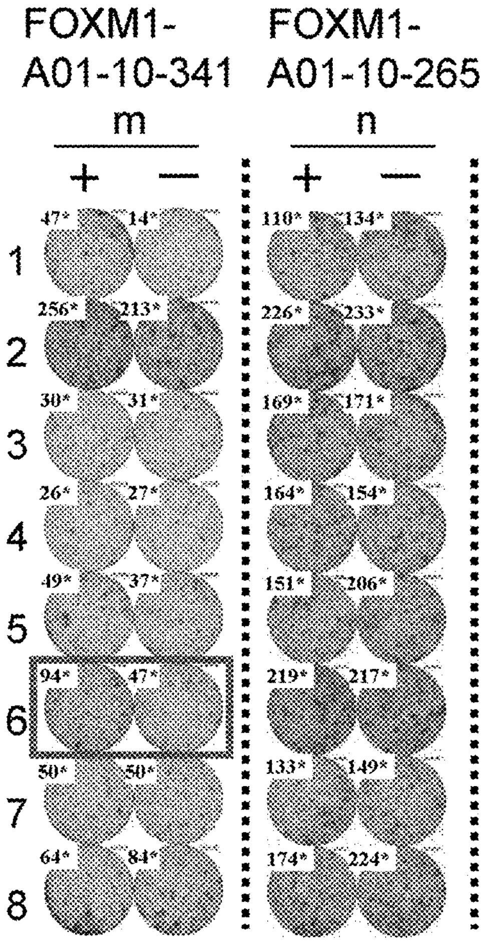

FIG. 5 consists of photos (a) to (n) showing results of an IFN-gamma enzyme-linked immunospot (ELISPOT) assay performed using cells induced with peptides derived from FOXM1. In the figure, "+" shows IFN-gamma production against target cells pulsed with the peptide of interest; and "−" shows IFN-gamma production against target cells that have not been pulsed with any peptide (negative controls). It can be seen by comparison with the negative controls that peptide-specific IFN-gamma production was observed in Well #3 with FOXM1-A01-9-233 (SEQ ID NO: 48) (a),
Well #3 with FOXM1-A01-9-539 (SEQ ID NO: 49) (b),
Well #3 with FOXM1-A01-9-631 (SEQ ID NO: 50) (c),
Well #2 with FOXM1-A01-9-231 (SEQ ID NO: 52) (d),
Well #2 with FOXM1-A01-9-663 (SEQ ID NO: 53) (e),
Well #5 with FOXM1-A01-9-494 (SEQ ID NO: 55) (f),
Well #2 with FOXM1-A01-9-341 (SEQ ID NO: 20) (g),
Well #1 with FOXM1-A01-10-566 (SEQ ID NO: 56) (h),
Well #2 with FOXM1-A01-10-263 (SEQ ID NO: 57) (i),
Well #4 with FOXM1-A01-10-308 (SEQ ID NO: 58) (j),
Well #6 with FOXM1-A01-10-232 (SEQ ID NO: 59) (k),
Well #6 with FOXM1-A01-10-663 (SEQ ID NO: 60) (l) and
Well #6 with FOXM1-A01-10-341 (SEQ ID NO: 61) (m).

Cells that showed a reaction, boxed in the photos, were proliferated to establish a CTL line. Meanwhile, FOXM1-A01-10-265 (SEQ ID NO: 42) (n) is shown as an example of typical negative data in which peptide-specific IFN-gamma production was not observed.

FIG. 5 (cont.) shows the continuation of FIG. 5.

Figure 6:
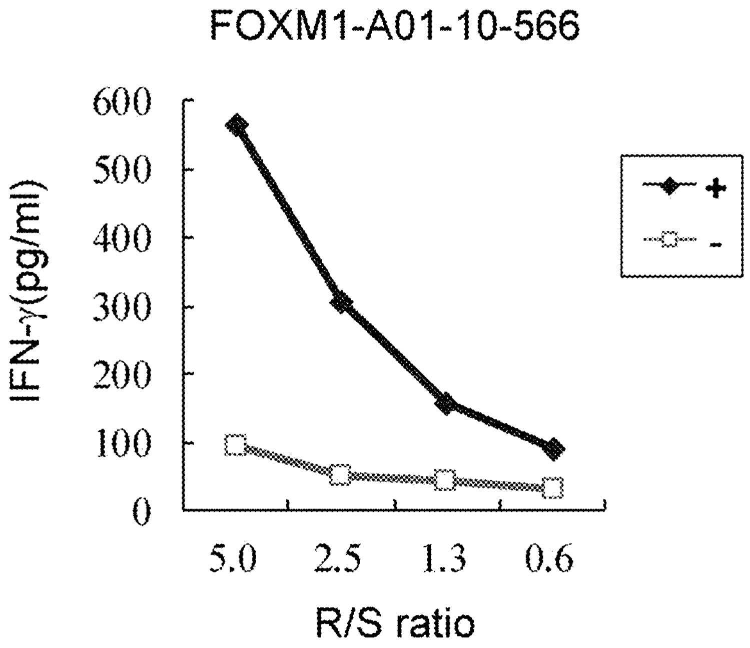

FIG. 6 is a line graph showing result of measuring, by ELISA, IFN-gamma produced by a CTL line stimulated with FOXM1-A01-10-566 (SEQ ID NO: 56). The result shows that CTL line that produce IFN-gamma in a peptide-specific manner was established after induction with the peptide. In the figure, "+" shows IFN-gamma production of the CTL line against target cells pulsed with a peptide of interest; and "−" shows IFN-gamma production of the CTL line against target cells that have not been pulsed with any peptide. The R/S ratio indicates the ratio of the cell number of CTL line (Responder cells) and the cell number of target cells that stimulate them (Stimulator cells).

Figure 7:
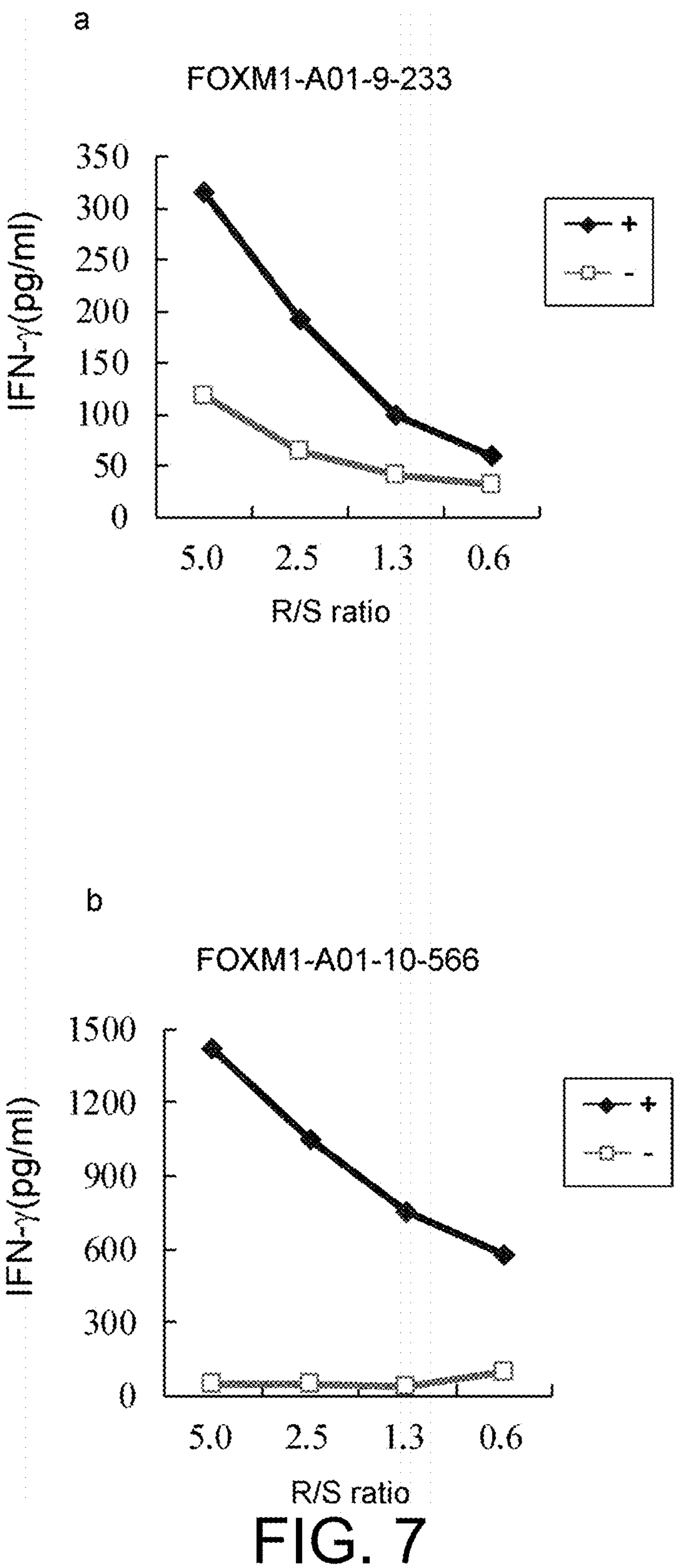

FIG. 7 consists of a series of line graphs (a) to (b) showing IFN-gamma production in a CTL clone established by the limiting dilution method following induction with FOXM1-A01-9-233 (SEQ ID NO: 48) or FOXM1-A01-10-566 (SEQ ID NO: 56). These results show the peptide-specific IFN-gamma production of the CTL clones. In the figure, "+" shows IFN-gamma production of the CTL clones against target cells pulsed with the peptide of interest; and "−" shows IFN-gamma production of the CTL clones against target cells that have not been pulsed with any peptide. The R/S ratio indicates the ratio of the cell number of CTL clone (Responder cells) and the cell number of target cells that stimulate them (Stimulator cells).

Figure 8:
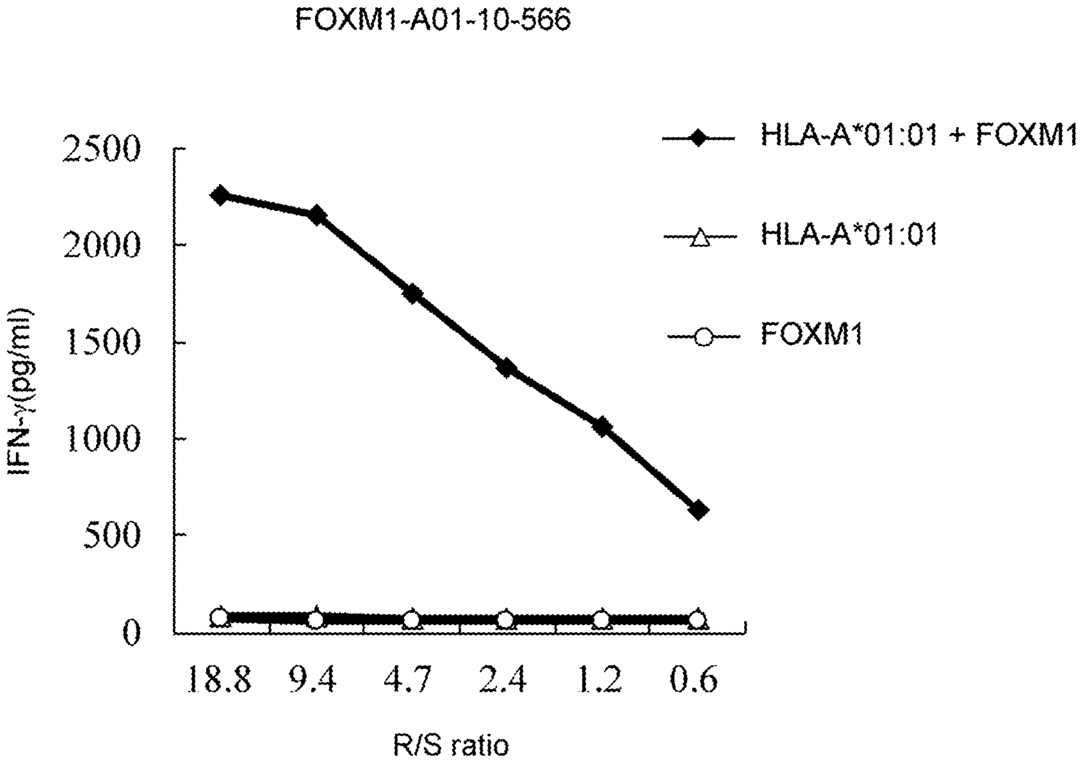

FIG. 8 is a line graph showing IFN-gamma production of CTL clones against target cells expressing both FOXM1 and HLA-A*01:01. Target cells introduced with either HLA-A*01:01 or FOXM1 gene were used as the negative control. The CTL clone established by induction using FOXM1-A01-10-566 (SEQ ID NO: 56) showed IFN-gamma production against COS7 cells introduced with both the FOXM1 and HLA-A*01:01 genes (black diamond). On the other hand, a significant IFN-gamma production was not shown against COS7 cells introduced with either one of HLA-A*01:01 (white triangle) and FOXM1 (white circle).

MODE FOR CARRYING OUT THE INVENTION

Description of Embodiments

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims.

I. Definitions

The words “a”, “an”, and “the” as used herein mean “at least one” unless otherwise specifically indicated.

The terms “isolated” and “purified” used in relation with a substance (for example, peptide, antibody, polynucleotide or such) indicate that the substance does not substantially contain at least one substance that may else be included in a natural source. Thus, an isolated or purified peptide refers to a peptide that does not substantially contain another cellular material, for example, carbohydrate, lipid and other contaminating proteins from the cell or tissue source from which the peptide is derived. When the peptide is chemically synthesized, an isolated or purified peptide refers to a peptide that does not substantially contain a precursor substance or another chemical substance. The phrase “does not substantially contain a cellular material” includes peptide preparations in which the peptide is separated from cellular components of the cells from which it is isolated or recombinantly produced. Thus, a peptide that does not substantially contain a cellular material encompasses peptide preparations that contain less than about 30%, 20%, 10%, or 5%, 3%, 2% or 1% (dry weight basis) of other cellular materials.

When the peptide is recombinantly produced, an isolated or purified peptide does not substantially contain culture medium, and a peptide which does not substantially contain culture medium encompasses peptide preparations that contain culture medium at less than about 20%, 10%, or 5%. 3%. 2% or 1% (dry weight basis) of the volume of the peptide preparation.

Alternatively, when the peptide is chemically synthesized, an isolated or purified peptide does not substantially contain a precursor substance or other chemical substances, and a peptide which does not substantially contain a precursor substance or other chemical substances encompasses peptide preparations that contain a precursor substance or other chemical substances at less than about 30%, 20%, 10%, 5%, 3%, 2% or 1% (dry weight basis) of the volume of the peptide preparation. That a particular peptide preparation is an isolated or purified peptide can be confirmed, for example, by the appearance of a single band following sodium dodecyl sulfate (SDS)-polyacrylamide gel electrophoresis and Coomassie Brilliant Blue staining or such of the gel. In a preferred embodiment, the peptides and polynucleotides of the present invention are isolated or purified.

The terms “polypeptide”, “peptide” and “protein” are used interchangeably herein, and refer to polymers of amino acid residues. These terms are applied to also non-naturally occurring amino acid polymers comprising one or more non-naturally occurring amino acid residues, in addition to naturally occurring amino acid polymers. Non-naturally occurring amino acids include amino acid analogs, amino acid mimetics, and such.

The term “amino acid” as used herein refers to naturally occurring amino acids, as well as amino acid analogs and amino acid mimetics that functions similarly to the naturally occurring amino acids. Naturally occurring amino acids are those encoded by the genetic code, as well as those modified after translation in cells (e.g., hydroxyproline, gamma-carboxyglutamate, and O-phosphoserine, etc.). The phrase “amino acid analog” refers to compounds that have the same basic chemical structure (an alpha carbon bound to a hydrogen, a carboxy group, an amino group, and an R group) as a naturally occurring amino acid but have a modified R group or modified backbones (e.g., homoserine, norleucine, methionine sulfoxide, methionine methyl sulfonium, and such). The phrase “amino acid mimetic” refers to compounds that have different structures from general amino acids but similar functions to amino acids. Amino acids can be either L-amino acids or D-amino acids, and the peptides of the present invention are preferably L-amino acid polymers.

The terms “polynucleotide”, “oligonucleotide”, and “nucleic acid” are used interchangeably herein, and refer to a polymer of nucleotides.

The term “composition” used in the present specification is intended to encompass products that include specified ingredients in specified amounts, and any products generated directly or indirectly from combination of specified ingredients in the specified amounts. When the composition is a pharmaceutical composition, the term “composition” is intended to encompass products including active ingredient(s) and inert ingredient(s), as well as any products generated directly or indirectly from combination, complexation or aggregation of any two or more ingredients, from dissociation of one or more ingredients, or from other types of reactions or interactions of one or more ingredients. Thus, the pharmaceutical compositions of the present invention encompass any compositions made by admixing compounds or cells of the present invention with a pharmaceutically or physiologically acceptable carrier. Without being limited thereto, the terms “pharmaceutically acceptable carrier” or “physiologically acceptable carrier” used in the present specification include liquid or solid bulking agents, diluents, excipients, solvents, and encapsulation materials; and mean pharmaceutically or physiologically acceptable materials, compositions, substances or media.

Unless otherwise specified, the term “cancer” refers to a cancer that overexpresses the FOXM1 gene; and examples thereof include acute myeloid leukemia (AML), bladder cancer, breast cancer, cervical cancer, cholangiocellular cancer, chronic myeloid leukemia (CML), colon cancer, esophageal cancer, gastric cancer, diffuse gastric cancer, liver cancer, non-small-cell lung cancer (NSCLC), lymphoma, osteosarcoma, ovary cancer, pancreatic cancer, prostate cancer, kidney cancer, small-cell lung cancer (SCLC), soft tissue tumor, testicular tumor and such, without being limited thereto. In an exemplary embodiment, the "cancer" is a cancer that expresses FOXM1 and HLA-A33 and/or HLA-A01.

Unless otherwise specified, the terms "cytotoxic T lymphocyte" and "cytotoxic T cell" and "CTL" are used interchangeably herein. Unless otherwise specifically indicated, they refer to a sub-group of T lymphocytes that can recognize non-self cells (for example, tumor/cancer cells, virus-infected cells) and induce the death of such cells.

Unless otherwise specified, the term "HLA-A33" refers to the HLA-A33 type which includes subtypes such as HLA-A*33:03, HLA-A*33:01, and HLA-A*33:04.

Unless otherwise specified, the term "HLA-A01" refers to the HLA-A01 type which includes subtypes such as HLA-A*01:01, HLA-A*01:03, and HLA-A*01:04.

In the context of a subject or patient, the phrase "HLA antigen of a subject (or patient) is HLA-A33" used herein indicates that a subject or patient has the HLA-A33 antigen gene homozygously or heterozygously as the MHC (Major Histocompatibility Complex) Class I molecule, and that the HLA-A33 antigen is expressed in the cells of the subject or patient as the HLA antigen. Similarly, the phrase "HLA antigen of a subject (or patient) is HLA-A01" used herein indicates that a subject or patient has the HLA-A01 antigen gene homozygously or heterozygously as the MHC (Major Histocompatibility Complex) Class I molecule and that the HLA-A01 antigen is expressed as the HLA antigen in the cells of the subject or patient.

As long as the methods and compositions of the present invention are useful in the context of cancer "treatment", the treatment is considered "efficacious" when it achieves clinical advantages, for example, reduction in the size, spreading or metastatic ability of cancer, retardation of cancer progression, alleviation of clinical symptoms of cancer, prolongation of survival period, suppression of postoperative recurrence in a subject. When the treatment is applied prophylactically, "efficacious" means that the treatment retards or prevents cancer formation, or prevents or alleviates clinical symptoms of cancer. Effectiveness is determined in relation to any publicly known method for diagnosing or treating a specific tumor type.

As long as the methods and compositions of the present invention are useful in the context of cancer "prevention (prophylaxis)", the term "prevention (prophylaxis)" herein includes any work that eases the load of cancer-associated mortality or morbidity. Prevention (Prophylaxis) can be carried out at the "primary, secondary and tertiary prevention (prophylaxis) levels". Whereas the primary prevention (prophylaxis) avoids the development of a disease, prevention (prophylaxis) at the secondary and tertiary levels encompasses prevention (prophylaxis) of disease progression and appearance of symptoms, as well as workings intended to reduce adverse effects of the existing disease by restoring functions and reducing disease-associated complications. Alternately, prevention (prophylaxis) can include alleviation of severity of a specific disorder, for example, extensive preventive therapy intended to reduce tumor growth and metastasis.

In the context of the present invention, the treatment and/or prevention (prophylaxis) of cancer and/or prevention (prophylaxis) of postoperative recurrence thereof include either of the events such as inhibition of cancer cell proliferation, tumor involution or regression, induction of remission and suppression of cancer development, tumor regression, as well as reduction or inhibition of metastasis, suppression of postoperative recurrence of cancer, and prolongation of survival period. Effective treatment and/or prevention (prophylaxis) of cancer reduce mortality, improve prognosis of an individual with cancer, reduce the blood levels of tumor markers, and alleviate detectable symptoms associated with cancer. For example, alleviation or improvement of symptoms constitutes effective treatment and/or prevention (prophylaxis), and includes a condition in which the symptoms are stable or alleviated by 10%, 20%, 30% or more.

In the context of the present invention, the term "antibody" refers to immunoglobulins and fragments thereof that are specifically reactive to a designated protein or peptide thereof. An antibody can include human antibodies, primatized antibodies, chimeric antibodies, bispecific antibodies, humanized antibodies, antibodies fused to other proteins or radiolabels, and antibody fragments. Furthermore, an "antibody" herein is used in the broadest sense and specifically covers intact monoclonal antibodies, polyclonal antibodies, multispecific antibodies (e.g., bispecific antibodies) formed from two or more intact antibodies, and antibody fragments so long as they exhibit the desired biological activity. An "antibody" may be antibodies of all classes (e.g., IgA, IgD, IgE, IgG and IgM).

Unless otherwise specified, the technical terms and scientific terms used herein all have the same meanings as terms commonly understood by one of ordinary skill in the art to which the present invention belongs.

II. Peptides

HLA-A33 is an allele commonly seen in Asians, and HLA-A01 is an allele commonly seen in Caucasians (Cao et al., Hum Immunol 2001; 62(9): 1009-30). Thus, an effective method of treating FOXM1-expressing cancers for a great population of Asians or Caucasians can be provided by providing FOXM1-derived CTL-inducing peptides restricted to HLA-A33 or HLA-A01. Thus, the present invention provides FOXM1-derived peptides that are capable of inducing CTLs in an HLA-A33- or HLA-A01-restrictive manner.

The peptides of the present invention are FOXM1-derived peptides that are capable of inducing CTLs in an HLA-A33- or HLA-A01-restrictive manner. Peptides capable of inducing CTLs in an HLA-A33-restrictive manner include peptides having the amino acid sequence selected from among SEQ ID NOs: 1, 2, 3, 6, 7, 11, 12, 17, 18, 20, 22, 24, 26, 32, 33, 36, 39, 41, 42, 45 and 46. Peptides capable of inducing CTLs in an HLA-A01-restrictive manner include peptides having the amino acid sequence selected from among SEQ ID NOs: 48, 49, 50, 52, 53, 55, 20, 56, 57, 58, 59, 60 and 61.

CTLs having a cytotoxic activity specific to these peptides can be established by in vitro stimulation of T cells by dendritic cells (DCs) pulsed with these peptides. The established CTLs show a specific cytotoxic activity against target cells pulsed with each of the peptides.

The FOXM1 gene is overexpressed in cancer cells such as cancer cells in, for example, acute myeloid leukemia (AML), bladder cancer, breast cancer, cervical cancer, cholangiocellular cancer, chronic myeloid leukemia (CML), colon cancer, esophageal cancer, gastric cancer, diffuse gastric cancer, liver cancer, non-small-cell lung cancer (NSCLC), lymphoma, osteosarcoma, ovary cancer, pancreatic cancer, prostate cancer, kidney cancer, small-cell lung cancer (SCLC), soft tissue tumor, testicular tumor and such, but is not expressed in most normal organs. It is thus an excellent target for immunotherapy. Therefore, the peptides of the present invention can be suitably used for cancer immunotherapy. A preferred peptide is a nonapeptide (a peptide consisting of 9 amino acid residues) or a decapeptide (a peptide consisting of 10 amino acid residues), and it is more preferably a peptide consisting of the amino acid sequence selected from among SEQ ID NOs: 1, 2, 3, 6, 7, 11, 12, 17, 18, 20, 22, 24, 26, 32, 33, 36, 39, 41, 42, 45, 46, 48, 49, 50, 52, 53, 55, 56, 57, 58, 59, 60 and 61. For example, a peptide having the amino acid sequence of SEQ ID NO: 2 is suitable for induction of CTLs that show a specific cytotoxic activity against cells expressing HLA-A33 and FOXM1, and can be suitably used for cancer immunotherapy for HLA-A33-positive patients. In a more preferred embodiment, the peptide of the present invention is a peptide consisting of the amino acid sequence of SEQ ID NO: 2. Additionally, for example, a peptide having the amino acid sequence of SEQ ID NO: 56 is suitable for induction of CTLs that show a specific cytotoxic activity against cells expressing HLA-A01 and FOXM1, and can be suitably used for cancer immunotherapy for HLA-A01-positive patients. In a more preferred embodiment, the peptide of the present invention is a peptide consisting of the amino acid sequence of SEQ ID NO: 56.

For the peptides of the present invention, an additional amino acid residue(s) can be made to adjoin the amino acid sequence of the peptide of the present invention, as long as the resultant peptides retain the CTL-inducing ability of the original peptide. The additional amino acid residue(s) may be composed of any types of amino acid(s), as long as they do not impair the CTL-inducing ability of the original peptide. Therefore, the peptides of the present invention encompass peptides having CTL-inducing ability, comprising the amino acid sequence selected from among SEQ ID NOs: 1, 2, 3, 6, 7, 11, 12, 17, 18, 20, 22, 24, 26, 32, 33, 36, 39, 41, 42, 45, 46, 48, 49, 50, 52, 53, 55, 56, 57, 58, 59, 60 and 61. Such peptides are, for example, less than about 40 amino acids, in many cases less than about 20 amino acids, and usually less than about 15 amino acids. Therefore, if the original peptide is a nonapeptide, the peptide of the present invention encompasses peptides that are 10 amino-acid long or 11-40 amino-acid long, which are produced by adjoining additional amino acid(s) to the peptide. Moreover, if the original peptide is a decapeptide, the peptide of the present invention encompasses peptides that are 11-40 amino-acid long. Such a peptide can be, for example, a peptide that is 11-20 amino-acid long or a peptide that is 11-15 amino-acid long. A preferred example of an additional amino acid residue(s) is an amino acid residue(s) adjacent to the amino acid sequence of the peptide of the present invention in the full-length amino acid sequence of FOXM1 (for example, SEQ ID NO: 67, 69, 71, 73 or 75). Therefore, the peptides of the present invention encompass peptides comprising the amino acid sequence selected from among SEQ ID NOs: 1, 2, 3, 6, 7, 11, 12, 17, 18, 20, 22, 24, 26, 32, 33, 36, 39, 41, 42, 45, 46, 48, 49, 50, 52, 53, 55, 56, 57, 58, 59, 60 and 61, and wherein the peptides are peptide fragments of FOXM1 and have CTL-inducing ability.

In general, modifications of one, two or more amino acids in a certain peptide do not affect the functions of the peptide, or in some cases even enhance the desired functions of the original peptide. In fact, modified peptides (i.e., peptides composed of the amino acid sequence in which one, two or several amino acid residues are modified (i.e., substituted, deleted, inserted, and/or added) compared to the original reference sequence) are known to retain the biological activity of the original peptide (Mark et al., Proc Natl Acad Sci USA 1984, 81: 5662-6; Zoller and Smith, Nucleic Acids Res 1982, 10: 6487-500; Dalbadie-McFarland et al., Proc Natl Acad Sci USA 1982, 79: 6409-13). Thus, in one embodiment, the peptides of the present invention can be peptides comprising the amino acid sequence in which one, two or several amino acids are substituted, deleted, inserted and/or added to the amino acid sequence selected from among SEQ ID NOs: 1, 2, 3, 6, 7, 11, 12, 17, 18, 20, 22, 24, 26, 32, 33, 36, 39, 41, 42, 45, 46, 48, 49, 50, 52, 53, 55, 56, 57, 58, 59, 60 and 61 and having CTL-inducing ability.

One skilled in the art can recognize that individual substitutions to an amino acid sequence that alter a single amino acid or a small percentage of amino acids tend to result in the conservation of the properties of the original amino acid side chain(s). Thus, those are frequently referred to as "conservative substitutions" or "conservative modifications"; and modification of a protein by "conservative substitution" or "conservative modification" may result in a modified protein that has similar functions as the original protein. Tables of conservative substitutions presenting functionally similar amino acids are well known in the art. Examples of amino acid side chain characteristics that functionally resemble include, for example, hydrophobic amino acids (A, I, L, M, F, P, W, Y, V), hydrophilic amino acids (R, D, N, C, E, Q, G, H, K, S, T), and side chains having the following functional groups or characteristics in common: an aliphatic side-chain (G, A, V, L, I, P); a hydroxyl group containing side-chain (S, T, Y); a sulfur atom containing side-chain (C, M); a carboxylic acid and amide containing side-chain (D, N, E, Q); a base containing side-chain (R, K, H); and an aromatic containing side-chain (H, F, Y, W). In addition, the following eight groups each contain amino acids that are accepted in the art as conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins 1984).

Such conservatively modified peptides are also encompassed in peptides of the present invention. However, peptides of the present invention are not restricted thereto and can include non-conservative modifications, so long as the modified peptide retains the CTL-inducing ability of the original peptide. Furthermore, modified peptides do not exclude CTL inducible peptides derived from polymorphic variants, interspecies homologues, and alleles of FOXM1.

So long as a peptide retains the CTL-inducing ability of an original peptide, one can modify (i.e., substitute, delete, insert and/or add) a small number (for example, 1, 2 or several) or a small percentage of amino acids. Herein, the term "several" means 5 or fewer amino acids, for example, 4 or 3 or fewer. The percentage of amino acids to be modified is preferably 20% or less, more preferably 15% or less, even more preferably 10% or less or 1 to 5%.

When used in the context of immunotherapy, peptides of the present invention should be presented on the surface of a cell or exosome, preferably as a complex with an HLA antigen. Therefore, it is preferable that the peptides of the present invention possess high binding affinity to the HLA antigen. To that end, the peptides can be modified by substitution, deletion, insertion, and/or addition of the amino acid residues to yield a modified peptide having improved binding affinity. Since the regularity of the sequences of peptides displayed by binding to HLA antigens is already known (Falk, et al., Immunogenetics 1994 40 232-41; Chujoh, et al., Tissue Antigens 1998: 52: 501-9; Takiguchi, et al., Tissue Antigens 2000: 55: 296-302), modifications based on such regularity can be introduced into the peptides of the present invention.

For example, in peptides having binding affinity for HLA Class I, the second amino acid from the N terminus and the C-terminal amino acid are generally anchor residues involved in the binding to HLA Class I (Rammensee H G, et al., Immunogenetics. 1995; 41(4): 178-228). For example, in HLA-A33, phenylalanine, tyrosine, alanine, isoleucine, leucine, and valine for the second amino acid from the N terminus, and arginine and lysine for the C-terminal amino acid are known as anchor residues with high binding affinity for HLA-A33 (Falk, et al., Immunogenetics 1994, 40: 232-41; Takiguchi, et al., Tissue Antigens 2000, 55: 296-302).

Further, in HLA-A33, the first amino acid residue from the N terminus is also known to function as an anchor residue, and it is known that aspartic acid and glutamic acid is preferred as the first amino acid from the N terminus (Falk, et al., Immunogenetics 1994, 40: 232-41; Takiguchi, et al., Tissue Antigens 2000: 55: 296-302). Thus, to maintain or enhance the HLA-A33-binding affinity, there is a possibility that it is desirable to substitute the first amino acid from the N terminus with aspartic acid or glutamic acid, the second amino acid from the N terminus with phenylalanine, tyrosine, alanine, isoleucine, leucine, or valine, and/or the C-terminal amino acid with arginine or lysine.

Therefore, peptides having CTL-inducing ability, which comprise an amino acid sequence in which, in the amino acid sequence selected from among SEQ ID NOs: 1, 2, 3, 6, 7, 11, 12, 17, 18, 20, 22, 24, 26, 32, 33, 36, 39, 41, 42, 45 and 46, the first amino acid from the N terminus is substituted with aspartic acid or glutamic acid, the second amino acid from the N terminus is substituted with phenylalanine, tyrosine, alanine, isoleucine, leucine, or valine, and/or the C-terminal amino acid is substituted with arginine or lysine are encompassed by the peptides of the present invention.

In a preferred embodiment, the peptide of the present invention may be a peptide having CTL-inducing ability, which consists of an amino acid sequence in which, in the amino acid sequence selected from among SEQ ID NOs: 1, 2, 3, 6, 7, 11, 12, 17, 18, 20, 22, 24, 26, 32, 33, 36, 39, 41, 42, 45 and 46, the first amino acid from the N terminus is substituted with aspartic acid or glutamic acid, the second amino acid from the N terminus is substituted with phenylalanine, tyrosine, alanine, isoleucine, leucine, or valine, and/or the C-terminal amino acid is substituted with arginine or lysine.

That is, the peptides of the present invention encompass a peptide having CTL-inducing ability, which comprises an amino acid sequence having one or more substitutions selected from (a) to (c) below in the amino acid sequence selected from among SEQ ID NOs: 1, 2, 3, 6, 7, 11, 12, 17, 18, 20, 22, 24, 26, 32, 33, 36, 39, 41, 42, 45 and 46:

(a) the first amino acid from the N terminus is substituted with aspartic acid or glutamic acid;
(b) the second amino acid from the N terminus is substituted with phenylalanine, tyrosine, alanine, isoleucine, leucine, or valine; and
(c) the C-terminal amino acid is substituted with arginine or lysine.

In a preferred embodiment, the peptide of the present invention may be a peptide having CTL-inducing ability, which consists of an amino acid sequence having one or more substitutions selected from (a) to (c) above in the amino acid sequence selected from among SEQ ID NOs: 1, 2, 3, 6, 7, 11, 12, 17, 18, 20, 22, 24, 26, 32, 33, 36, 39, 41, 42, 45 and 46. In the present invention, the preferred number of substitutions is 1, 2 or 3 substitutions selected from (a) to (c) above.

Furthermore, the peptide of the present invention can be a peptide having CTL-inducing ability, which comprises an amino acid sequence in which, in the amino acid sequence selected from among SEQ ID NOs: 1, 2, 3, 6, 7, 11, 12, 17, 18, 20, 22, 24, 26, 32, 33, 36, 39, 41, 42, 45 and 46, the second amino acid from the N terminus is substituted with phenylalanine, tyrosine, alanine, isoleucine, leucine, or valine, and/or the C-terminal amino acid is substituted with arginine or lysine. Preferably, the peptide of the present invention can be a peptide having CTL-inducing ability, which consists of an amino acid sequence in which, in the amino acid sequence selected from among SEQ ID NOs: 1, 2, 3, 6, 7, 11, 12, 17, 18, 20, 22, 24, 26, 32, 33, 36, 39, 41, 42, 45 and 46, the second amino acid from the N terminus is substituted with phenylalanine, tyrosine, alanine, isoleucine, leucine, or valine, and/or the C-terminal amino acid is substituted with arginine or lysine. That is, the peptide of the present invention can be a peptide having CTL-inducing ability, which comprises an amino acid sequence having one or more substitutions selected from (a) and (b) below in the amino acid sequence selected from among SEQ ID NOs: 1, 2, 3, 6, 7, 11, 12, 17, 18, 20, 22, 24, 26, 32, 33, 36, 39, 41, 42, 45 and 46:

(a) the second amino acid from the N terminus is substituted with phenylalanine, tyrosine, alanine, isoleucine, leucine, or valine; and
(b) the C-terminal amino acid is substituted with arginine or lysine.

In a preferred embodiment, the peptide of the present invention may be a peptide having CTL-inducing ability, which consists of an amino acid sequence having one or more substitutions selected from (a) and (b) above in the amino acid sequence selected from among SEQ ID NOs: 1, 2, 3, 6, 7, 11, 12, 17, 18, 20, 22, 24, 26, 32, 33, 36, 39, 41, 42, 45 and 46. In a more preferred embodiment, the second amino acid from the N terminus is substituted with phenylalanine or tyrosine.

In HLA-A01, aspartic acid and glutamic acid for the third amino acid from the N terminus, and tyrosine for the C-terminal amino acid are known as anchor residues with high binding affinity for HLA-A01. Further, it is known that there are auxiliary anchor residues at position 2 from the N terminus for HLA-A01 and that threonine and serine are preferred as the second amino acid from the N terminus (Kubo, R. T Journal of Immunology 1994, 152: 3913; Gambacorti-Passerini, C. Clinical Cancer Research 1997, 3: 675-83; Falk, K. Immunogenetics 1994, 40: 238-41).

Thus, to maintain or enhance the HLA-A01-binding affinity, there is a possibility that it is desirable to substitute the third amino acid from the N terminus with aspartic acid or glutamic acid, and/or the C-terminal amino acid with tyrosine. Another possibility is that it is desirable to substitute the second amino acid from the N terminus with threonine or serine. Therefore, peptides having CTL-inducing ability, which comprise an amino acid sequence in which, in the amino acid sequence selected from among SEQ ID NOs: 48, 49, 50, 52, 53, 55, 20, 56, 57, 58, 59, 60 and 61, the second amino acid from the N terminus is substituted with threonine or serine, the third amino acid from the N terminus is substituted with aspartic acid or glutamic acid, and/or the C-terminal amino acid is substituted with tyrosine are encompassed by the peptides of the present invention.

In a preferred embodiment, the peptide of the present invention may be a peptide having CTL-inducing ability, which consists of an amino acid sequence in which, in the amino acid sequence selected from among SEQ ID NOs: 48, 49, 50, 52, 53, 55, 20, 56, 57, 58, 59, 60 and 61, the second amino acid from the N terminus is substituted with threonine or serine, the third amino acid from the N terminus is substituted with aspartic acid or glutamic acid, and/or the C-terminal amino acid is substituted with tyrosine.

That is, the peptides of the present invention encompass a peptide having CTL-inducing ability, which comprises an amino acid sequence having one or more substitutions selected from (a) to (c) below in the amino acid sequence selected from among SEQ ID NOs: 48, 49, 50, 52, 53, 55, 20, 56, 57, 58, 59, 60 and 61:

(a) the second amino acid from the N terminus is substituted with threonine or serine;

(b) the third amino acid from the N terminus is substituted with aspartic acid or glutamic acid; and (c) the C-terminal amino acid is substituted with tyrosine.

In a preferred embodiment, the peptide of the present invention can be a peptide having CTL-inducing ability, which consists of an amino acid sequence having one or more substitutions selected from (a) to (c) above in the amino acid sequence selected from among SEQ ID NOs: 48, 49, 50, 52, 53, 55, 20, 56, 57, 58, 59, 60 and 61. In the present invention, the preferred number of substitutions is 1, 2 or 3 substitutions selected from among (a) to (c) above.

Furthermore, the peptide of the present invention may be a peptide having CTL-inducing ability, which comprises an amino acid sequence in which, in the amino acid sequence selected from among SEQ ID NOs: 48, 49, 50, 52, 53, 55, 20, 56, 57, 58, 59, 60 and 61, the third amino acid from the N terminus is substituted with aspartic acid or glutamic acid, and/or the C-terminal amino acid is substituted with tyrosine. Preferably, the peptide of the present invention may be a peptide having CTL-inducing ability, which consists of an amino acid sequence in which, in the amino acid sequence selected from among SEQ ID NOs: 48, 49, 50, 52, 53, 55, 20, 56, 57, 58, 59, 60 and 61, the third amino acid from the N terminus is substituted with aspartic acid or glutamic acid, and/or the C-terminal amino acid is substituted with tyrosine. That is, the peptide of the present invention can be a peptide having CTL-inducing ability, which comprises an amino acid sequence having one or more substitutions selected from (a) and (b) below in the amino acid sequence selected from among SEQ ID NOs: 48, 49, 50, 52, 53, 55, 20, 56, 57, 58, 59, 60 and 61:

(a) the third amino acid from the N terminus is substituted with aspartic acid or glutamic acid; and (b) the C-terminal amino acid is substituted with tyrosine.

In a preferred embodiment, the peptide of the present invention may be a peptide having CTL-inducing ability, which consists of an amino acid sequence having one or more substitutions selected from (a) to (b) above in the amino acid sequence selected from among SEQ ID NOs: 48, 49, 50, 52, 53, 55, 20, 56, 57, 58, 59, 60 and 61.

Substitution(s) may be introduced into amino acid(s) not only at the anchor site(s), but also at a position(s) of potential T cell receptor (TCR) recognition site(s) of the peptides. Several research studies have demonstrated that a peptide that has amino acid substitutions, such as CAP1, $p53_{(264-272)}$, Her-2/$neu_{(369-377)}$ or $gp100_{(209-217)}$, may have equal to or better activity than that of the original peptide (Zaremba et al. Cancer Res., 1997, 57, 4570-7; T. K. Hoffmann et al. J Immunol., 2002, 168(3): 1338-47; S. O. Dionne et al. Cancer Immunol immunother., 2003, 52: 199-206; and S. O. Dionne et al. Cancer Immunology, Immunotherapy, 2004, 53, 307-14).

The present invention also contemplates that one, two or several amino acids can be added to the N terminus and/or C terminus of the peptides of the present invention (for example, peptides consisting of the amino acid sequence selected from among SEQ ID NOs: 1, 2, 3, 6, 7, 11, 12, 17, 18, 20, 22, 24, 26, 32, 33, 36, 39, 41, 42, 45, 46, 48, 49, 50, 52, 53, 55, 56, 57, 58, 59, 60 and 61). More specifically, the present invention provides peptides consisting of amino acid sequences in which one, two or several amino acids are added to either or both of the N terminus and C terminus of the amino acid sequences referred by each of the SEQ ID NOs. Such modified peptides that retain CTL-inducing ability are also included in the present invention. For example, when a peptide in which one, two or several amino acids are added to the N terminus and/or C terminus of a peptide consisting of the amino acid sequence of SEQ ID NO: 2 or 56 is contacted with an APC(s), it is incorporated into the APC(s) and processed to become a peptide consisting of the amino acid sequence of SEQ ID NO: 2 or 56. It can then induce CTLs through presentation on the cell surface of an APC via the antigen presentation pathway. More specifically, peptides of the present invention can be peptides in which one, two or several amino acids are added to either or both of the N terminus and C terminus.

Further, in another embodiment of the present invention, peptides consisting of amino acid sequences comprising one, two or several amino acid substitutions in the amino acid sequences referred by each of the SEQ ID NOs and in which one, two or several amino acids are added to either or both of the N terminus and C terminus of these substituted amino acid sequences are provided.

When the peptides of the present invention comprise amino acid substitution(s), the desired substitution positions can be, for example, one, two, or three positions selected from the first position from the N terminus, the second position from the N terminus, and the C terminus in the amino acid sequences referred by SEQ ID NOs: 1, 2, 3, 6, 7, 11, 12, 17, 18, 20, 22, 24, 26, 32, 33, 36, 39, 41, 42, 45 and 46 or one, two, or three positions selected from the second position from the N terminus, the third position from the N terminus and the C terminus in the amino acid sequences referred by SEQ ID NOs: 48, 49, 50, 52, 53, 55, 20, 56, 57, 58, 59, 60 and 61 comprised in the peptides of the present invention.

However, when the amino acid sequence of a peptide is identical to a portion of the amino acid sequence of an endogenous or exogenous protein having a different function, side effects such as autoimmune disorders and/or allergic symptoms against specific substances may be induced. Therefore, it is preferable to perform homology searches using available databases to avoid situations in which the amino acid sequence of the peptide matches the amino acid sequence of another protein. When it becomes clear from the homology searches that no peptide exists with as few as 1 or 2 amino acid differences as compared to the objective peptide, the objective peptide can be modified in order to increase its binding affinity with HLA antigens, and/or increase its CTL-inducing ability without danger of such side effects.

Peptides in which one, two or several amino acids of a peptide of the present invention are modified are predicted to be able to retain CTL-inducing ability of the original peptide; however, it is preferable to verify the CTL-inducing ability of the modified peptides. Herein, the "peptide having CTL-inducing ability (CTL inducibility)" refers to a peptide that induces CTLs through APCs stimulated with the peptide.

"CTL induction" includes induction of differentiation into CTLs, induction of CTL activation, induction of CTL proliferation, induction of CTL's cytotoxic activity, induction of CTL-mediated dissolution of target cells, and induction of increase of IFN-gamma production of CTLs.

The CTL-inducing ability can be confirmed by stimulating APCs that express an HLA antigen of interest (for example, B lymphocytes, macrophages, or dendritic cells) with a peptide, and mixing it with CD8-positive T cells; and then measuring IFN-gamma released by CTLs against the target cells. For the APCs, human peripheral blood mononuclear cell-derived dendritic cells can be preferably used. As a reaction system, transgenic animals generated to express an HLA antigen can be used. Alternatively, for example, the target cells may be radio-labelled with $^{51}Cr$ or such, and the cytotoxic activity of the peptide-induced CTLs may be calculated from the radioactivity emitted from the target cells. Alternatively, in the presence of peptide-stimulated APCs, it is possible to evaluate the CTL-inducing ability by measuring the IFN-gamma produced and released by CTLs, and visualizing the inhibition zone on the media using anti-IFN-gamma monoclonal antibodies.

In addition to the modifications above, the peptides of the present invention can be linked to other peptides as long as the resultant linked peptide retains the CTL-inducing ability. An example of an appropriate peptide to be linked with the peptides of the present invention includes a CTL-inducing peptide derived from other TAAs. Further, the peptides of the present invention can also be linked with each other. Suitable linkers for use in linking peptides are known in the art, and for example, linkers such as AAY (P. M. Daftarian et al., J Trans Med 2007, 5: 26), AAA, NKRK (SEQ ID NO: 62) (R. P. M. Sutmuller et al., J Immunol. 2000, 165: 7308-15), or K (S. Ota et al., Can Res. 62, 1471-6; K. S. Kawamura et al., J Immunol. 2002, 168: 5709-15) can be used. Peptides can be linked in various arrangements (for example, catenulate, repeated, etc.), and one can also link three or more peptides.

The peptides of the present invention can also be linked to other substances as long as the resultant linked peptide retains the CTL-inducing ability. Examples of an appropriate substance to be linked with a peptide of the present invention include, for example, a peptide, a lipid, a sugar or sugar chain, an acetyl group, and a naturally-occurring or synthetic polymer. The peptides of the present invention can be modified by glycosylation, side-chain oxidation, phosphorylation or such, as long as their CTL-inducing ability is not impaired. One can also perform such types of modifications to confer additional functions (for example, targeting function and delivery function) or to stabilize the peptide.

For example, to increase the in vivo stability of a peptide, it is known in the art to introduce D-amino acids, amino acid mimetics or non-naturally occurring amino acids, and this concept may also be applied to peptides of the present invention. Peptide stability can be assayed by several methods. For example, stability can be tested by using a peptidase as well as various biological media such as human plasma and serum (see, e.g., Verhoef et al., Eur J Drug Metab Pharmacokin 1986, 11: 291-302).

Further, as stated above, among the modified peptides in which one, two, or several amino acid residues have been substituted, deleted, inserted and/or added, those having the same or higher activity as compared to original peptides can be screened for or selected. Thus, the present invention also provides methods of screening for or selecting modified peptides that have the same or higher activity than that of the original peptide. Specifically, the present invention provides a method of screening for a peptide having CTL-inducing ability, wherein the method comprises the steps of:

(a) generating candidate sequences consisting of an amino acid sequence in which one, two, or several amino acid residues are substituted, deleted, inserted and/or added to the original amino acid sequence consisting of the amino acid sequence selected from among SEQ ID NOs: 1, 2, 3, 6, 7, 11, 12, 17, 18, 20, 22, 24, 26, 32, 33, 36, 39, 41, 42, 45, 46, 48, 49, 50, 52, 53, 55, 56, 57, 58, 59, 60 and 61;
(b) selecting from among the candidate sequences generated in (a), a candidate sequence that does not have a significant homology (sequence identity) with any known human gene product other than FOXM1;
(c) contacting a peptide consisting of the candidate sequence selected in (b) with APCs;
(d) contacting the APCs of (c) with CD8-positive T cells; and
(e) selecting a peptide that has an equal to or higher CTL-inducing ability than that of a peptide consisting of the original amino acid sequence.

Herein, the peptide of the present invention is also described as a "FOXM1 peptide(s)".

III. Preparation of Peptides of the Present Invention

Well known techniques can be used to prepare peptides of the present invention. For example, recombinant DNA technology or chemical synthesis can be used to prepare peptides of the present invention. Peptides of the present invention can be synthesized individually, or as longer polypeptides including two or more peptides. Peptides of the present invention can be isolated from host cells or synthesis reaction products after they are produced in the host cells using recombinant DNA technology or after they are chemically synthesized. That is, peptides of the present invention can be purified or isolated so as not to substantially contain other host-cell proteins and fragments thereof, or any other chemical substances.

The peptides of the present invention may contain modifications, such as glycosylation, side chain oxidation, or phosphorylation provided such modifications do not destroy the biological activity of the original peptide. Other illustrative modifications include incorporation of D-amino acids or other amino acid mimetics that may be used, for example, to increase the serum half life of the peptides.

A peptide of the present invention can be obtained through chemical synthesis based on the selected amino acid sequence. Examples of conventional peptide synthesis methods that can be adapted to the synthesis include the methods described in the documents below:

(i) Peptide Synthesis, Interscience, New York, 1966;
(ii) The Proteins, Vol. 2, Academic Press, New York, 1976;

(iii) "Peptide Synthesis" (in Japanese), Maruzen Co., 1975;
(iv) "Basics and Experiment of Peptide Synthesis" (in Japanese), Maruzen Co., 1985;
(v) "Development of Pharmaceuticals" (in Japanese), Continued Vol. 14 (peptide synthesis), Hirokawa, 1991;
(vi) WO99/67288; and
(vii) Barany G. & Merrifield R. B., Peptides Vol. 2, Solid Phase Peptide Synthesis, Academic Press, New York, 1980, 100-118.

Alternatively, the peptides of the present invention can be obtained by adapting any known genetic engineering methods for producing peptides (e.g., Morrison J, J Bacteriology 1977, 132: 349-51; Clark-Curtiss & Curtiss, Methods in Enzymology (Wu et al.) 1983, 101: 347-62). For example, first, a suitable vector harboring a polynucleotide encoding the peptide of the present invention in an expressible form (e.g., downstream of a regulatory sequence corresponding to a promoter sequence) is prepared and transformed into a suitable host cell. The host cell is then cultured to produce the peptide of the present invention. The peptide of the present invention can also be produced in vitro using an in vitro translation system.

IV. Polynucleotides

The present invention also provides a polynucleotide which encodes any of the peptides of the present invention. These include polynucleotides derived from the naturally occurring FOXM1 gene (e.g., GenBank Accession No. NM_202003 (SEQ ID NO: 52), NM_001243088 (SEQ ID NO: 54), NM_001243089 (SEQ ID NO: 56), NM_021953 (SEQ ID NO: 58) or NM202002 (SEQ ID NO: 60)) as well as those having a conservatively modified nucleotide sequence thereof. Herein, the phrase "conservatively modified nucleotide sequence" refers to sequences which encode identical or essentially identical amino acid sequences. Due to the degeneracy of the genetic code, a large number of functionally identical nucleic acids encode any given protein. For instance, the codons GCA, GCC, GCG, and GCU all encode the amino acid alanine. Thus, at every position where an alanine is specified by a codon, the codon can be altered to any of the corresponding codons described above without altering the encoded polypeptide. Such nucleic acid variations are "silent variations", which are one species of conservatively modified variations. Every nucleic acid sequence herein which encodes a peptide also describes every possible silent variation of the nucleic acid. One of ordinary skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a peptide is implicitly described in each disclosed sequence.

The polynucleotide of the present invention can be composed of DNA, RNA, and derivatives thereof. A DNA is suitably composed of bases such as A, T, C, and G, and T is replaced by U in an RNA.

The polynucleotide of the present invention can encode multiple peptides of the present invention with or without intervening amino acid sequences in between. For example, the intervening amino acid sequence can provide a cleavage site (e.g., enzyme recognition sequence) of the polynucleotide or the translated peptides. Furthermore, the polynucleotide can include any additional sequences to the coding sequence encoding the peptide of the present invention. For example, the polynucleotide can be a recombinant polynucleotide that includes regulatory sequences required for the expression of the peptide or can be an expression vector (e.g., plasmid) with marker genes and such. In general, such recombinant polynucleotides can be prepared by the manipulation of polynucleotides through conventional recombinant techniques using, for example, polymerases and endonucleases.

Both recombinant and chemical synthesis techniques can be used to produce the polynucleotides of the present invention. For example, a polynucleotide can be produced by insertion into an appropriate vector, which can be expressed when transfected into a competent cell. Alternatively, a polynucleotide can be amplified using PCR techniques or expression in suitable hosts (see, e.g., Sambrook et al., Molecular Cloning: A Laboratory Manual, Cold Spring Harbor Laboratory, New York, 1989). Alternatively, a polynucleotide can be synthesized using the solid phase techniques, as described in Beaucage S L & Iyer R P, Tetrahedron 1992, 48: 2223-311; Matthes et al., EMBO J 1984, 3: 801-5. The linkage products of several peptides that can be obtained in this manner can be purified as necessary and administered in this linked stated. In this case, the linked peptides produce antigen-presentable peptides by processing and the CTL-inducing activity of each of the peptides is elicited. Accordingly, when linking peptides, it is preferable that peptides with a same HLA restriction are combined. Alternatively, peptides can be administered as a mixture of individual peptides by cleaving the linkage portion.

V. Exosomes

The present invention further provides intracellular vesicles, referred to as exosomes, that present complexes formed between the peptides of the present invention and HLA antigens on their surface. Exosomes can be prepared, for example, using the methods detailed in JPH11-510507 and WO99/03499, and can be prepared using APCs obtained from patients who are subject to treatment and/or prevention (prophylaxis). The exosomes of the present invention can be inoculated as vaccines, in a fashion similar to the peptides of the present invention.

The type of the HLA antigens included in the above-described complexes must match that of the subject in need of treatment and/or prevention (prophylaxis). For example, HLA-A33 (for example, HLA-A*33:03) are alleles widely and generally seen in Asians, and this HLA antigen type is considered to be suitable for treatment in Asian patients. Further, HLA-A01 (for example, HLA-A*01:01) is an HLA allele frequently seen in Caucasians, and this HLA antigen type is considered to be suitable for treatment in Caucasian patients. Typically in clinical practice, it is possible to select an appropriate peptide that has a high level of binding affinity for a specific HLA antigen or that has CTL-inducing ability by antigen presentation mediated by a specific HLA antigen, by studying in advance the HLA antigen type of the patient in need of treatment.

The exosomes of the present invention present on their surface a complex of a peptide of the present invention and HLA-A33 or HLA-A01. When the HLA that forms a complex with a peptide of the present invention is HLA-A33, the peptide of the present invention is preferably a peptide having the amino acid sequence selected from among SEQ ID NOs: 1, 2, 3, 6, 7, 11, 12, 17, 18, 20, 22, 24, 26, 32, 33, 36, 39, 41, 42, 45 and 46 or a modified peptide thereof, and more preferably a peptide consisting of the amino acid sequence selected from among SEQ ID NOs: 1, 2, 3, 6, 7, 11, 12, 17, 18, 20, 22, 24, 26, 32, 33, 36, 39, 41, 42, 45 and 46 or a modified peptide thereof. Further, when the HLA that forms a complex with a peptide of the present invention is HLA-A01, the peptide of the present invention is preferably a peptide having the amino acid sequence selected from among SEQ ID NOs: 48, 49, 50, 52, 53, 55, 20, 56, 57, 58, 59, 60 and 61 or a modified peptide thereof, and more preferably a peptide consisting of the amino acid sequence selected from among SEQ ID NOs: 48, 49, 50, 52, 53, 55, 20, 56, 57, 58, 59, 60 and 61 or a modified peptide thereof.

VI. Antigen-Presenting Cells (APCs)

The present invention further provides APCs that present on their surface complexes formed between HLA antigens and peptides of the present invention. Alternatively, the present invention provides APCs having on their cell surface complexes formed between HLA antigens and peptides of the present invention. The APCs of the present invention can be isolated APCs. When used in the context of cells (APCs, CTLs, etc.), the term "isolated" means that the cells are separated from another type of cells. The APCs of the present invention may be APCs induced from APCs derived from the patient to be subjected to treatment and/or prevention (prophylaxis), and can be administered as a vaccine by themselves or in combination with other drugs including a peptide(s), an exosome(s) or a CTL(s) of the present invention.

The APCs of the present invention are not limited to specific types of cells, and may be cells known to present proteinaceous antigens on their cell surface so as to be recognized by lymphocytes, for example, dendritic cells (DCs), Langerhans cells, macrophages, B cells, and activated T cells. Since DC is a representative APC that has the strongest CTL-inducing activity among APCs, DCs can be preferably used as the APCs of the present invention. In the present invention, the preferable DC is an isolated DC derived from human. Further, the APCs of the present invention can also be mixtures of multiple types of cells having an antigen-presenting function and can be mixtures of APCs each of which presents different types of the peptides of the present invention.

For example, APCs of the present invention can be obtained by isolating DCs from peripheral blood mononuclear cells and then stimulating them in vitro, ex vivo, or in vivo with the peptides of the present invention. When the peptide of the present invention is administered to a subject, APCs presenting the peptide of the present invention are induced in the body of the subject. Therefore, after the peptides of the present invention are administered to a subject, the APCs of the present invention can be obtained by collecting APCs from the subject. Alternatively, the APCs of the present invention can be obtained by contacting APCs collected from a subject with a peptide of the present invention.

In order to induce an immune response against FOXM1-expressing cancer cells in a subject, the APCs of the present invention can be administered to the subject by themselves or in combination with other drugs including peptide(s), exosome(s) or CTL(s) of the present invention. For example, the ex vivo administration can comprise the following steps of:

(a) collecting APCs from a first subject;

(b) contacting the APCs of step (a) with a peptide; and (c) administering the APCs of step (b) to a second subject.

The first subject and the second subject may be the same individual, or may be different individuals. When the first subject and the second subject are different individuals, it is preferable that the HLAs of the first subject and the second subject are of the same type. The APC obtained in step (b) above can be a vaccine for cancer treatment and/or prevention (prophylaxis).

The APCs of the present invention obtained by a method such as described above have CTL-inducing ability. The term "CTL-inducing ability (CTL inducibility)" used in the context of an APC(s) refers to the ability of the APC to be able to induce a CTL(s) when placed in contact with a CD8-positive T cell(s). Further, the "CTL-inducing ability (CTL inducibility)" includes the ability of an APC to induce CTL activation, the ability of an APC to induce CTL proliferation, the ability of an APC to facilitate CTL-mediated dissolution of target cells, and the ability of an APC to increase CTL-mediated IFN-gamma production. The CTL(s) induced by the APC of the present invention is a CTL(s) specific to FOXM1 and demonstrates a specific cytotoxic activity against FOXM1-expressing cells.

In addition to the above-described methods, the APCs of the present invention can be prepared by introducing a polynucleotide encoding a peptide of the present invention into APCs in vitro. The polynucleotide to be introduced can be in the form of DNA or RNA. The method of introduction is not particularly limited, and examples thereof include various methods conventionally performed in the art such as lipofection, electroporation and the calcium phosphate method. More specifically, methods described in Cancer Res 1996, 56: 5672-7; J Immunol 1998, 161: 5607-13; J Exp Med 1996, 184: 465-72; and JP2000-509281 can be used. By introducing a polynucleotide encoding a peptide of the present invention into an APC, the polynucleotide is transcribed and translated in the cell, and then the produced peptide is processed by MHC Class I and proceeds through a presentation pathway to present the peptide of the present invention on the cell surface of the APC.

In a preferred embodiment, the APC of the present invention presents on its cell surface a complex formed between a peptide of the present invention and HLA-A33 (more preferably HLA-A*33:03) or HLA-A01 (more preferably HLA-A*01:01). When the HLA that forms a complex with a peptide of the present invention is HLA-A33, the peptide of the present invention is preferably a peptide having the amino acid sequence selected from among SEQ ID NOs: 1, 2, 3, 6, 7, 11, 12, 17, 18, 20, 22, 24, 26, 32, 33, 36, 39, 41, 42, 45 and 46 or a modified peptide thereof, and more preferably a peptide consisting of the amino acid sequence selected from among SEQ ID NOs: 1, 2, 3, 6, 7, 11, 12, 17, 18, 20, 22, 24, 26, 32, 33, 36, 39, 41, 42, 45 and 46. When the HLA that forms a complex with a peptide of the present invention is HLA-A01, the peptide of the present invention is preferably a peptide having the amino acid sequence selected from among SEQ ID NOs: 48, 49, 50, 52, 53, 55, 20, 56, 57, 58, 59, 60 and 61 or a modified peptide thereof, and more preferably a peptide consisting of the amino acid sequence selected from among SEQ ID NOs: 48, 49, 50, 52, 53, 55, 20, 56, 57, 58, 59, 60 and 61.

The APC(s) of the present invention is preferably an APC(s) induced by a method comprising a step described (a) or (b) below:

(a) contacting an APC(s) expressing at least one HLA selected from among HLA-A33 (more preferably HLA-A*33:03) and HLA-A01 (more preferably HLA-A*01:01) with a peptide of the present invention; or (b) introducing a polynucleotide encoding a peptide of the present invention into an APC(s) expressing at least one HLA selected from among HLA-A33 (more preferably HLA-A*33:03) and HLA-A01 (more preferably HLA-A*01:01).

The peptide of the present invention to be contacted with the HLA-A33-expressing APC(s) is preferably a peptide having the amino acid sequence selected from among SEQ ID NOs: 1, 2, 3, 6, 7, 11, 12, 17, 18, 20, 22, 24, 26, 32, 33, 36, 39, 41, 42, 45 and 46 or a modified peptide thereof, and more preferably a peptide consisting of the amino acid sequence selected from among SEQ ID NO: 1, 2, 3, 6, 7, 11, 12, 17, 18, 20, 22, 24, 26, 32, 33, 36, 39, 41, 42, 45 and 46.

The peptide of the present invention to be contacted with the HLA-A01-expressing APC(s) is preferably a peptide having the amino acid sequence selected from among SEQ ID NOs: 48, 49, 50, 52, 53, 55, 20, 56, 57, 58, 59, 60 and 61 or a modified peptide thereof, and more preferably a peptide consisting of the amino acid sequence selected from among SEQ ID NOs: 48, 49, 50, 52, 53, 55, 20, 56, 57, 58, 59, 60 and 61.

The present invention provides use of a peptide of the present invention for the manufacture of a pharmaceutical composition that induces an APC(s) having CTL-inducing ability. In addition, the present invention provides a method or process of manufacturing a pharmaceutical composition that induces an APC(s) having CTL-inducing ability. Further, the present invention provides a peptide of the present invention for inducing an APC(s) having CTL-inducing ability.

VII. Cytotoxic T Lymphocytes (CTLs)

The CTL induced by a peptide of the present invention can be used as a vaccine in a similar manner to the peptide of the present invention for in vivo enhancing an immune response targeting FOXM1-expressing cancer cell. Thus, the present invention provides CTLs that are induced or activated by a peptide of the present invention. The CTLs of the present invention are CTLs that target a peptide of the present invention, and are capable of binding to a complex of a peptide of the present invention and an HLA antigen. Binding of a CTL to the complex is mediated via a T cell receptor (TCR) present on the cell surface of the CTL. The CTLs of the present invention can be isolated CTLs. The preferable CTLs are isolated CTLs of human origin. The CTLs of the present invention can also be mixtures of CTLs each of which targets different types of peptides of the present invention.

The CTLs of the present invention can be obtained by (1) administering a peptide of the present invention to a subject, (2) stimulating APCs and CD8-positive T cells, or peripheral blood mononuclear cells (PBMCs) derived from a subject with a peptide of the present invention in vitro, (3) contacting in vitro CD8-positive T cells or PBMCs with APCs or exosomes that present on their surface a complex of an HLA antigen and a peptide of the present invention, or (4) introducing into CD8-positive T cells a vector comprising a polynucleotide encoding each subunit of a T cell receptor (TCR) capable of binding to a peptide of the present invention presented on cell surface via an HLA antigen. The exosomes and APCs used in the method of (2) or (3) above can be prepared by methods described in the "V. Exosomes" and "VI. Antigen-presenting cells (APCs)" sections, respectively, and the details of the method of (4) above will be described in the "VIII. T cell receptor (TCR)" section.

The CTLs of the present invention can be administered by themselves to patients who are subject to treatment and/or prevention (prophylaxis), or in combination with other drugs including peptide(s), APC(s) or exosome(s) of the present invention for the purpose of regulating effects. Further, the CTLs of the present invention can be CTLs induced from CD8-positive T cells derived from the patients who are subject to administration of the CTLs. The CTLs of the present invention act specifically on target cells that present the peptides of the present invention, for example, the same peptides used to induce the CTLs of the present invention. The target cells may be cells that endogenously express FOXM1, such as cancer cells, or cells transfected with the FOXM1 gene. Cells that present a peptide of the present invention on their cell surface due to stimulation by the peptide can become a target of attack by the CTLs of the present invention. The cells targeted by the CTLs of the present invention are preferably cells that are positive for at least one of HLA-A33 (more preferably HLA-A*33:03) and HLA-A01 (more preferably HLA-A*01:01).

In a preferred embodiment, the CTLs of the present invention target specifically cells that express both FOXM1 and at least one HLA selected from among HLA-A33 (more preferably HLA-A*33:03) and HLA-A01 (more preferably HLA-A*01:01). In the present invention, the cells targeted by the CTLs can be cells that have any of the alleles of HLA-A33 and HLA-A01 homozygously or heterozygously.

Herein, that the CTL "targets" cells refers to CTL recognition of cells that present on their cell surface a complex of HLA and a peptide of the present invention and demonstration of a cytotoxic activity against the cells. Further, "specifically target" refers to that the CTLs demonstrate a cytotoxic activity against those cells, but do not show a damaging activity to other cells. The expression "recognize cells" used in the context of CTLs refers to binding to a complex of HLA and a peptide of the present invention presented on cell surface via its TCR, and demonstrating a specific cytotoxic activity against the cell. Therefore, the CTLs of the present invention are preferably CTLs that can bind via TCR to a complex formed between a peptide of the present invention and HLA-A33 (more preferably HLA-A*33:03) or HLA-A01 (more preferably HLA-A*01:01) presented on cell surface.

Furthermore, the CTLs of the present invention are preferably CTLs induced by a method comprising a step described in (a) or (b) below:

(a) contacting in vitro CD8-positive T cells with APCs or exosomes that present on their surface a complex of a peptide of the present invention and HLA-A33 (more preferably HLA-A*33:03) or HLA-A01 (more preferably HLA-A*01:01); or (b) introducing into CD8-positive T cells a polynucleotide encoding each subunit of a TCR capable of binding to a peptide of the present invention presented on cell surface by HLA-A33 (more preferably HLA-A*33:03) or HLA-A01 (more preferably HLA-A*01:01). The CTLs induced by this method are cells having TCRs that specifically recognize the complex of the peptide and HLA antigen used for the induction. Accordingly, they are cells having a structural difference from other CTLs that have different reaction specificity due to the difference in the structure of the TCR.

VIII. T Cell Receptors (TCRs)

The present invention also provides compositions comprising a polynucleotide encoding each subunit of a TCR capable of binding to a peptide of the present invention presented on cell surface by an HLA antigen, and methods of using the same. The polynucleotide confers CD8-positive T cells with specificity against FOXM1-expressing cancer cells through expression of a TCR capable of binding to a peptide of the present invention presented on target cell surface by an HLA antigen on the surface of CD8-positive T cells. Polynucleotides encoding an alpha chain(s) and a beta chain(s) can be identified as the TCR subunit of the CTL induced by a peptide of the present invention by using known methods in the art (WO2007/032255 and Morgan et al., J Immunol, 171, 3288 (2003)). For example, PCR methods are preferred for TCR analysis. Without being limited thereto, PCR primers for analysis may be, for example, a primer set(s) for amplification by combining the 5' side primer and the 3' side primer(s) below:

5' Side Primer:

5'-R Primer (5'-gtctaccaggcattcgcttcat-3') (SEQ ID NO: 62)

3' Side Primers:

TCR-Alpha-Chain C-Region-Specific

3-TRa-C Primer (5'-tcagctggaccacagccgcagcgt-3') (SEQ ID NO: 63)

TCR-Beta-Chain C1-Region-Specific

3-TRb-C1 Primer (5'-tcagaaatcctttctcttgac-3') (SEQ ID NO: 64) or

TCR-Beta-Chain C2-Region-Specific

3-TR-beta-C2 Primer (5'-ctagcctctggaatcctttctctt-3') (SEQ ID NO: 65)

The TCRs formed by introducing the identified polynucleotides into CD8-positive T cells can bind with high binding affinity to the target cells that present a peptide of the present invention, and mediates efficient killing of the target cells presenting a peptide of the present invention in vivo and in vitro.

A polynucleotide encoding each TCR subunit can be incorporated into an appropriate vector, for example, retrovirus vector. These vectors are well known in the art. The polynucleotide or a vector comprising thereof in an expressible form can be introduced into a CD8-positive T cell, for example, a CD8-positive T cell derived from a patient. The present invention provides off-the-shelf compositions that allow rapid and easy production of modified T cells that have superior cancer cell-killing properties by rapid modification of the patient's own T cells (or T cells derived from another subject).

Herein, a specific TCR is a TCR that can confer a specific cytotoxic activity against target cells by specifically recognizing a complex of a peptide of the present invention and an HLA antigen presented on the surface of the target cell when the TCR is present on the surface of a CD8-positive T cell. Specific recognition of the above-described complex can be confirmed by any known method, and preferable examples thereof include HLA multimer staining analysis using HLA molecules and peptides of the present invention and ELISPOT assay methods. Specific TCR-mediated recognition of target cell by T cell introduced with the above-described polynucleotide and signal transduction in the cell can be confirmed by carrying out an ELISPOT assay. When the above-described TCR is present on the surface of a CD8-positive T cell, whether the TCR can confer a target cell-specific cytotoxic activity against the CD8-positive T cell can also be confirmed by known methods. Preferable methods include, for example, measuring the cytotoxic activity against target cells by a chrome release assay method or such.

The present invention provides, in the context of HLA-A33, CTLs prepared by transforming CD8-positive T cells with a polynucleotide encoding each subunit of TCR that binds to, for example, a complex formed by a peptide having the amino acid sequence selected from among SEQ ID NOs: 1, 2, 3, 6, 7, 11, 12, 17, 18, 20, 22, 24, 26, 32, 33, 36, 39, 41, 42, 45 and 46 and an HLA-A33 antigen.

The present invention provides, in the context of HLA-A01, CTLs prepared by transforming CD8-positive T cells with a polynucleotide encoding each subunit of TCR that binds to, for example, a complex formed by a peptide having the amino acid sequence selected from among SEQ ID NOs: 48, 49, 50, 52, 53, 55, 20, 56, 57, 58, 59, 60 and 61 and an HLA-A01 antigen.

The transformed CTLs are capable of homing (translocation of lymphocytes from the blood to lymphatic tissues) in vivo and may be propagated by a well-known in vitro culturing method (for example, Kawakami et al., J Immunol., 1989, 142: 3252-61). The CTLs of the present invention can be used to form an immunogenic composition useful for disease treatment or prevention (prophylaxis) in a patient in need of treatment or prevention (prophylaxis) (the contents are incorporated herein for reference WO2006/031221).

IX. Pharmaceutical Compositions

The present invention further provides compositions or pharmaceutical compositions, comprising at least one active ingredient selected from below:

(a) a peptide of the present invention;
(b) a polynucleotide encoding a peptide of the present invention in an expressible form;
(c) an APC of the present invention;
(d) an exosome of the present invention; and
(e) a CTL of the present invention.

The pharmaceutical compositions of the present invention can comprise as needed a carrier(s), an excipient(s) or such commonly used in pharmaceuticals without particular limitations, in addition to the active ingredient(s) described above. An example of a carrier that can be used in a pharmaceutical composition of the present invention includes sterilized water, physiological saline, phosphate buffer, culture fluid and such. Therefore, the present invention also provides pharmaceutical compositions, comprising at least one active ingredient selected from (a) to (e) below and a pharmaceutically acceptable carrier:

(a) a peptide of the present invention;
(b) a polynucleotide encoding a peptide of the present invention in an expressible form;
(c) an APC of the present invention;
(d) an exosome of the present invention; and
(e) a CTL of the present invention.

Further, the pharmaceutical compositions of the present invention can comprise, as needed, stabilizers, suspensions, preservatives, surfactants, solubilizing agents, pH adjusters, aggregation inhibitors and such.

The FOXM1 expression significantly up-regulates in cancer cells compared with normal tissues. Thus, a peptide of the present invention or a polynucleotide encoding the peptide can be used to treat and/or prevent cancer, and/or prevent postoperative recurrence thereof. Therefore, the present invention provides pharmaceutical compositions for treating and/or preventing cancer, and/or preventing postoperative recurrence thereof, comprising one or more types of peptides or polynucleotides of the present invention as an active ingredient. Alternatively, the peptides of the present invention can be made to be presented on the surface of exosomes or APCs for use as pharmaceutical compositions. In addition, CTLs of the present invention targeting any one of the peptides of the present invention can also be used as an active ingredient of the pharmaceutical compositions of the present invention. The pharmaceutical compositions of the present invention may comprise a therapeutically effective amount or a pharmaceutically effective amount of the above-described active ingredient.

The pharmaceutical compositions of the present invention may also be used as a vaccine. In the context of the present invention, the term "vaccine" (also called "immunogenic composition") refers to a composition that has a function of inducing an immune response that leads to antitumor action when inoculated into an animal. Thus, a pharmaceutical composition of the present invention can be used to induce an immune response that leads to antitumor action in a subject. The immune response induced by a peptide, a polynucleotide, an APC, a CTL and a pharmaceutical composition of the present invention is not particularly limited as long as it is an immune response that leads to antitumor action, and examples include induction of cancer cell-specific CTLs and induction of cancer cell-specific cytotoxic activity.

The pharmaceutical compositions of the present invention can be used to treat and/or prevent cancer, and/or prevent postoperative recurrence thereof in human subjects or patients. The pharmaceutical compositions of the present invention can be used preferably to a subject positive for at least one HLA selected from among HLA-A33 and HLA-A01. Further, the pharmaceutical compositions of the present invention can be used preferably to treat and/or prevent cancers expressing FOXM1 and at least one HLA selected from among HLA-A33 and HLA-A01, and/or prevent postoperative recurrence thereof.

In another embodiment, the present invention provides use of an active ingredient selected from below in the manufacture of a pharmaceutical composition for treating or preventing cancer:

(a) a peptide of the present invention;
(b) a polynucleotide encoding a peptide of the present invention in an expressible form;
(c) an APC that presents a peptide of the present invention on its surface;
(d) an exosome that presents a peptide of the present invention on its surface; and
(e) a CTL of the present invention.

Alternatively, the present invention further provides an active ingredient selected from below for use in treating or preventing cancer:

(a) a peptide of the present invention;
(b) a polynucleotide encoding a peptide of the present invention in an expressible form;
(c) an APC that presents a peptide of the present invention on its surface;
(d) an exosome that presents a peptide of the present invention on its surface; and
(e) a CTL of the present invention.

Alternatively, the present invention further provides a method or process for manufacturing a pharmaceutical composition for treating or preventing cancer, wherein the method or process comprises a step of formulating at least one active ingredient selected from below with a pharmaceutically or physiologically acceptable carrier:

(a) a peptide of the present invention;
(b) a polynucleotide encoding a peptide of the present invention in an expressible form;
(c) an APC that presents a peptide of the present invention on its surface;
(d) an exosome that presents a peptide of the present invention on its surface; and
(e) a CTL of the present invention.

In another embodiment, the present invention further provides a method or process for manufacturing a pharmaceutical composition for treating or preventing cancer, wherein the method or process comprises a step of mixing an active ingredient selected from below with a pharmaceutically or physiologically acceptable carrier:

(a) a peptide of the present invention;
(b) a polynucleotide encoding a peptide of the present invention in an expressible form;
(c) an APC that presents a peptide of the present invention on its surface;
(d) an exosome that presents a peptide of the present invention on its surface; and
(e) a CTL of the present invention.

In another embodiment, the present invention further provides a method for treating or preventing cancer, which comprises a step of administering to a subject at least one active ingredient selected from below:

(a) a peptide of the present invention;
(b) a polynucleotide encoding a peptide of the present invention in an expressible form;
(c) an APC that presents a peptide of the present invention on its surface;
(d) an exosome that presents a peptide of the present invention on its surface; and
(e) a CTL of the present invention.

In the present invention, peptide having the amino acid sequence selected from among SEQ ID NOs: 1, 2, 3, 6, 7, 11, 12, 17, 18, 20, 22, 24, 26, 32, 33, 36, 39, 41, 42, 45 and 46 is identified as HLA-A33-restricted epitope peptide that can induce a potent and specific immune response. Therefore, pharmaceutical compositions of the present invention comprising at least one of peptides having the amino acid sequence selected from among SEQ ID NOs: 1, 2, 3, 6, 7, 11, 12, 17, 18, 20, 22, 24, 26, 32, 33, 36, 39, 41, 42, 45 and 46 are suitable particularly for administration to a subject having HLA-A33 (for example, HLA-A*33:03) as an HLA antigen. The same applies to pharmaceutical compositions comprising a polynucleotide encoding any of these peptides (i.e., polynucleotides of the present invention), an APC or exosome that presents these peptides (i.e., APCs or exosomes of the present invention), or a CTL targeting these peptides (i.e., CTLs of the present invention). That is, pharmaceutical compositions comprising an active ingredient in association with a peptide having the amino acid sequence selected from among SEQ ID NOs: 1, 2, 3, 6, 7, 11, 12, 17, 18, 20, 22, 24, 26, 32, 33, 36, 39, 41, 42, 45 and 46 are suitable for administration to subjects having HLA-A33 (i.e., HLA-A33-positive subjects). In a more preferred embodiment, the pharmaceutical composition of the present invention is a pharmaceutical composition that comprises a peptide having the amino acid sequence of SEQ ID NO: 2.

Similarly, in the present invention, peptides having the amino acid sequence selected from among SEQ ID NOs: 48, 49, 50, 52, 53, 55, 20, 56, 57, 58, 59, 60 and 61 are identified as HLA-A01-restricted epitope peptides that can induce a potent and specific immune response. Therefore, pharmaceutical compositions of the present invention comprising at least one of peptides having the amino acid sequence selected from among SEQ ID NOs: 48, 49, 50, 52, 53, 55, 20, 56, 57, 58, 59, 60 and 61 are suitable particularly for administration to a subject having HLA-A01 (for example, HLA-A*01:01) as an HLA antigen. The same applies to pharmaceutical compositions comprising a polynucleotide encoding any of these peptides (i.e., polynucleotides of the present invention), an APC or exosome that presents these peptides (i.e., APCs or exosomes of the present invention), or a CTL targeting these peptides (i.e., CTLs of the present invention). That is, pharmaceutical compositions comprising an active ingredient in association with a peptide having the amino acid sequence selected from among SEQ ID NOs: 48, 49, 50, 52, 53, 55, 20, 56, 57, 58, 59, 60 and 61 are suitable for administration to subjects having HLA-A01 (i.e., HLA-A01-positive subjects). In a more preferred embodiment, the pharmaceutical composition of the present invention is a pharmaceutical composition that comprises a peptide having the amino acid sequence of SEQ ID NO: 56.

Cancers to be treated and/or prevented by pharmaceutical compositions of the present invention are not particularly limited as long as they are cancers that express FOXM1, and include various cancers, for example, acute myeloid leukemia (AML), bladder cancer, breast cancer, cervical cancer, cholangiocellular cancer, chronic myeloid leukemia (CML), colon cancer, esophageal cancer, gastric cancer, diffuse gastric cancer, liver cancer, non-small-cell lung cancer (NSCLC), lymphoma, osteosarcoma, ovary cancer, pancreatic cancer, prostate cancer, kidney cancer, small-cell lung cancer (SCLC), soft tissue tumor, testicular tumor and such. Furthermore, the pharmaceutical compositions of the present invention can preferably be used for subjects that homozygously or heterozygously have an HLA allele selected from among HLA-A33 and HLA-A01.

In addition to the active ingredients described above, the pharmaceutical compositions of the present invention can comprise the other peptides that have the ability to induce CTLs against cancer cells (for example, the other TAA-derived CTL-inducing peptides), the other polynucleotides encoding the other peptides, the other cells that present the other peptides, or such.

The pharmaceutical compositions of the present invention may also optionally comprise the other therapeutic substances as an active ingredient, as long as they do not inhibit the anti-tumor effects of the above-described active ingredients such as peptides of the present invention. For example, the pharmaceutical compositions of the present invention may optionally comprise anti-inflammatory compositions, analgesics, chemotherapeutics and the like. In addition to including the other therapeutic substances to a pharmaceutical composition of the present invention itself, one can also administer the pharmaceutical composition of the present invention sequentially or concurrently with one or more other pharmaceutical compositions. The dose of the pharmaceutical composition of the present invention and the other pharmaceutical compositions depend on, for example, the type of pharmaceutical composition used and the disease being treated, as well as the scheduling and routes of administration.

It should be understood that in consideration of the formulation type, the pharmaceutical composition of the present invention may include other components conventional in the art, in addition to the ingredients specifically mentioned herein.

The present invention also provides articles of manufacture or kits that comprise a pharmaceutical composition of the present invention. The articles of manufacture or kits of the present invention can include a container that houses the pharmaceutical composition of the present invention. An example of an appropriate container includes a bottle, a vial or a test tube, but is not limited thereto. The container may be formed of various materials such as glass or plastic. A label may be attached to the container, and the disease or disease state to which the pharmaceutical composition of the present invention should be used may be described in the label. The label may also indicate directions for administration and such.

The articles of manufacture or kits of the present invention may further comprise a second container that houses pharmaceutically acceptable diluents optionally, in addition to the container that houses the pharmaceutical composition of the present invention. The articles of manufacture or kits of the present invention may further comprise the other materials desirable from a commercial standpoint and the user's perspective, such as the other buffers, diluents, filters, injection needles, syringes, and package inserts with instructions for use.

As needed, the pharmaceutical composition of the present invention can be provided in a pack or dispenser device that can contain one or more units of dosage forms containing active ingredients. The pack can include, for example, a metallic foil or a plastic foil such as a blister pack. Instructions for administration can be attached to the pack or dispenser device.

(1) Pharmaceutical Compositions Comprising Peptide(s) as an Active Ingredient

The pharmaceutical composition comprising a peptide of the present invention can be formulated by conventional formulation methods as needed. The pharmaceutical compositions of the present invention may comprise as needed in addition to the peptide of the present invention, carriers, excipients and such commonly used in pharmaceuticals without particular limitations. Examples of carriers that can be used in pharmaceutical compositions of the present invention include sterilized water (for example, water for injection), physiological saline, phosphate buffer, phosphate buffered saline, Tris buffered saline, 0.3% glycine, culture fluid, and such. Further, the pharmaceutical compositions of the present invention may comprise as needed stabilizers, suspensions, preservatives, surfactants, solubilizing agents, pH adjusters, aggregation inhibitors, and such. The pharmaceutical compositions of the present invention can induce specific immunity against FOXM1-expressing cancer cells, and thus can be applied for the purpose of cancer treatment or prevention (prophylaxis).

For example, the pharmaceutical compositions of the present invention can be prepared by dissolving in pharmaceutically or physiologically acceptable water-soluble carriers such as sterilized water (for example, water for injection), physiological saline, phosphate buffer, phosphate buffered saline, and Tris buffered saline and adding, as needed, stabilizers, suspensions, preservatives, surfactants, solubilizing agents, pH adjusters, aggregation inhibitors and such, and then sterilizing the peptide solution. The method of sterilizing a peptide solution is not particularly limited, and is preferably carried out by filtration sterilization. Filtration sterilization can be performed using, for example, a filtration sterilization filter of 0.22 micro-m or less in pore diameter. The filtration-sterilized peptide solution can be administered to a subject, for example, as an injection, without being limited thereto.

The pharmaceutical compositions of the present invention may be prepared as a freeze-dried formulation by freeze-drying the above-described peptide solution. The freeze-dried formulation can be prepared by filling the peptide solution prepared as described above into an appropriate container such as an ampule, a vial or a plastic container, followed by freeze drying and encapsulation into the container with a wash-sterilized rubber plug or such after pressure recovery. The freeze-dried formulation can be administered to a subject after it is re-dissolved in pharmaceutically or physiologically acceptable water-soluble carriers such as sterilized water (for example, water for injection), physiological saline, phosphate buffer, phosphate buffered saline, Tris buffered saline and such before administration. Preferred examples of pharmaceutical compositions of the present invention include injections of such a filtration-sterilized peptide solution, and freeze-dried formulations that result from freeze-drying the peptide solution. The present invention further encompasses kits comprising such a freeze-dried formulation and re-dissolving solution. The present invention also encompasses kits comprising a container that houses the freeze-dried formulation, which is a pharmaceutical composition of the present invention, and a container that houses a re-dissolving solution thereof.

The pharmaceutical compositions of the present invention can comprise a combination of two or more types of the peptides of the present invention. The combination of peptides can take a cocktail form of mixed peptides, or can be conjugated with each other using standard techniques. For example, peptides can be chemically linked or expressed as single fusion polypeptide sequences. By administering a peptide of the present invention, the peptide is presented on APCs by an HLA antigen at a high density, and then subsequently CTLs that react specifically to a complex formed between the presented peptide and the HLA antigen are induced. Alternatively, APCs (for example, DCs) are removed from a subject, and subsequently stimulated with peptides of the present invention to obtain APCs that present any of the peptides of the present invention on their cell surface. These APCs are re-administered to a subject to induce CTLs in the subject, and as a result, the aggressiveness towards FOXM1-expressing cancer cells can be increased.

The pharmaceutical compositions of the present invention may also comprise an adjuvant known for effectively establishing cellular immunity. An adjuvant refers to a compound that enhances the immune response against an antigen that has immunological activity when administered together (or successively) with the antigen. Known adjuvants described in literatures, for example, Clin Microbiol Rev 1994, 7: 277-89, can be used. Examples of a suitable adjuvant include aluminum salts (aluminum phosphate, aluminum hydroxide, aluminum oxyhydroxide and such), alum, cholera toxin, *Salmonella* toxin, Incomplete Freund's adjuvant (IFA), Complete Freund's adjuvant (CFA), ISCOMatrix, GM-CSF and other immunostimulatory cytokines, oligodeoxynucleotide containing the CpG motif (CpG7909 and such), oil-in-water emulsions, Saponin or its derivatives (QS21 and such), lipopolysaccharide such as Lipid A or its derivatives (MPL, RC529, GLA, E6020 and such), lipopeptides, lactoferrin, flagellin, double-stranded RNA or its derivatives (poli IC and such), bacterial DNA, imidazoquinolines (Imiquimod, R848 and such), C-type lectin ligand (trehalose-6,6'-dibehenate (TDB) and such), CD1d ligand (alpha-galactosylceramide and such), squalene emulsions (MF59, AS03, AF03 and such), PLGA, and such, without being limited thereto. The adjuvant may be contained in another container separate from the pharmaceutical composition comprising a peptide of the present invention in the kits comprising the pharmaceutical composition of the present invention. In this case, the adjuvant and the pharmaceutical composition may be administered to a subject in succession, or mixed together immediately before administration to a subject. Such kits comprising a pharmaceutical composition comprising a peptide of the present invention and an adjuvant are also provided by the present invention. When the pharmaceutical composition of the present invention is a freeze-dried formulation, the kit can further comprise a re-dissolving solution. Further, the present invention provides kits comprising a container that houses a pharmaceutical composition of the present invention and a container that stores an adjuvant. The kit can further comprise as needed a container that stores the re-dissolving solution.

When an oil adjuvant is used as an adjuvant, the pharmaceutical composition of the present invention may be prepared as an emulsion. Emulsions can be prepared, for example, by mixing and stirring the peptide solution prepared as described above and an oil adjuvant. The peptide solution may be one that has been re-dissolved after freeze-drying. The emulsion may be either of the W/O-type emulsion and O/W-type emulsion, and the W/O-type emulsion is preferred for obtaining a high immune response-enhancing effect. IFA can be preferably used as an oil adjuvant, without being limited thereto. Preparation of an emulsion can be carried out immediately before administration to a subject, and in this case, the pharmaceutical composition of the present invention may be provided as a kit comprising the peptide solution of the present invention and an oil adjuvant. When the pharmaceutical composition of the present invention is a freeze-dried formulation, the kit can further comprise a re-dissolving solution.

Further, the pharmaceutical composition of the present invention may be a liposome formulation within which a peptide of the present invention is encapsulated, a granular formulation in which a peptide is bound to beads with several micrometers in diameter, or a formulation in which a lipid is bound to a peptide.

In another embodiment of the present invention, the peptide of the present invention may also be administered in the form of a pharmaceutically acceptable salt. Preferred examples of salts include salts with alkali metals (lithium, potassium, sodium and such), salts with alkaline-earth metals (calcium, magnesium and such), salts with other metals (copper, iron, zinc, manganese and such), salts with organic bases, salts with amines, salts with organic acids (acetic acid, formic acid, propionic acid, fumaric acid, maleic acid, succinic acid, tartaric acid, citric acid, malic acid, oxalic acid, benzoic acid, methanesulfonic acid and such), and salts with inorganic acids (hydrochloric acid, phosphoric acid, hydrobromic acid, sulfuric acid, nitric acid and such). The phrase "pharmaceutically acceptable salt" used herein refers to a salt that retains the pharmacological and pharmaceutical efficacy and property of the compound. Therefore, pharmaceutical compositions comprising a pharmaceutically acceptable salt of a peptide of the present invention are also encompassed by the present invention. Further, the "peptide of the present invention" also encompasses, in addition to the free peptide, pharmaceutically acceptable salts thereof.

In some embodiments, the pharmaceutical compositions of the present invention may further include a component which primes CTLs. Lipids have been identified as substances capable of priming CTLs in vivo against viral antigens. For example, palmitic acid residues can be attached to the epsilon- and alpha-amino groups of a lysine residue and then linked to a peptide of the present invention. The lipidated peptide can then be administered either directly in a micelle or particle, incorporated into a liposome, or emulsified in an adjuvant. As another example of lipid priming of CTL responses, *E. coli* lipoproteins, such as tripalmitoyl-S-glycerylcysteinyl-seryl-serine (P3CSS) can be used to prime CTLs when covalently attached to an appropriate peptide (see, e.g., Deres et al., Nature 1989, 342: 561-4).

Examples of suitable methods for administering the peptides or pharmaceutical compositions of the present invention include oral, epidermal, subcutaneous, intramuscular, intraosseous, peritoneal, and intravenous injections, as well as systemic administration or local administration to the vicinity of the targeted sites, but are not limited thereto. A preferred administration method includes subcutaneous injection to the vicinity of lymph nodes such as the armpit or groin. More specifically, for example, subcutaneous administration is preferred when the pharmaceutical composition of the present invention comprises a peptide or exosome as an active ingredient. Alternatively, compositions having APCs or CTLs as an active ingredient can be administered by intravenous injection or such. The administration can be performed by single administration or boosted by multiple administrations.

The peptides of the present invention can be administered to a subject in a therapeutically or pharmaceutically effective amount for treating cancer or in a therapeutically or pharmaceutically effective amount for inducing immunity (more specifically CTLs) against FOXM1-expressing cancer cells. The dose of the peptides of the present invention can be appropriately adjusted according to the disease to be treated, the patient's age and weight, the method of administration and such. For each of the peptides of the present invention, the dose is usually 0.001 mg-1000 mg, for example, 0.01 mg-100 mg, for example, 0.1 mg-30 mg, for example, 0.1 mg-10 mg, for example, 0.5 mg-5 mg. The dosing interval can be once every several days to several months, and for example, the dosing can be done in a once-per-week interval. A skilled artisan can appropriately select a suitable dose (dosage).

In a preferred embodiment, the pharmaceutical compositions of the present invention comprise a therapeutically effective amount of a peptide of the present invention and a pharmaceutically or physiologically acceptable carrier. In another embodiment, the pharmaceutical compositions of the present invention comprise a therapeutically effective amount of a peptide of the present invention, a pharmaceutically or physiologically acceptable carrier, and an adjuvant. The pharmaceutical compositions of the present invention can comprise 0.001 mg-1000 mg, preferably 0.01 mg-100 mg, more preferably 0.1 mg-30 mg, even more preferably 0.1 mg-10 mg, for example, 0.5 mg-5 mg of a peptide of the present invention. When a pharmaceutical composition of the present invention is an injection, it can comprise a peptide of the present invention at a concentration of 0.001 mg/ml-1000 mg/ml, preferably 0.01 mg/ml-100 mg/ml, more preferably 0.1 mg/ml-30 mg/ml, even more preferably 0.1 mg/ml-10 mg/ml, for example, 0.5 mg/ml-5 mg/ml. In this case, for example, 0.1 to 5 ml, preferably 0.5 ml to 2 ml of the pharmaceutical composition of the present invention can be administered to a subject by injection.

Further, the present invention provides methods of treating and/or preventing cancer and/or preventing postoperative recurrence thereof, which comprise administering to a subject a therapeutically effective amount of a peptide of the present invention or a pharmaceutical composition of the present invention. As described above, the peptides of the present invention can be administered to a subject in a single dose of usually 0.001 mg-1000 mg, for example, 0.01 mg-100 mg, for example, 0.1 mg-30 mg, for example, 0.1 mg-10 mg, or for example, 0.5 mg-5 mg. In a preferred embodiment, the peptides of the present invention are administered to a subject together with an adjuvant. Further, the dosing interval can be once every several days to several months, preferably once every several days to every month, for example, once every week or once every two weeks.

(2) Pharmaceutical Compositions Containing Polynucleotides as the Active Ingredient The pharmaceutical compositions of the present invention can also contain polynucleotides encoding the peptides of the present invention in an expressible form. Herein, the phrase "in an expressible form" means that the polynucleotide, when introduced into a cell, will be expressed as a peptide of the present invention. In an exemplified embodiment, the sequence of the polynucleotide of the present invention includes regulatory elements necessary for expression of the peptide of the present invention. The polynucleotide(s) of the present invention can be equipped with a sequence necessary to achieve stable insertion into the genome of the target cell (see, e.g., Thomas K R & Capecchi M R, Cell 1987, 51: 503-12 for a description of homologous recombination cassette vectors). See, e.g., Wolff et al., Science 1990, 247: 1465-8; U.S. Pat. Nos. 5,580,859, 5,589,466, 5,804,566, 5,739,118, 5,736,524, 5,679,647; and WO98/04720. Examples of DNA-based delivery technologies include "naked DNA", facilitated (bupivacaine, polymers, peptide-mediated) delivery, cationic lipid complexes, and particle-mediated ("gene gun") or pressure-mediated delivery (see, e.g., U.S. Pat. No. 5,922,687).

The peptides of the present invention can also be expressed by viral or bacterial vectors. Examples of expression vectors include attenuated viral hosts, such as vaccinia or fowlpox. For example, as a vector to express the peptide of the present invention, vaccinia virus can be used. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover et al., Nature 1991, 351: 456-60. A wide variety of other vectors useful for therapeutic administration or immunization, e.g., adeno and adeno-associated virus vectors, retroviral vectors, *Salmonella typhi* vectors, detoxified anthrax toxin vectors, and the like, will be apparent. See, e.g., Shata et al., Mol Med Today 2000, 6: 66-71; Shedlock et al., J Leukoc Biol 2000, 68: 793-806; Hipp et al., In Vivo 2000, 14: 571-85.

Delivery of a polynucleotide of the present invention into a patient can be either direct, in which case the patient can be directly exposed to a vector harboring the polynucleotide of the present invention, or indirect, in which case, cells are first transformed with the vector harboring the polynucleotide of the present invention in vitro, then the cells are transplanted into the patient. These two approaches are known, respectively, as in vivo and ex vivo gene therapies.

For general reviews of the methods of gene therapy, see Goldspiel et al., Clinical Pharmacy 1993, 12: 488-505; Wu and Wu, Biotherapy 1991, 3: 87-95; Tolstoshev, Ann Rev Pharmacol Toxicol 1993, 33: 573-96; Mulligan, Science 1993, 260: 926-32; Morgan & Anderson, Ann Rev Biochem 1993, 62: 191-217; Trends in Biotechnology 1993, 11(5): 155-215. Methods commonly known in the art of recombinant DNA technology which can also be used for the present invention are described in Ausubel et al., Current Protocols in Molecular Biology, John Wiley & Sons, N Y, 1993; and Krieger, Gene Transfer and Expression, A Laboratory Manual, Stockton Press, N Y, 1990.

Similar to peptide administration, administration of polynucleotides may be performed by oral, intradermal, subcutaneous, intravenous, intramuscular, intraosseous and/or peritoneal injection, and such. Administration of polynucleotides can be a systemic administration or a local administration to the vicinity of the targeted sites. The administration can be performed by single administration or boosted by multiple administrations. The polynucleotides of the present invention can be administered to a subject in a therapeutically or pharmaceutically effective dose for inducing immunity (more specifically CTLs) against FOXM1-expressing cancer cells, or in a therapeutically or pharmaceutically effective dose for treating cancer. The dose of a polynucleotide in a suitable carrier or the dose of a polynucleotide in cells transformed with a polynucleotide encoding a peptide of the present invention can be appropriately adjusted according to the disease to be treated, the patient's age and weight, the method of administration and such, and this may be usually 0.001 mg-1000 mg, for example, 0.01 mg-100 mg, for example, 0.1 mg-30 mg, for example, 0.1 mg-10 mg, or for example, 0.5 mg-5 mg. The dosing interval can be once every several days to several months, and for example, the dosing can be done in a once-per-week interval. A skilled artisan can appropriately select a suitable dose (dosage).

X. Methods of Using Peptides, Exosomes, APCs and CTLs

The peptides and polynucleotides of the present invention can be used to induce APCs and CTLs. CTLs can also be induced using the exosomes and APCs of the present invention. The peptides, polynucleotides, exosomes, and APCs of the present invention can be used in combination with any other compound(s) as long as their CTL-inducing ability is not inhibited. Therefore, CTLs of the present invention can be induced using a pharmaceutical composition comprising any of the peptides, polynucleotides, APCs and exosomes of the present invention. Further, APCs of the present invention can be induced using a pharmaceutical composition comprising a peptide or polynucleotide of the present invention.

(1) Methods of Inducing APCs

The present invention provides methods of inducing APCs having CTL-inducing ability, using a peptide(s) or polynucleotide(s) of the present invention.

The methods of the present invention comprise a step of contacting an APC with a peptide of the present invention in vitro, ex vivo, or in vivo. For example, a method of contacting APCs with the peptide ex vivo may comprise the steps below:

(a) collecting APCs from a subject; and (b) contacting the APCs of step (a) with a peptide of the present invention.

The above-described APCs are not limited to a particular type of cell, and DCs, Langerhans cells, macrophages, B cells, and activated T cells, which are known to present a proteinaceous antigen on their cell surface to be recognized by lymphocytes, can be used. DCs have the most potent CTL-inducing ability among APCs, and thus it is preferable to use DCs. Any peptides of the present invention can be used by themselves or in combination with other peptides of the present invention. Further, peptides of the present invention can be used in combination with other CTL-inducing peptides (for example, other TAA-derived CTL-inducing peptides).

Meanwhile, when a peptide of the present invention is administered to a subject, APCs are contacted with the peptide in vivo, and as a result, APCs having a high CTL-inducing ability are induced in the body of the subject. Therefore, the methods of the present invention may comprise a step of administering a peptide of the present invention to a subject. Similarly, when a polynucleotide of the present invention is administered to a subject in an expressible form, a peptide of the present invention is expressed in vivo, the expressed peptide is contacted with APCs in vivo, and as a result APCs having a high CTL-inducing ability are induced in the body of the subject. Therefore, the present invention may also comprise a step of administering a polynucleotide of the present invention to a subject.

In order to induce APCs having CTL-inducing ability, the present invention may comprise a step of introducing a polynucleotide of the present invention into APCs. For example, the method may comprise the steps below:

(a) collecting APCs from a subject; and (b) introducing a polynucleotide encoding a peptide of the present invention into the APCs of step (a).

Step (b) can be performed as described in the above "VI. Antigen-presenting cells (APCs)" section.

Thus, in one embodiment, the present invention provides a method of inducing APCs having CTL-inducing ability, which comprises the step (a) or (b) below:

(a) contacting APCs with a peptide of the present invention; and (b) introducing a polynucleotide encoding a peptide of the present invention into APCs.

Furthermore, the present invention provides a method of preparing APCs having CTL-inducing ability, which comprises the step (a) or (b) below:

(a) contacting APCs with a peptide of the present invention; or (b) introducing a polynucleotide encoding a peptide of the present invention into APCs.

The above-described methods can be performed in vitro, ex vivo, or in vivo, and it is preferable to perform them in vitro or ex vivo. APCs used in the above-described methods may be derived from a subject scheduled for administration of the induced APCs, or they may be derived from a different subject. When APCs derived from a subject (donor) different from the subject scheduled for administration are used, the subject of administration and the donor must have the identical HLA type.

In the methods of the present invention, when a peptide having the amino acid sequence selected from among SEQ ID NOs: 1, 2, 3, 6, 7, 11, 12, 17, 18, 20, 22, 24, 26, 32, 33, 36, 39, 41, 42, 45 and 46 or a modified peptide thereof is used as a peptide of the present invention, the HLA is preferably HLA-A33 (more preferably HLA-A*33:03) in both the subject of administration and the donor. Alternatively, APCs used in the above-described methods are preferably APCs that express HLA-A33 (more preferably HLA-A*33:03).

Similarly, when a peptide having the amino acid sequence selected from among SEQ ID NOs: 48, 49, 50, 52, 53, 55, 20, 56, 57, 58, 59, 60 and 61 or a modified peptide thereof is used as a peptide of the present invention, the HLA is preferably HLA-A01 (more preferably HLA-A*01:01) in both the subject of administration and the donor. Alternatively, APCs used in the above-described methods are preferably APCs that express HLA-A01 (more preferably HLA-A*01:01). The APCs can be prepared using known methods from PBMCs after PBMCs are separated from blood collected from a donor by a specific gravity centrifugal method or such.

In another embodiment, the present invention also provides pharmaceutical compositions that comprise a peptide of the present invention or a polynucleotide encoding the peptide for inducing an APC(s) having CTL-inducing ability.

Alternatively, the present invention further provides use of a peptide of the present invention or a polynucleotide encoding the peptide in the manufacture of a pharmaceutical composition for inducing an APC(s) having CTL-inducing ability.

Alternatively, the present invention further provides peptides of the present invention or polynucleotides encoding the peptides for use in the induction of an APC(s) having CTL-inducing ability.

Alternatively, the present invention further provides methods or processes of manufacturing a pharmaceutical composition for inducing an APC(s), wherein the method or process comprises a step of formulating a peptide of the present invention or a polynucleotide encoding the peptide with a pharmaceutically or physiologically acceptable carrier.

In another embodiment, the present invention further provides methods or processes of manufacturing a pharmaceutical composition for inducing an APC(s) having CTL-inducing ability, wherein the method or process comprises a step of mixing a peptide of the present invention or a polynucleotide encoding the peptide with a pharmaceutically or physiologically acceptable carrier.

APCs induced by the methods of the present invention can induce CTLs specific to FOXM1 (i.e., CTLs of the present invention).

(2) Methods of Inducing CTLs

The present invention also provides methods of inducing CTLs using peptides, polynucleotides, exosomes or APCs of the present invention. The present invention further provides methods of inducing CTLs using one or more polynucleotides encoding a polypeptide(s) that can form a T cell receptor (TCR) (i.e., TCR subunit) capable of recognizing a complex of a peptide of present invention and an HLA antigen. Preferably, the methods of inducing CTLs comprise at least one steps selected from below:

(a) contacting CD8-positive T cells with antigen-presenting cells that present on their surface a complex of an HLA antigen and a peptide of present invention;
(b) contacting CD8-positive T cells with exosomes that present on its surface a complex of an HLA antigen and a peptide of present invention; and
(c) introducing into CD8-positive T cells one or more polynucleotides encoding a polypeptide(s) that can form a TCR capable of recognizing a complex of a peptide of present invention and an HLA antigen.

When a peptide(s), a polynucleotide(s), an exosome(s) or an APC(s) of the present invention is administered to a subject, CTLs are induced in the body of the subject and the strength of the immune response targeting FOXM1-expressing cancer cells is enhanced. Therefore, the methods of the present invention may comprise a step of administering a peptide(s), a polynucleotide(s), an APC(s) or an exosome(s) of the present invention to a subject.

Alternatively, CTLs can be induced by using them in vitro or ex vivo. For example, the methods of the present invention may include the following steps:

(a) collecting APCs from a subject;
(b) contacting the APCs of step (a) with a peptide of the present invention; and
(c) co-culturing the APCs of step (b) with CD8-positive T cells.

The induced CTLs may be returned to the subject afterwards.

The APCs to be co-cultured with the CD8-positive T cells in step (c) above can also be prepared by introducing into APCs a polynucleotide encoding a peptide of the present invention as described above in the "VI. Antigen-presenting cells (APCs)" section. However, the APCs to be used in the methods of the present invention are not limited thereto, and any APCs that present on their surface a complex of an HLA antigen and a peptide of the present invention can be used.

In the methods of the present invention, instead of such APCs, exosomes that present on their surface a complex of an HLA antigen and a peptide of the present invention can also be used. That is, the methods of the present invention can comprise a step of co-culturing with exosomes that present on their surface a complex of an HLA antigen and a peptide of the present invention. Such exosomes can be prepared by the above-described methods in the "V. Exosomes" section.

Further, CTLs can also be induced by introducing into a CD8-positive T cell a vector comprising a polynucleotide encoding each subunit of a TCR capable of binding to a peptide of the present invention presented by an HLA antigen on the cell surface. Such transformation can be carried out as described above in the "VIII. T cell receptors (TCRs)" section.

Accordingly, in one embodiment, the present invention provides methods of inducing CTLs, comprising a step selected from below:

(a) co-culturing CD8-positive T cells with APCs that present on their surface a complex of an HLA antigen and a peptide of present invention;
(b) co-culturing CD8-positive T cells with exosomes that present on their surface a complex of an HLA antigen and a peptide of present invention; and
(c) introducing into CD8-positive T cells, a vector comprising a polynucleotide encoding each subunit of a TCR capable of binding to a peptide of the present invention presented by an HLA antigen on a cell surface.

The above-described methods can be performed in vitro, ex vivo, or in vivo, and it is preferable to perform them in vitro or ex vivo. APCs or exosomes and CD8-positive T cells used in the above-described methods may be derived from a subject scheduled for administration of the induced CTLs, or they may be derived from a different subject. When APCs or exosomes and CD8-positive T cells derived from a subject (donor) different from the subject scheduled for administration are used, the subject of administration and the donor must have the identical HLA type. For example, when a peptide having the amino acid sequence selected from among SEQ ID NOs: 1, 2, 3, 6, 7, 11, 12, 17, 18, 20, 22, 24, 26, 32, 33, 36, 39, 41, 42, 45 and 46 or a modified peptide thereof is used as peptides of the present invention, the HLA in both the subject of administration and the donor is preferably HLA-A33 (more preferably HLA-A*33:03). Alternatively, APCs or exosomes used in the above-described methods are preferably APCs or exosomes that present on their surface a complex of HLA-A33 (more preferably HLA-A*33:03) and a peptide of the present invention (a peptide having the amino acid sequence selected from among SEQ ID NOs: 1, 2, 3, 6, 7, 11, 12, 17, 18, 20, 22, 24, 26, 32, 33, 36, 39, 41, 42, 45 and 46 or a modified peptide thereof). In this case, the induced CTLs show a specific cytotoxic activity against cells that present a complex of HLA-A33 and a peptide of the present invention (for example, FOXM1-expressing HLA-A33-positive cells).

Alternatively, for example, when a peptide having the amino acid sequence selected from among SEQ ID NOs: 48, 49, 50, 52, 53, 55, 20, 56, 57, 58, 59, 60 and 61 or a modified peptide thereof is used as peptides of the present invention, the HLA in both the subject of administration and the donor is preferably HLA-A01 (more preferably HLA-A*01:01). Alternatively, APCs or exosomes used in the above-described methods are preferably APCs or exosomes that present on their surface a complex of HLA-A01 (more preferably HLA-A*01:01) and a peptide of the present invention (a peptide having the amino acid sequence selected from among SEQ ID NOs: 48, 49, 50, 52, 53, 55, 20, 56, 57, 58, 59, 60 and 61 or a modified peptide thereof). In this case, the induced CTLs show a specific cytotoxic activity against cells that present a complex of HLA-A01 and a peptide of the present invention (for example, FOXM1-expressing HLA-A01-positive cells).

In another embodiment, the present invention also provides compositions or pharmaceutical compositions for inducing CTLs, comprising at least one active ingredient selected from below:

(a) a peptide of the present invention;
(b) a polynucleotide encoding a peptide of the present invention in an expressible form;
(c) an APC that presents on its surface a peptide of the present invention; and
(d) an exosome that presents on its surface a peptide of the present invention.

In another embodiment, the present invention also provides use of an active ingredient selected from below in the manufacture of compositions or pharmaceutical compositions for inducing CTLs:

(a) a peptide of the present invention;
(b) a polynucleotide encoding a peptide of the present invention in an expressible form;
(c) an APC that presents on its surface a peptide of the present invention; and
(d) an exosome that presents on its surface a peptide of the present invention.

Alternatively, the present invention further provides an active ingredient selected from below for use in inducing CTLs:

(a) a peptide of the present invention;
(b) a polynucleotide encoding a peptide of the present invention in an expressible form;
(c) an APC that presents on its surface a peptide of the present invention; and
(d) an exosome that presents on its surface a peptide of the present invention.

Alternatively, the present invention further provides a method or process for manufacturing a composition or pharmaceutical composition for inducing CTLs, which is a method or process that comprises a step of formulating an active ingredient selected from below with a pharmaceutically or physiologically acceptable carrier:

(a) a peptide of the present invention;
(b) a polynucleotide encoding a peptide of the present invention in an expressible form;
(c) an APC that presents on its surface a peptide of the present invention; and
(d) an exosome that presents on its surface a peptide of the present invention.

In another embodiment, the present invention further provides a method or process for manufacturing a composition or pharmaceutical composition for inducing CTLs, which is a method or process that comprises a step of mixing an active ingredient selected from below with a pharmaceutically or physiologically acceptable carrier:

(a) a peptide of the present invention;
(b) a polynucleotide encoding a peptide of the present invention in an expressible form;
(c) an APC that presents on its surface a peptide of the present invention; and
(d) an exosome that presents on its surface a peptide of the present invention.

XI. Methods of Inducing an Immune Response

The present invention further provides methods of inducing an immune response against FOXM1-expressing cancers. Applicable cancers include acute myeloid leukemia (AML), bladder cancer, breast cancer, cervical cancer, cholangiocellular cancer, chronic myeloid leukemia (CML), colon cancer, esophageal cancer, gastric cancer, diffuse gastric cancer, liver cancer, non-small-cell lung cancer (NSCLC), lymphoma, osteosarcoma, ovary cancer, pancreatic cancer, prostate cancer, kidney cancer, small-cell lung cancer (SCLC), soft tissue tumor, testicular tumor and such, but are not limited thereto. It is preferable that the cancer expresses at least one HLA selected from among HLA-A33 and HLA-A01.

The present invention further provides methods of inducing an immune response against FOXM1-expressing cancer cells. FOXM1 is recognized to be overexpressed in various types of cancers described above. Thus, when an immune response against FOXM1-expressing cancer cells is induced, proliferation of the cancer cells is inhibited as a result. Accordingly, the present invention further provides methods of inhibiting proliferation of FOXM1-expressing cancer cells. The methods of the present invention are suitable, in particular, for inhibiting proliferation of cancer cells expressing FOXM1 and at least one HLA selected from among HLA-A33 and HLA-A01.

The methods of the present invention may comprise a step of administering a composition comprising any of the peptides of the present invention or a polynucleotide(s) encoding the peptide(s). The methods of the present invention also contemplate administration of APCs or exosomes presenting any of the peptides of the present invention. The details can be referred to the "IX. Pharmaceutical compositions" section, particularly portions describing regarding use of the pharmaceutical compositions of the present invention as vaccines. In addition, exosomes and APCs that can be used in the methods of the present invention for inducing an immune response are described in detail in "V. Exosomes", "VI. Antigen-presenting cells (APCs)" and in Items (1) and (2) of "X. Methods of using peptides, exosomes, APCs and CTLs" described above.

In another embodiment, the present invention provides pharmaceutical compositions or vaccines for inducing an immune response against FOXM1-expressing cancers, wherein the pharmaceutical composition or vaccine comprises an active ingredient selected from below:

(a) a peptide of the present invention;
(b) a polynucleotide encoding a peptide of the present invention in an expressible form;
(c) an APC that presents on its surface a peptide of the present invention;
(d) an exosome that presents on its surface a peptide of the present invention; and
(e) a CTL of the present invention.

Alternatively, the present invention also provides pharmaceutical compositions or vaccines for inducing an immune response against FOXM1-expressing cancer cells, wherein the pharmaceutical composition or vaccine comprises an active ingredient selected from below:

(a) a peptide of the present invention;
(b) a polynucleotide encoding a peptide of the present invention in an expressible form;
(c) an APC that presents on its surface a peptide of the present invention;
(d) an exosome that presents on its surface a peptide of the present invention; and
(e) a CTL of the present invention.

Alternatively, the present invention further provides pharmaceutical compositions or vaccines for inhibiting proliferation of FOXM1-expressing cancer cells, wherein the pharmaceutical composition or vaccine comprises an active ingredient selected from below:
(a) a peptide of the present invention;
(b) a polynucleotide encoding a peptide of the present invention in an expressible form;
(c) an APC that presents on its surface a peptide of the present invention;
(d) an exosome that presents on its surface a peptide of the present invention; and
(e) a CTL of the present invention.

In another embodiment, the present invention provides use of an active ingredient selected from below in the manufacture of pharmaceutical compositions or vaccines for inducing an immune response against FOXM1-expressing cancers:
(a) a peptide of the present invention;
(b) a polynucleotide encoding a peptide of the present invention in an expressible form;
(c) an APC that presents on its surface a peptide of the present invention;
(d) an exosome that presents on its surface a peptide of the present invention; and
(e) a CTL of the present invention.

Alternatively, the present invention also provides use of an active ingredient selected from below in the manufacture of pharmaceutical compositions or vaccines for inducing an immune response against FOXM1-expressing cancer cells:
(a) a peptide of the present invention;
(b) a polynucleotide encoding a peptide of the present invention in an expressible form;
(c) an APC that presents on its surface a peptide of the present invention;
(d) an exosome that presents on its surface a peptide of the present invention; and
(e) a CTL of the present invention.

Alternatively, the present invention further provides use of an active ingredient selected from below in the manufacture of pharmaceutical compositions or vaccines for inhibiting proliferation of FOXM1-expressing cancer cells:
(a) a peptide of the present invention;
(b) a polynucleotide encoding a peptide of the present invention in an expressible form;
(c) an APC that presents on its surface a peptide of the present invention;
(d) an exosome that presents on its surface a peptide of the present invention; and
(e) a CTL of the present invention.

The present invention further provides methods or processes for manufacturing pharmaceutical compositions that induce an immune response against FOXM1-expressing cancers, which is a method that may comprise a step of mixing or formulating a peptide or polynucleotide of the present invention with a pharmaceutically acceptable carrier.

Alternatively, the present invention provides methods for inhibiting proliferation of FOXM1-expressing cancer cells or methods of inducing an immune response against cancers, which comprises a step of administering to a subject vaccines or pharmaceutical compositions comprising an active ingredient selected from below:
(a) a peptide of the present invention;
(b) a polynucleotide encoding a peptide of the present invention in an expressible form;
(c) an APC that presents a peptide of the present invention on its surface;
(d) an exosome that presents a peptide of the present invention on its surface; and
(e) a CTL of the present invention.

In the context of the present invention, FOXM1-expressing cancers can be treated by administering a peptide, a polynucleotide, an APC, an exosome and/or a CTL of the present invention. Alternatively, an immune response against FOXM1-expressing cancers can be induced by administering a peptide, a polynucleotide, an APC, an exosome and/or a CTL of the present invention. Examples of such cancers include acute myeloid leukemia (AML), bladder cancer, breast cancer, cervical cancer, cholangiocellular cancer, chronic myeloid leukemia (CML), colon cancer, esophageal cancer, gastric cancer, diffuse gastric cancer, liver cancer, non-small-cell lung cancer (NSCLC), lymphoma, osteosarcoma, ovary cancer, pancreatic cancer, prostate cancer, kidney cancer, small-cell lung cancer (SCLC), soft tissue tumor, testicular tumor and such, but are not limited thereto. Further, an immune response against FOXM1-expressing cancer cells can be induced by administering a peptide, a polynucleotide, an APC, an exosome and/or a CTL of the present invention. Therefore, before administering a vaccine or pharmaceutical composition comprising an active ingredient described above, it is preferable to confirm whether the level of FOXM1 expression at a diseased site in the subject to be treated is augmented or not.

Thus, in one embodiment, the present invention provides a method of treating a FOXM1-expressing cancer in a patient in need of the cancer treatment, wherein the method comprises the steps below:
(i) measuring the level of FOXM1 expression in a biological sample collected from the diseased site of a subject with cancer;
(ii) identifying a subject with FOXM1-expressing cancer based on the FOXM1 expression level measured in (i); and
(iii) administering to the subject with cancer overexpressing FOXM1 as compared to a normal control at least one ingredient selected from the group consisting of (a) to (e) above.

Alternatively, the present invention further provides vaccines and pharmaceutical compositions comprising at least one active ingredient selected from the group consisting of (a) to (e) above for administration to a subject with FOXM1-expressing cancer. The present invention further provides a method of identifying or selecting a subject to be treated with at least one active ingredient selected from the group consisting of (a) to (e) above, wherein the method comprises the steps below:
(i) measuring the level of FOXM1 expression in a biological sample collected from the diseased site of a subject with cancer;
(ii) identifying a subject with FOXM1-expressing cancer based on the FOXM1 expression level measured in (i); and (iii) identifying or selecting the subject identified in (ii) as a subject who may be treated with at least one active ingredient selected from the group consisting of (a) to (e) above.

Biological samples collected from a subject for measuring the FOXM1 expression level in the above-described methods are not particularly limited, and for example, tissue samples containing cancer cells collected by biopsy or such can be preferably used. The FOXM1 expression level in a biological sample can be measured by known methods, and for example, methods that detect transcription products of the FOXM1 gene by probes or PCR methods (for example, cDNA microarray method, Northern blot method, RT-PCR method or such), methods that detect translation products of the FOXM1 gene by antibodies or such (for example, Western blot method, immunostaining method or such), and such can be used. Further, biological samples may be blood samples, and in this case, the blood level of an antibody against FOXM1 or fragments thereof is measured, and the FOXM1 expression level at a diseased site may be assessed based on the blood level. The blood level of an antibody against FOXM1 can be measured using known methods, and for example, enzyme immunoassay (EIA), enzyme-linked immunosorbent assay (ELISA), radioimmunoassay (RIA) and such using the FOXM1 protein or a peptide of the present invention as an antigen can be used.

Normally, in tissues and cells that do not express FOXM1, there is almost no detection of FOXM1 transcription products and translation products. Thus, when a transcription product or a translation product of FOXM1 is detected in cancer cells or a tissue sample containing cancer cells collected from a subject, one can determine that the subject's cancer expresses FOXM1. In blood samples of a subject that does not have FOXM1-expressing cancer, there is almost no detection of antibodies against FOXM1 or fragments thereof. Thus, when antibodies against FOXM1 or fragments thereof are detected in a blood sample collected from a subject, one can determine that the subject's cancer expresses FOXM1.

Whether a subject's cancer expresses FOXM1 or not may also be determined by comparison with the measurement results of the same type of biological material collected from a non-cancerous site of the subject or the same type of biological material collected from a subject who does not have cancer (normal control sample). That is, in comparison with the level of the target of measurement in a normal control sample (normal control level), when the level in the biological sample of the test subject is elevated, the subject's cancer is assessed to be expressing FOXM1. For example, when the amount of the target of measurement detected is increased by at least 10% or higher in comparison with the normal control level, the subject's cancer may be assessed to be expressing FOXM1. It is desirable that the amount of the target of measurement detected is increased by preferably 25% or higher, and more preferably 50% or higher than the normal control level. Further, the amount of a transcription product or a translation product of FOXM1 detected may be evaluated by normalizing against the detected amount of a known housekeeping gene such as beta-Actin, glyceraldehyde-3-phosphate dehydrogenase, or ribosomal protein P1.

In a preferred embodiment, it is preferable to confirm the HLA type of the subject before administering at least one active ingredient selected from the group consisting of (a) to (e) above. For example, for the subjects to be administered with an active ingredient in association with a peptide having the amino acid sequence selected from among SEQ ID NOs: 1, 2, 3, 6, 7, 11, 12, 17, 18, 20, 22, 24, 26, 32, 33, 36, 39, 41, 42, 45 and 46, it is preferable to select HLA-A33-positive subjects. For the subjects to be administered with an active ingredient in association with a peptide having the amino acid sequence selected from among SEQ ID NOs:48, 49, 50, 52, 53 55, 20, 56, 57, 58, 59, 60 and 61, it is preferable to select HLA-A01-positive subjects.

The present invention further provides complexes of a peptide of the present invention and HLA. The complexes of the present invention described above may be monomers or multimers. When a complex of the present invention is a multimer, the number of polymerization is not particularly limited, and it can be a multimer of any number of polymerization. Examples include a tetramer, pentamer, hexamer and such, but are not limited thereto. The multimers of the present invention also encompass dextramers (WO2002/072631) and streptamers (Knabel M et al., Nat Med. 2002 June; 8(6): 631-7). Complexes of a peptide of the present invention and HLA can be prepared according to known methods (for example, Altman J D et al., Science. 1996, 274(5284): 94-6; WO2002/072631; WO2009/003492; Knabel M et al., Nat Med. 2002 June; 8(6): 631-7, and such).

The complexes of the present invention, for example, can be used in the quantification of CTLs specific to a peptide of the present invention. For example, a blood sample is collected from a subject administered with a pharmaceutical composition of the present invention, and CD4-negative cells are prepared after separation of PBMCs and contacted with a fluorescent dye-conjugated complex of the present invention. Then, the percentage of CTLs specific to a peptide of the present invention can be measured by flow cytometry analysis. For example, immune response-inducing effects by a pharmaceutical composition of the present invention can be monitored by measuring the specific CTLs against a peptide of the present invention before, during and/or after administration of the pharmaceutical composition of the present invention.

XII. Antibodies

The present invention further provides antibodies that bind to the peptide of the present invention. Preferable antibodies bind specifically to a peptide of the present invention, but do not bind (or weakly bind) to one that is not the peptide of the present invention. In another embodiment, such an antibody may include an antibody that recognizes a peptide in the context of HLA molecules, i.e., an antibody that binds to a peptide-MHC complex. The binding specificity of an antibody can be confirmed by inhibition assay. That is, if the binding between an antibody to be analyzed and a full-length FOXM1 polypeptide is inhibited in the presence of a peptide of the present invention, this antibody is shown to specifically bind to the peptide of the present invention. Antibodies against peptides of the present invention can be used in assays of disease diagnosis and prognosis, as well as subject selection for administration of the pharmaceutical compositions of the present invention and monitoring of the pharmaceutical compositions of the present invention.

The present invention also provides various immunological assays for detecting and/or quantifying peptides of the present invention or fragments thereof. Such immunological assays include radioimmunoassay, immunochromatography, enzyme-linked immunosorbent assay (ELISA), enzyme-linked immunofluorescence assay (ELIFA) and such, without being limited thereto, and are performed within the scope of the various immunological assay formats well known in the art.

The antibodies of the present invention can be used in immunological imaging methods that can detect FOXM1-expressing diseases, and examples thereof include radioactive scintigraphic imaging using a labelled antibody of the present invention, without being limited thereto. Such assay methods are used clinically in the detection, monitoring, and prognosis of FOXM1-expressing cancers; and examples of such cancer include acute myeloid leukemia (AML), bladder cancer, breast cancer, cervical cancer, cholangiocellular cancer, chronic myeloid leukemia (CML), colon cancer, esophageal cancer, gastric cancer, diffuse gastric cancer, liver cancer, non-small-cell lung cancer (NSCLC), lymphoma, osteosarcoma, ovary cancer, pancreatic cancer, prostate cancer, kidney cancer, small-cell lung cancer (SCLC), soft tissue tumor, testicular tumor and such, without being limited thereto.

The antibodies of the present invention can be used in any arbitrary form such as monoclonal antibodies or polyclonal antibodies, and may further include anti-sera obtained by immunizing an animal such as a rabbit with a peptide of the present invention, all classes of polyclonal antibodies and monoclonal antibodies, human antibodies, as well as chimeric antibodies and humanized antibodies generated through gene recombination.

The peptide of the present invention or a fragment thereof used as an antigen for obtaining antibodies can be obtained by chemical synthesis or genetic engineering techniques based on the amino acid sequences disclosed herein.

The peptide used as an immunizing antigen may be a peptide of the present invention or a fragment of a peptide of the present invention. Further, the peptide may be bound to or conjugated with a carrier for increasing immunogenicity. Keyhole limpet hemocyanin (KLH) is well-known as a carrier. Methods for binding KLH to a peptide are also well known in the art.

Any mammal can be immunized with an antigen described above, and it is preferable to consider the compatibility with the parent cell used in cell fusion when generating a monoclonal antibody. Generally, animals of the order Rodentia, Lagomorpha or Primate can be used. Animals of the order Rodentia include, for example, mice, rats and hamsters. Animals of the order Lagomorpha include, for example, rabbits. Animals of the order Primate include, for example, Catarrhini monkeys (old world monkeys) such as cynomolgus monkey (*Macaca fascicularis*), rhesus monkeys, hamadryas, and chimpanzee.

Methods of immunizing animals with an antigen are known in the art. Intraperitoneal injection and subcutaneous injection of an antigen are standard methods for immunizing mammals. More specifically, an antigen is diluted and suspended in an appropriate amount of phosphate buffered saline (PBS), physiological saline, or such. As needed, an antigen suspension solution can be administered to mammals after being mixed with an appropriate amount of a standard adjuvant such as Freund's complete adjuvant and emulsified. Then, it is preferable to administer the antigen mixed with an appropriate amount of a Freund's incomplete adjuvant several times every 4 to 21 days. A suitable carrier may be used for immunization. After the above immunization, the serum can be examined by standard method with respect to increase in the quantity of the desired antibody.

Polyclonal antibodies against a peptide of the present invention can be prepared by collecting blood from mammals that have been confirmed with an increase in the serum level of the desired antibody after immunization, and separating the serum from blood by any conventional method. A polyclonal antibody may be a polyclonal antibody-containing serum, or a polyclonal antibody-containing fraction may be isolated from the serum. Immunoglobulin G or M can be prepared from fractions that recognize only a peptide of the present invention by, for example, using an affinity column conjugated with the peptide of the present invention, and then further purifying the fractions using a protein A or protein G column.

In order to prepare monoclonal antibodies, upon confirming an increase in the serum level of the desired antibody after immunization, immune cells are collected from the mammals and subjected to cell fusion. Immune cells used for cell fusion may be preferably obtained from the spleen. For the other parent cells fused with the above immune cells, for example, a mammalian myeloma cell, and more preferably a myeloma cell that has acquired a property for drug selection of fusion cells can be used.

The above immune cells can be fused with myeloma cells by following known methods, for example, the method of Milstein et al. (Galfre and Milstein, Methods Enzymol, 1981, 73: 3-46).

Hybridomas obtained by cell fusion can be selected by culturing them in a standard selection medium such as the HAT medium (a medium containing hypoxanthine, aminopterin and thymidine). Cell culturing is typically continued in the HAT medium for a sufficient period of time (for example, several days to several weeks) to allow death of all other cells (non-fused cells) besides the desired hybridomas. Then, hybridoma cells producing the desired antibody can be screened and cloned by performing a standard limiting dilution.

In addition to the above methods of immunizing a non-human animal with an antigen for hybridoma preparation, human lymphocytes such as EB virus-infected lymphocytes can be immunized in vitro with a peptide, cells expressing the peptide, or lysates thereof. Then, the immunized lymphocytes can be fused with immortalized human-derived myeloma cells such as U266 to obtain hybridomas producing a desired human antibody capable of binding to the peptide (JPS63-17688).

Next, the obtained hybridoma is transplanted into the abdominal cavity of a mouse, and the ascites is extracted. The obtained monoclonal antibody can be purified by, for example, ammonium sulfate precipitation, protein A or protein G column, DEAE ion-exchange chromatography, or affinity column conjugated with the peptide of the present invention.

Alternatively, antibody-producing immune cells such as the immunized lymphocytes can be immortalized by a cancer gene and used for the preparation of monoclonal antibodies.

The monoclonal antibodies obtained as such can also be prepared by recombination using genetic engineering techniques (see, e.g., Borrebaeck and Larrick, Therapeutic Monoclonal Antibodies published in United Kingdom by MacMillan Publishers LTD (1990)). For example, an antibody-encoding DNA can be cloned from immune cells such as antibody-producing hybridoma or immunized lymphocytes and inserted into a suitable vector, and then this is introduced into host cells to prepare a recombinant antibody. The present invention also provides recombinant antibodies prepared as described above.

Further, the antibodies of the present invention may be antibody fragments or modified antibodies, as long as they bind to the peptides of the present invention. For example, it is desirable that the antibody fragment contains an antigen-binding site(s) of the antibodies. Specifically, the antibody fragments may be Fab, $F(ab')_2$, Fv, or a single chain Fv(scFv) in which Fv fragments derived from an H chain and an L chain are linked with a suitable linker (Huston et al., Proc Natl Acad Sci USA, 1988, 85: 5879-83). More specifically, antibody fragments may be generated by treating an antibody with an enzyme such as papain or pepsin. Alternatively, a gene encoding an antibody fragment may be constructed, inserted into an expression vector, and expressed in an appropriate host cell (see, e.g., Co et al., J Immunol, 1994, 152: 2968-76; Better and Horwitz, Methods Enzymol, 1989, 178: 476-96; Pluckthun and Skerra, Methods Enzymol, 1989, 178: 497-515; Lamoyi, Methods Enzymol, 1986, 121: 652-63; Rousseaux et al., Methods Enzymol, 1986, 121: 663-9; Bird and Walker, Trends Biotechnol, 1991, 9: 132-7).

Antibodies may be modified by conjugation with various molecules such as polyethyleneglycol (PEG). The present invention provides such modified antibodies. Modified antibodies can be obtained by chemically modifying the antibodies. These modification methods are conventional in the art.

Alternatively, the antibodies of the present invention can be obtained as chimeric antibodies of a non-human antibody-derived variable region and a human antibody-derived constant region, or as humanized antibodies comprising a non-human antibody-derived complementarity determining region (CDR) and a human antibody-derived framework region (FR) and constant region. Such antibodies can be prepared according to known techniques. Humanization can be carried out by substituting a human antibody sequence(s) with a corresponding non-human antibody CDR sequence(s) (see, e.g., Verhoeyen et al., Science, 1988, 239: 1534-6). Thus, such humanized antibodies are chimeric antibodies in which the substantially less than an intact human variable domain has been substituted with a corresponding sequence from a non-human species.

Intact human antibodies comprising a human variable region in addition to the human framework and constant regions can also be used. Such antibodies can be generated using various techniques known in the art. For example, in vitro methods include use of recombinant libraries of human antibody fragments presented on bacteriophages (for example, Hoogenboom & Winter, J. Mol. Biol., 1991, 227: 381). Similarly, human antibodies can also be generated by introducing human immunoglobulin gene loci into transgenic animals, for example, mice, in which the endogenous immunoglobulin genes have been partially or completely inactivated. This approach is described in, for example, U.S. Pat. Nos. 6,150,584, 5,545,807, 5,545,806, 5,569,825, 5,625,126, 5,633,425 and 5,661,016.

Antibodies obtained as described above may be purified to homogeneity. For example, antibody separation and purification can be performed according to separation methods and purification methods used for general proteins. For example, an antibody can be separated and isolated by appropriately selecting and combining use of column chromatographies such as affinity chromatography, filter, ultrafiltration, salting-out, dialysis, SDS-polyacrylamide gel electrophoresis and isoelectric focusing electrophoresis (Antibodies: A Laboratory Manual. Ed Harlow and David Lane, Cold Spring Harbor Laboratory (1988)), but are not limited thereto. Protein A column and protein G column can be used as the affinity column. Exemplary protein A columns to be used include, for example, Hyper D, POROS and Sepharose F. F. (Pharmacia).

Besides affinity chromatography, exemplary chromatography includes, for example, ion-exchange chromatography, hydrophobic chromatography, gel filtration, reversed-phase chromatography, adsorption chromatography and such (Strategies for Protein Purification and Characterization: A Laboratory Course Manual. Ed Daniel R. Marshak et al., Cold Spring Harbor Laboratory Press (1996)). The chromatography procedures can be carried out by liquid-phase chromatography such as HPLC and FPLC.

The antigen-binding activity of an antibody of the present invention can be measured, for example, by using absorbance measurement, enzyme-linked immunosorbent assay (ELISA), enzyme immunoassay (EIA), radioimmunoassay (RIA), and/or immunofluorescence (IF). In the case of ELISA, an antibody of the present invention is immobilized onto a plate, a peptide of the present invention is applied to the plate, and then a sample containing the desired antibody, such as culture supernatant of antibody-producing cells or purified antibodies, is applied. Next, a secondary antibody that recognizes the primary antibody and is labelled with an enzyme such as alkaline phosphatase is applied and the plate is incubated. Then, after washing, an enzyme substrate such as p-nitrophenyl phosphate is applied to the plate, and the antigen-binding activity of the sample is evaluated by measuring absorbance. To assess the binding activity of an antibody, peptide fragments such as C-terminal or N-terminal fragments may be used as an antigen. BIAcore (Pharmacia) may be used to evaluate the activity of an antibody of the present invention.

It is possible to detect or measure a peptide of the present invention using the above methods, by exposing an antibody of the present invention to a sample assumed to contain the peptide of the present invention, and detecting or measuring an immune complex formed between the antibody and the peptide.

For example, an antibody of the present invention can be used to detect a peptide of the present invention present in the blood sample (for example, serum sample) of a subject. Alternatively, an antibody of the present invention present in the blood sample (for example, serum sample) of a subject can also be detected using a peptide of the present invention. The result of measuring a peptide of the present invention or an antibody of the present invention in the blood sample of a subject can be utilized to the subject selection for administration of the pharmaceutical compositions of the present invention or monitoring of the efficacy of the pharmaceutical compositions of the present invention. In addition, it has been reported that patients having an antibody against a peptide administered as vaccine may have high responsiveness to the vaccine. Therefore, the peptide of the present invention can also be utilized as an immunoassay antigen for selecting, among cancer patients, a patient expected to show high responsiveness to a vaccine comprising the peptide using an antibody against the peptide as an index.

XIII. Vectors and Host Cells

The present invention provides vectors comprising a polynucleotide encoding a peptide of the present invention and host cells introduced with the vectors. A vector of the present invention may be used to keep a polynucleotide of the present invention in a host cell, to express a peptide of the present invention in a host cell, or to administer a polynucleotide of the present invention for gene therapy.

When *E. coli* is a host cell and a vector is amplified and produced in a large amount in *E. coli* (for example, JM109, DH5-alpha, HB101 or XL1-Blue), the vector needs to have a "replication origin" for amplification in *E. coli* and a marker gene for selection of transformed *E. coli* (for example, a drug resistance gene selected by a drug such as ampicillin, tetracycline, kanamycin, chloramphenicol). For example, the M13-series vectors, pUC-series vectors, pBR322, pBluescript, pCR-Script and such can be used. In addition, pGEM-T, pDIRECT and pT7 can be used for cloning as well as the above vectors. When a vector is used in the production of a peptide of the present invention, an expression vector can be used. For example, an expression vector for expression in *E. coli* needs to have the above features for amplification in *E. coli*. When *E. coli* such as JM109, DH5-alpha, HB101 or XL1-Blue are used as a host cell, the vector needs to have a promoter, for example, lacZ promoter (Ward et al., Nature, 1989, 341: 544-6; FASEB J, 1989, 6: 2422-7), araB promoter (Better et al., Science, 1988, 240: 1041-3), T7 promoter or the like, that can efficiently express the desired gene in *E. coli*. In that respect, pGEX-5X-1 (Pharmacia), "QIAexpress system" (Qiagen), pEGFP and pET (in this case, the host is preferably BL21 which expresses T7 RNA polymerase), for example, can be used instead of the above vectors. Additionally, the vector may contain a signal sequence for peptide secretion. An exemplary signal sequence that directs the peptide to be secreted to the periplasm of the *E. coli* is the pelB signal sequence (Lei et al., J Bacteriol, 1987, 169: 4379). Means for introducing the vectors into the target host cells include, for example, the calcium chloride method and the electroporation method.

In addition to *E. coli*, for example, expression vectors derived from mammals (for example, pcDNA3 (Invitrogen) and pEGF-BOS (Nucleic Acids Res, 1990, 18(17): 5322), pEF, pCDM8), expression vectors derived from insect cells (for example, "Bac-to-BAC baculovirus expression system" (GIBCO BRL), pBacPAK8), expression vectors derived from plants (e.g., pMH1, pMH2), expression vectors derived from animal viruses (e.g., pHSV, pMV, pAdexLcw), expression vectors derived from retroviruses (e.g., pZIpneo), expression vectors derived from yeast (e.g., "Pichia Expression Kit" (Invitrogen), pNV11, SP-Q01) and expression vectors derived from *Bacillus subtilis* (e.g., pPL608, pKTH50) can be used for producing the polypeptide of the present invention.

In order to express the vector in animal cells such as CHO, COS or NIH3T3 cells, the vector needs to carry a promoter necessary for expression in such cells, for example, the SV40 promoter (Mulligan et al., Nature, 1979, 277: 108), the MMLV-LTR promoter, the EF1-alpha promoter (Mizushima et al., Nucleic Acids Res, 1990, 18: 5322), the CMV promoter and the like, and preferably a marker gene for selecting transformants (for example, a drug resistance gene selected by a drug (e.g., neomycin, G418)). Examples of known vectors with these characteristics include, for example, pMAM, pDR2, pBK-RSV, pBK-CMV, pOPRSV and pOP13.

The embodiments of the present invention are exemplified below based on the above explanation; however, the present invention is not limited to these embodiments.

[1] A peptide of less than 15 amino acids having cytotoxic T cell (CTL)-inducing ability, which comprises the amino acid sequence selected from the group of:

- (a) the amino acid sequence selected from the group consisting of SEQ ID NOs: 1, 2, 3, 6, 7, 11, 12, 17, 18, 20, 22, 24, 26, 32, 33, 36, 39, 41, 42, 45, 46, 48, 49, 50, 52, 53, 55, 56, 57, 58, 59, 60 and 61; and
- (b) the amino acid sequence in which one, two or several amino acids are substituted, deleted, inserted and/or added to the amino acid sequence selected from the group consisting of SEQ ID NOs: 1, 2, 3, 6, 7, 11, 12, 17, 18, 20, 22, 24, 26, 32, 33, 36, 39, 41, 42, 45, 46, 48, 49, 50, 52, 53, 55, 56, 57, 58, 59, 60 and 61.

[2] The peptide of [1], which is selected from the group consisting of (i) and (ii) below:

- (i) a peptide comprising the amino acid sequence comprising one or more substitution(s) selected from the group consisting of (a) to (c) below in the amino acid sequence selected from the group consisting of SEQ ID NOs: 1, 2, 3, 6, 7, 11, 12, 17, 18, 20, 22, 24, 26, 32, 33, 36, 39, 41, 42, 45 and 46:
  - (a) the first amino acid from the N terminus is substituted with an amino acid selected from the group consisting of aspartic acid and glutamic acid;
  - (b) the second amino acid from the N terminus is substituted with an amino acid selected from the group consisting of phenylalanine, tyrosine, alanine, isoleucine, leucine and valine; and
  - (c) the C-terminal amino acid is substituted with an amino acid selected from the group consisting of arginine and lysine; and
- (ii) a peptide comprising the amino acid sequence comprising one or more substitution(s) selected from the group consisting of (a) to (c) below introduced into the amino acid sequence selected from the group consisting of SEQ ID NOs: 48, 49, 50, 52, 53, 55, 20, 56, 57, 58, 59, 60 and 61:
  - (a) the second amino acid from the N terminus is substituted with an amino acid selected from the group consisting of threonine and serine;
  - (b) the third amino acid from the N terminus is substituted with an amino acid selected from the group consisting of aspartic acid and glutamic acid; and
  - (c) the C-terminal amino acid is substituted with tyrosine.

[3] The peptide of [1], which consists of the amino acid sequence selected from the group consisting of SEQ ID NOs: 1, 2, 3, 6, 7, 11, 12, 17, 18, 20, 22, 24, 26, 32, 33, 36, 39, 41, 42, 45, 46, 48, 49, 50, 52, 53, 55, 56, 57, 58, 59, 60 and 61.

[4] A polynucleotide, which encodes the peptide of any one of [1] to [3].

[5] A composition comprising a pharmaceutically acceptable carrier and at least one ingredient selected from the group consisting of (a) to (e) below:

- (a) one or more types of peptides of any one of [1] to [3];
- (b) one or more types of polynucleotides encoding the peptide(s) of any one of [1] to [3] in an expressible form;
- (c) an antigen-presenting cell (APC) that presents on its cell surface a complex of the peptide of any one of [1] to [3] and an HLA antigen;
- (d) an exosome that presents on its cell surface a complex of the peptide of any one of [1] to [3] and an HLA antigen; and
- (e) a CTL that targets the peptide of any one of [1] to [3].

[6] The composition of [5], which is a composition for inducing a CTL(s), wherein the ingredient is at least one ingredient selected from the group consisting of (a) to (d) below:

- (a) one or more types of peptides of any one of [1] to [3];
- (b) one or more types of polynucleotides encoding the peptide(s) of any one of [1] to [3] in an expressible form;
- (c) an antigen-presenting cell (APC) that presents on its cell surface a complex of the peptide of any one of [1] to [3] and an HLA antigen; and (d) an exosome that presents on its cell surface a complex of the peptide of any one of [1] to [3] and an HLA antigen.

[7] The composition of [5], which is a pharmaceutical composition.

[8] The composition of [7], which is pharmaceutical composition for one or more uses selected from the group consisting of (i) cancer treatment, (ii) cancer prevention (prophylaxis) and (iii) prevention (prophylaxis) of postoperative cancer recurrence.

[9] The composition of [7], which is for inducing an immune response against cancer.

[10] The composition of [8] or [9], wherein the cancer is selected from the group consisting of acute myeloid leukemia (AML), bladder cancer, breast cancer, cervical cancer, cholangiocellular cancer, chronic myeloid leukemia (CML), colon cancer, esophageal cancer, gastric cancer, diffuse gastric cancer, liver cancer, non-small-cell lung cancer (NSCLC), lymphoma, osteosarcoma, ovary cancer, pancreatic cancer, prostate cancer, kidney cancer, small-cell lung cancer (SCLC), soft tissue tumor and testicular tumor.

[11] The composition of any one of [5] to [10], which is formulated for administration to a subject positive for at least one HLA selected from the group consisting of HLA-A33 and HLA-A01.

[12] A method of inducing an APC(s) having CTL-inducing ability, which comprises a step selected from the group consisting of below:

(a) contacting an APC(s) with the peptide of any one of [1] to [3] in vitro, ex vivo or in vivo; and (b) introducing a polynucleotide encoding the peptide of any one of [1] to [3] into an APC(s).

[13] A method of inducing a CTL(s), which comprises a step selected from the group consisting of (a) to (c) below:

(a) co-culturing a CD8-positive T cell(s) with an APC(s) that presents on its surface a complex of an HLA antigen and the peptide of any one of [1] to [3];

(b) co-culturing a CD8-positive T cell(s) with an exosome (s) that presents on its surface a complex of an HLA antigen and the peptide of any one of [1] to [3]; and (c) introducing into a CD8-positive T cell(s) a polynucleotide encoding each subunit of a T cell receptor (TCR) capable of binding to the peptide of any one of [1] to [3] presented by an HLA antigen on a cell surface.

[14] An APC that presents on its surface a complex of an HLA antigen and the peptide of any one of [1] to [3].

[15] The APC of [14], which is induced by the method of [12].

[16] A CTL that targets the peptide of any one of [1] to [3].

[17] The CTL of [16], which is induced by the method of [13].

[18] A method of inducing an immune response against cancer, which comprises administering to a subject at least one ingredient selected from the group consisting of (a) to (e) below:

(a) one or more types of peptides of any one of [1] to [3];

(b) one or more types of polynucleotides encoding the peptide(s) of any one of [1] to [3] in an expressible form;

(c) an antigen-presenting cell (APC) that presents on its cell surface a complex of the peptide of any one of [1] to [3] and an HLA antigen;

(d) an exosome that presents on its cell surface a complex of the peptide of any one of [1] to [3] and an HLA antigen; and (e) a CTL that targets the peptide of any one of [1] to [3].

[19] A method of treating and/or preventing cancer, and/or preventing postoperative recurrence thereof, which comprises administering to a subject at least one ingredient selected from the group consisting of (a) to (e) below:

(a) one or more types of peptides of any one of [1] to [3];

(b) one or more types of polynucleotides encoding the peptide(s) of any one of [1] to [3] in an expressible form;

(c) an antigen-presenting cell (APC) that presents on its cell surface a complex of the peptide of any one of [1] to [3] and an HLA antigen;

(d) an exosome that presents on its cell surface a complex of the peptide of any one of [1] to [3] and an HLA antigen; and (e) a CTL that targets the peptide of any one of [1] to [3].

[20] An antibody that binds to the peptide of any one of [1] to [3].

[21] A method of screening for a peptide having CTL-inducing ability, which comprises the steps of:

(a) generating candidate sequences consisting of an amino acid sequence in which one, two or several amino acid residues are substituted, deleted, inserted and/or added to an original amino acid sequence consisting of the amino acid sequence selected from the group consisting of SEQ ID NOs: 1, 2, 3, 6, 7, 11, 12, 17, 18, 20, 22, 24, 26, 32, 33, 36, 39, 41, 42, 45, 46, 48, 49, 50, 52, 53, 55, 56, 57, 58, 59, 60 and 61;

(b) selecting from among the candidate sequences generated in (a), a candidate sequence that does not have significant homology (sequence identity) with any known human gene product other than FOXM1;

(c) contacting an APC(s) with a peptide consisting of the candidate sequence selected in (b);

(d) contacting the APC(s) of (c) with a CD8-positive T cell(s); and (e) selecting a peptide having an equal to or higher CTL-inducing ability than that of a peptide consisting of the original amino acid sequence.

[22] Use of at least one active ingredient selected from the group consisting of (a) to (e) below in the manufacture of a composition for inducing an immune response against cancer:

(a) one or more types of peptides of any one of [1] to [3];

(b) one or more types of polynucleotides encoding the peptide(s) of any one of [1] to [3] in an expressible form;

(c) an antigen-presenting cell (APC) that presents on its cell surface a complex of the peptide of any one of [1] to [3] and an HLA antigen;

(d) an exosome that presents on its cell surface a complex of the peptide of any one of [1] to [3] and an HLA antigen; and (e) a CTL that targets the peptide of any one of [1] to [3].

[23] Use of at least one ingredient selected from the group consisting of (a) to (e) below in the manufacture of a pharmaceutical composition for treating and/or preventing cancer, and/or preventing postoperative recurrence thereof:

(a) one or more types of peptides of any one of [1] to [3];

(b) one or more types of polynucleotides encoding the peptide(s) of any one of [1] to [3] in an expressible form;

(c) an antigen-presenting cell (APC) that presents on its cell surface a complex of the peptide of any one of [1] to [3] and an HLA antigen;

(d) an exosome that presents on its cell surface a complex of the peptide of any one of [1] to [3] and an HLA antigen; and (e) a CTL that targets the peptide of any one of [1] to [3].

[24] Use of at least one ingredient selected from the group consisting of (a) to (e) below for inducing an immune response against cancer:

(a) one or more types of peptides of any one of [1] to [3];

(b) one or more types of polynucleotides encoding the peptide(s) of any one of [1] to [3] in an expressible form;

(c) an antigen-presenting cell (APC) that presents on its cell surface a complex of the peptide of any one of [1] to [3] and an HLA antigen;

(d) an exosome that presents on its cell surface a complex of the peptide of any one of [1] to [3] and an HLA antigen; and (e) a CTL that targets the peptide of any one of [1] to [3].

[25] Use of at least one ingredient selected from the group consisting of (a) to (e) below for treating and/or preventing cancer and/or preventing postoperative recurrence thereof:

(a) one or more types of peptides of any one of [1] to [3];

(b) one or more types of polynucleotides encoding the peptide(s) of any one of [1] to [3] in an expressible form;

(c) an antigen-presenting cell (APC) that presents on its cell surface a complex of the peptide of any one of [1] to [3] and an HLA antigen;

(d) an exosome that presents on its cell surface a complex of the peptide of any one of [1] to [3] and an HLA antigen; and (e) a CTL that targets the peptide of any one of [1] to [3].

[26] A method of inducing cytotoxic activity against a FOXM1-expressing cell(s), which comprises a step of administering to a subject at least one ingredient selected from the group consisting of (a) to (e) below:

(a) one or more types of peptides of any one of [1] to [3];

(b) one or more types of polynucleotides encoding the peptide(s) of any one of [1] to [3] in an expressible form;

(c) an antigen-presenting cell (APC) that presents on its cell surface a complex of the peptide of any one of [1] to [3] and an HLA antigen;

(d) an exosome that presents on its cell surface a complex of the peptide of any one of [1] to [3] and an HLA antigen; and (e) a CTL that targets the peptide of any one of [1] to [3].

[27] A freeze-dried formulation comprising one or more types of peptides of any one of [1] to [3].

[28] A pharmaceutical composition, which is prepared by a method that comprises dissolving one or more types of peptides of any one of [1] to [3] in a water-soluble carrier, and performing filtration sterilization.

[29] A filtration-sterilized aqueous solution, which is an aqueous solution that comprises one or more types of peptides of any one of [1] to [3] and a water-soluble carrier.

[30] An emulsion comprising one or more types of peptides of any one of [1] to [3], a water-soluble carrier and an oil adjuvant.

[31] A kit comprising a container that houses the composition of any one of [5] to [11] and a container that houses an adjuvant.

[32] A kit comprising a container that stores a freeze-dried formulation comprising the peptide of any one of [1] to [3], a container that stores an adjuvant, and a container that stores a re-dissolving solution for the freeze-dried formulation.

The present invention is explained herein in detail with reference to its specific embodiments. However, it should be understood that the above explanation is in fact an illustrative and explanatory explanation, and is intended to explain the present invention and preferred embodiments thereof. Through routine experimentation, one skilled in the art will readily recognize that various changes and modifications can be made therein without departing from the spirit and scope of the present invention. Thus, the present invention is not confined to the above explanation, but is intended to be defined by the appended claims and equivalents thereto.

Hereinbelow, the present invention is described in more detail with reference to the Examples. Nevertheless, while the following materials, method and Examples may serve to assist one of ordinary skill in making and using certain embodiments of the present invention, there are only intended to illustrate aspects of the present invention and thus in no way to limit the scope of the present invention. One of ordinary skill in the art can use methods and materials similar or equivalent to those described herein in the practice or testing of the present invention.

All prior art documents cited herein are incorporated by reference in the present specification.

EXAMPLES

Example 1

Materials and Methods

Cell Lines

C1R cells, an HLA-A- and HLA-B-negative human B lymphoblastoid cell line, and COS7 cells, an African green monkey kidney cell line, were purchased from ATCC.

Generation of Target Cells with Steady HLA-A*33:03 Expression

C1R cells (C1R-A33) that steadily express HLA-A*33:03 were used as cells that stimulate CTLs. A cDNA encoding the HLA-A*33:03 gene was amplified by PCR and incorporated into an expression vector. C1R cells into which the HLA-A*33:03 gene expression vector was introduced were cultured under drug selection for two weeks in medium containing G418 (Invitrogen). The G418-resistant C1R cell suspension was diluted, seeded in a 96-well plate, and further selectively cultured for 30 days in a G418-containing medium. The HLA-A*33:03 expression in C1R cells was verified by flow cytometric analysis.

Selection of FOXM1-Derived Peptides

FOXM1-derived 9mer and 10mer peptides that are expected to bind to the HLA-A*33:03 molecule were determined using the binding prediction server "NetMHC pan2.8" (www.cbs.dtu.dk/services/NetMHCpan-2.8/) (Buus et al., Tissue Antigens. 2003, 62(5): 378-84; Nielsen et al., Protein Sci. 2003, 12(5): 1007-17; Bioinformatics. 2004, 20(9): 1388-97).

Peptide Synthesis

The peptides were synthesized by American Peptide Company (Sunnyvale, CA) according to a standard solid-phase synthesis method, and purified by reversed phase high-performance liquid chromatography (HPLC). The quality of the peptides (purity of 90% or higher) was guaranteed by HPLC and mass spectrometry. The peptides were dissolved with dimethylsulfoxide (final concentration: 20 mg/ml) and stored at −80 degrees C.

In Vitro CTL Induction

Monocyte-derived dendritic cells (DCs) were used as the antigen-presenting cell to induce a specific cytotoxic T lymphocyte (CTL) response against peptides presented on human leukocyte antigens (HLAs). As already reported in literatures, DCs were generated in vitro (Nakahara S et al., Cancer Res 2003, 63(14): 4112-8). Specifically, peripheral-blood mononuclear cells (PBMCs) collected from healthy volunteers (HLA-A*33:03-positive) with the Ficoll-Paque plus solution (Pharmacia) were seeded in plastic tissue culture dishes (Corning) to let the monocytes in the PBMCs adhere to the dishes. This was cultured in the presence of 1000 IU/ml granulocyte macrophage colony-stimulating factor (R&D System) and 1000 IU/ml interleukin (IL)-4 (R&D System) for seven days. An AIM-V medium (Invitrogen) containing 5% inactivated AB-type serum (ABS) was used as the medium. DCs that were induced to differentiate from monocytes using the cytokines were pulsed with 20 micro-g/ml of each synthesized peptide (37 degrees C., three hours). Peptide pulsing was carried out in an AIM-V medium containing 3 micro-g/ml beta 2-microglobulin. These peptide-pulsed DCs were inactivated by X-ray irradiation (20 Gy), mixed in a 1:20 ratio with autologous CD8 positive T cells obtained by positive selection using the CD8 Positive Isolation Kit (Invitrogen) ($1.5\times10^4$ DCs and $3\times10^5$ CD8 positive T cells), and cultured in a 48-well plate (Corning). Each well contained 0.5 ml of the 5% ABS/AIM-V medium, and IL-7 (R&D System) was added thereto (final concentration: 10 ng/ml). Two days after the start of the culture, IL-2 (Novartis) was added (final concentration: 20 IU/ml). On day 7 and day 14 of culture, the CD8 positive T cells were further stimulated with peptide-pulsed DCs. The DCs were prepared at the time of use by the same method as above. After day 21 (after three DC stimulations), IFN-gamma production against the peptide-pulsed C1R-A33 was confirmed using human interferon (IFN)-gamma enzyme-linked immunospot (ELISPOT) assay (Tanaka H et al., Br J Cancer 2001, 84(1): 94-9; Umano Y et al., Br J Cancer 2001, 84(8): 1052-7; Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).

CTL Propagation Procedure

CTLs were propagated using methods similar to those reported by Riddell et al. (Walter E A et al., N Engl J Med 1995, 333(16): 1038-44; Riddell S R et al., Nat Med 1996, 2(2): 216-23). The CTLs were cultured in 25 ml 5% ABS/AIM-V medium together with two types of Mitomycin C-treated human B lymphoblastoid cell lines ($5\times10^6$ cells/25 ml medium each) and an anti-CD3 antibody (final concentration: 40 ng/ml). On the day after beginning of the culturing, IL-2 (final concentration: 120 IU/ml) was added to the culture. On days 5, 8 and 11, the medium was changed to a 5% ABS/AIM-V medium containing IL-2 (final concentration: 30 IU/ml) (Tanaka H et al., Br J Cancer 2001, 84(1): 94-9; Umano Y et al., Br J Cancer 2001, 84(8): 1052-7; Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).

Establishment of CTL Clones

After induction of CTLs in vitro, the CTLs were seeded onto 96-well round-bottomed microplates (Nalge Nunc International) at 1 cell/well or 10 cells/well. The CTLs were cultured with two types of Mitomycin C-treated human B lymphoblastoid cell lines ($1\times10^4$ cells/well each) in a total of 150 micro-l/well 5% ABS/AIM-V medium with an anti-CD3 antibody (final concentration: 30 ng/ml) and IL-2 (final concentration: 125 IU/ml). Ten days later, 50 micro-l 5% ABS/AIM-V medium containing 500 IU/ml IL-2 was added to the culture. On day 14 or after, CTLs that showed peptide-specific IFN-gamma production in an ELISPOT assay were propagated using the same method as described above (Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).

Confirmation of IFN-Gamma Production

To confirm the peptide-specific IFN-gamma production of CTLs induced with a peptide, an IFN-gamma ELISPOT assay and an IFN-gamma ELISA were performed. Peptide-pulsed C1R-A33 ($1\times10^4$ cells/well) was prepared as the target cell. The IFN-gamma ELISPOT assay and IFN-gamma ELISA were performed according to the assay kit manufacturer's manual.

Preparation of Target Cells Forcibly Expressing FOXM1 and HLA-A*33:03

A cDNA encoding the FOXM1 or HLA-A*33:03 gene was amplified by PCR. The PCR-amplified product was each incorporated into an expression vector. Either or both of the FOXM1 gene-expressing vector and the HLA-A*33:03 gene-expressing vector were introduced into COS7 cells, which is a cell line negative for HLA, using Lipofectamine 2000 (Invitrogen). On the day after gene introduction, COS7 cells were detached and harvested using versene (Invitrogen), and used as the target cell for confirmation of IFN-gamma production ($5\times10^4$ cells/well).

Results

Prediction of FOXM1-Derived HLA-A*33:03-Binding Peptides

Tables 1a and 1b show FOXM1-derived 9mer peptides and 10mer peptides that have been predicted to bind to HLA-A*33:03 by "NetMHC pan2.8" in the descending order of binding affinity. A total of 47 peptides that potentially have an HLA-A*33:03-binding ability was used as epitope peptide candidates.

TABLE 1a

HLA-A*33:03-binding 9mer peptides derived from FOXM1

| Start Position | Amino Acid Sequence | Kd (nM) | SEQ ID NO |
|---|---|---|---|
| 180 | SLSNIQWLR | 13.57 | 1 |
| 308 | WTIHPSANR | 34.66 | 2 |
| 693 | QVSGLAANR | 75.29 | 3 |
| 190 | MSSDGLGSR | 132.48 | 4 |
| 515 | MLVIQHRER | 138.98 | 5 |
| 516 | LVIQHRERR | 156.26 | 6 |
| 146 | AARDVNLPR | 230.20 | 7 |
| 140 | TLGPKPAAR | 248.65 | 8 |
| 389 | SLMSSELAR | 262.06 | 9 |
| 246 | QFAINSTER | 277.30 | 10 |
| 289 | LSLHDMFVR | 439.26 | 11 |
| 228 | SWQNSVSER | 481.46 | 12 |
| 125 | TQTSYDAKR | 519.42 | 13 |
| 489 | DSSQSPTPR | 646.55 | 14 |
| 270 | FPYFKHIAK | 766.69 | 15 |
| 216 | QVKVEEPSR | 835.12 | 16 |
| 502 | YSGLRSPTR | 855.62 | 17 |

TABLE 1a-continued

| HLA-A*33:03-binding 9mer peptides derived from FOXM1 | | | |
|---|---|---|---|
| Start Position | Amino Acid Sequence | Kd (nM) | SEQ ID NO |
| 321 | DQVFKQQKR | 1343.52 | 18 |
| 393 | SELARHSKR | 1443.91 | 19 |
| 341 | KTELPLGAR | 1574.92 | 90 |
| 547 | FSEGPSTSR | 1679.70 | 21 |

Start position indicates the number of amino acid residue from the N terminus of FOXM1.

The dissociation constant [Kd (nM)] is derived from "NetMHC2.8".

TABLE 1b

| HLA-A*33:03-binding 10mer peptides derived from FOXM1 | | | |
|---|---|---|---|
| Start Position | Amino Acid Sequence | Kd (nM) | SEQ ID NO |
| 514 | EMLVIQHRER | 26.71 | 22 |
| 139 | ETLGPKPAAR | 33.00 | 23 |
| 179 | NSLSNIQWLR | 34.89 | 24 |
| 288 | NLSLHDMFVR | 91.77 | 25 |
| 501 | SYSGLRSPTR | 109.92 | 26 |
| 515 | MLVIQHRERR | 114.82 | 27 |
| 307 | FWTIHPSANR | 131.76 | 28 |
| 398 | HSKRVRIAPK | 150.52 | 29 |
| 245 | IQFAINSTER | 172.14 | 30 |
| 269 | HFPYFKHIAK | 176.26 | 31 |
| 124 | QTQTSYDAKR | 190.55 | 32 |
| 595 | STPSKSVLPR | 240.63 | 33 |
| 394 | ELARHSKRVR | 278.30 | 34 |
| 247 | FAINSTERKR | 299.53 | 35 |
| 546 | LFSEGPSTSR | 332.38 | 36 |
| 392 | SSELARHSKR | 608.20 | 37 |
| 227 | ASWQNSVSER | 753.17 | 38 |
| 391 | MSSELARHSK | 875.46 | 39 |
| 326 | QQKRPNPELR | 880.19 | 40 |
| 607 | ESWRLTPPAK | 1179.88 | 41 |
| 765 | WIEDHFPYFK | 1214.75 | 42 |
| 497 | RPKKSYSGLR | 1332.87 | 43 |
| 471 | EWPSPAPSFK | 1418.64 | 44 |
| 4 | SPRRPLILKR | 1427.21 | 45 |

TABLE 1b-continued

| HLA-A*33:03-binding 10mer peptides derived from FOXM1 | | | |
|---|---|---|---|
| Start Position | Amino Acid Sequence | Kd (nM) | SEQ ID NO |
| 388 | ASLMSSELAR | 1586.13 | 46 |
| 651 | SAPPLESPQR | 1587.27 | 47 |

Start position indicates the number of amino acid residue from the N terminus of FOXM1.

The dissociation constant [Kd (nM)] is derived from "NetMHC2.8".

Induction of CTLs by the Predicted FOXM1-Derived HLA-A*33:03-Restricted Peptides FOXM1-derived peptide-specific CTLs were induced according to the protocol described in "Materials and methods". The peptide-specific IFN-gamma production was confirmed by an ELISPOT assay (FIG. 1). Peptide-specific IFN-gamma production was observed in Well #6 with FOXM1-A33-9-180 (SEQ ID NO: 1) (a), Well #3 with FOXM1-A33-9-308 (SEQ ID NO: 2) (b),
Well #4 with FOXM1-A33-9-693 (SEQ ID NO: 3) (c),
Well #3 with FOXM1-A33-9-516 (SEQ ID NO: 6) (d),
Well #5 with FOXM1-A33-9-146 (SEQ ID NO: 7) (e),
Well #6 with FOXM1-A33-9-289 (SEQ ID NO: 11) (f),
Well #6 with FOXM1-A33-9-228 (SEQ ID NO: 12) (g),
Well #4 with FOXM1-A33-9-502 (SEQ ID NO: 17) (h),
Well #2 with FOXM1-A33-9-321 (SEQ ID NO: 18) (i),
Well #6 with FOXM1-A33-9-341 (SEQ ID NO: 20) (j),
Well #8 with FOXM1-A33-10-514 (SEQ ID NO: 22) (k),
Well #6 with FOXM1-A33-10-179 (SEQ ID NO: 24) (l),
Well #5 with FOXM1-A33-10-501 (SEQ ID NO: 26) (m),
Well #5 with FOXM1-A33-10-124 (SEQ ID NO: 32) (n),
Well #3 with FOXM1-A33-10-595 (SEQ ID NO: 33) (o),
Well #5 with FOXM1-A33-10-546 (SEQ ID NO: 36) (p),
Well #6 with FOXM1-A33-10-391 (SEQ ID NO: 39) (q),
Well #3 with FOXM1-A33-10-607 (SEQ ID NO: 41) (r),
Well #2 with FOXM1-A33-10-265 (SEQ ID NO: 42) (s),
Well #6 with FOXM1-A33-10-4 (SEQ ID NO: 45) (t) and
Well #5 with FOXM1-A33-10-388 (SEQ ID NO: 46) (u).

Meanwhile, specific IFN-gamma production against other peptides shown in Tables 1a and 1b was not observed. For example, specific IFN-gamma production was not observed against FOXM1-A33-10-288 (SEQ ID NO: 25) (v). As a result, although all the peptides had the potential of binding to HLA-A*33:03, 21 peptides were selected as peptides having CTL-inducing ability.

Establishment of CTL Lines and Clones Specific to HLA-A*33:03-Restricted FOXM1-Derived Peptides CTL lines were established by propagating cells in Well #3 with FOXM1-A33-9-308 (SEQ ID NO: 2) (a), Well #5 with FOXM1-A33-9-146 (SEQ ID NO: 7) (b), Well #6 with FOXM1-A33-10-391 (SEQ ID NO: 39) (c) and Well #2 with FOXM1-A33-10-265 (SEQ ID NO: 42) (d) in the IFN-gamma ELISPOT assay. As a result of measuring IFN-gamma by ELISA, IFN-gamma production by the CTL lines against target cells (C1R-A33) pulsed with Well #3 with FOXM1-A33-9-308 (SEQ ID NO: 2) (a), well #5 with FOXM1-A33-9-146 (SEQ ID NO: 7) (b), Well #6 with FOXM1-A33-10-391 (SEQ ID NO: 39) (c), or FOXM1-A33-10-265 (SEQ ID NO: 42) was observed (FIG. 2). Further, CTL clones were established by the limiting dilution method as described in the "Materials and methods" section above. As a result of measuring IFN-gamma by ELISA, CTL clones stimulated with FOXM1-A33-9-308 (SEQ ID NO: 2) (a) or FOXM1-A33-9-146 (SEQ ID NO: 7) (b) each showed a peptide-specific IFN-gamma production (FIG. 3).

IFN-Gamma Production Against Target Cells Expressing FOXM1 and HLA-A*33:03

IFN-gamma production of the FOXM1-A33-9-308 (SEQ ID NO: 2)-specific CTL clone against target cells expressing FOXM1 and HLA-A*33:03 was investigated. COS7 cells expressing both FOXM1 and HLA-A*33:03 were prepared as the target cell. COS7 cells expressing either one of FOXM1 and HLA-A*33:03 were prepared as the negative control cell. The FOXM1-A33-9-308 (SEQ ID NO: 2)-specific CTL clone showed IFN-gamma production against COS7 cells expressing both FOXM1 and HLA-A*33:03 (FIG. 4). On the other hand, a significant IFN-gamma production was not observed against the negative control cells. This clearly proves that FOXM1-A33-9-308 (SEQ ID NO: 2) is a peptide generated by antigen processing, and is presented on the cell surface with the HLA-A*33:03 molecule and recognized by CTLs. This result suggests that FOXM1-A33-9-308 (SEQ ID NO: 2) may be useful as a cancer vaccine for patients in whom FOXM1 expression is enhanced in cancer cells.

Homology Analysis of Antigen Peptides

It has been confirmed that FOXM1-A33-9-180 (SEQ ID NO: 1), FOXM1-A33-9-308 (SEQ ID NO: 2), FOXM1-A33-9-693 (SEQ ID NO: 3), FOXM1-A33-9-516 (SEQ ID NO: 6), FOXM1-A33-9-146 (SEQ ID NO: 7), FOXM1-A33-9-289 (SEQ ID NO: 11), FOXM1-A33-9-228 (SEQ ID NO: 12), FOXM1-A33-9-502 (SEQ ID NO: 17), FOXM1-A33-9-321 (SEQ ID NO: 18), FOXM1-A33-9-341 (SEQ ID NO: 20), FOXM1-A33-10-514 (SEQ ID NO: 22), FOXM1-A33-10-179 (SEQ ID NO: 24), FOXM1-A33-10-501 (SEQ ID NO: 26), FOXM1-A33-10-124 (SEQ ID NO: 32), FOXM1-A33-10-595 (SEQ ID NO: 33), FOXM1-A33-10-546 (SEQ ID NO: 36), FOXM1-A33-10-391 (SEQ ID NO: 39), FOXM1-A33-10-607 (SEQ ID NO: 41), FOXM1-A33-10-265 (SEQ ID NO: 42), FOXM1-A33-10-4 (SEQ ID NO: 45) and FOXM1-A33-10-388 (SEQ ID NO: 46) may induce CTLs showing peptide-specific IFN-gamma production. Thus, to confirm that the FOXM1-A33-9-180 (SEQ ID NO: 1), FOXM1-A33-9-308 (SEQ ID NO: 2), FOXM1-A33-9-693 (SEQ ID NO: 3), FOXM1-A33-9-516 (SEQ ID NO: 6), FOXM1-A33-9-146 (SEQ ID NO: 7), FOXM1-A33-9-289 (SEQ ID NO: 11), FOXM1-A33-9-228 (SEQ ID NO: 12), FOXM1-A33-9-502 (SEQ ID NO: 17), FOXM1-A33-9-321 (SEQ ID NO: 18), FOXM1-A33-9-341 (SEQ ID NO: 20), FOXM1-A33-10-514 (SEQ ID NO: 22), FOXM1-A33-10-179 (SEQ ID NO: 24), FOXM1-A33-10-501 (SEQ ID NO: 26), FOXM1-A33-10-124 (SEQ ID NO: 32), FOXM1-A33-10-595 (SEQ ID NO: 33), FOXM1-A33-10-546 (SEQ ID NO: 36), FOXM1-A33-10-391 (SEQ ID NO: 39), FOXM1-A33-10-607 (SEQ ID NO: 41), FOXM1-A33-10-265 (SEQ ID NO: 42), FOXM1-A33-10-4 (SEQ ID NO: 45) and FOXM1-A33-10-388 (SEQ ID NO: 46) sequences are only derived from FOXM1, homology analysis of the peptide sequences was performed using the BLAST algorithm (blast.ncbi.nlm.nih.gov/Blast.cgi). As a result, the FOXM1-A33-9-180 (SEQ ID NO: 1), FOXM1-A33-9-308 (SEQ ID NO: 2), FOXM1-A33-9-693 (SEQ ID NO: 3), FOXM1-A33-9-516 (SEQ ID NO: 6), FOXM1-A33-9-146 (SEQ ID NO: 7), FOXM1-A33-9-289 (SEQ ID NO: 11), FOXM1-A33-9-228 (SEQ ID NO: 12), FOXM1-A33-9-502 (SEQ ID NO: 17), FOXM1-A33-9-321 (SEQ ID NO: 18), FOXM1-A33-9-341 (SEQ ID NO: 20), FOXM1-A33-10-514 (SEQ ID NO: 22), FOXM1-A33-10-179 (SEQ ID NO: 24), FOXM1-A33-10-501 (SEQ ID NO: 26), FOXM1-A33-10-124 (SEQ ID NO: 32), FOXM1-A33-10-595 (SEQ ID NO: 33), FOXM1-A33-10-546 (SEQ ID NO: 36), FOXM1-A33-10-391 (SEQ ID NO: 39), FOXM1-A33-10-607 (SEQ ID NO: 41), FOXM1-A33-10-265 (SEQ ID NO: 42), FOXM1-A33-10-4 (SEQ ID NO: 45) and FOXM1-A33-10-388 (SEQ ID NO: 46) sequences were only found in FOXM1. Therefore, to the knowledge of the present inventors, these peptides are specific to FOXM1, so that there is almost no possibility that these peptides would elicit an unintended immune reaction against molecules other than FOXM1 that are already known to sensitize the human immune system.

In conclusion, novel FOXM1-derived HLA-A*33:03-restricted epitope peptides were identified. It was demonstrated that the FOXM1-derived epitope peptides are applicable for cancer immunotherapy.

Example 2

Materials and Methods

Cell Lines

C1R cells, an HLA-A- and HLA-B-negative human B lymphoblastoid cell line, and COS7 cells, an African green monkey kidney cell line, were purchased from ATCC.

Generation of Target Cells with Steady HLA-A*01:01 Expression

C1R cells (C1R-A01) that steadily express HLA-A*01:01 were used as cells that stimulate CTLs. A cDNA encoding the HLA-A*01:01 gene was amplified by PCR and incorporated into an expression vector. C1R cells into which the HLA-A*01:01 gene expression vector was introduced were cultured under drug selection for two weeks in medium containing G418 (Invitrogen). The G418-resistant C1R cell suspension was diluted, seeded in a 96-well plate, and further selectively cultured for 30 days in a G418-containing medium. The HLA-A*01:01 expression in C1R cells was verified by flow cytometric analysis.

Selection of FOXM1-Derived Peptides

FOXM1-derived 9mer and 10mer peptides that are expected to bind to the HLA-A*01:01 were determined using the binding prediction server "NetMHC 3.4" (www.cbs.dtu.dk/services/NetMHC-3.4/) (Buus S et al., Tissue Antigens. 2003, 62(5): 378-84; Nielsen M et al., Protein Sci. 2003, 12(5): 1007-17; Nielsen M et al., Bioinformatics. 2004, 20(9): 1388-97).

Peptide Synthesis

The peptides were synthesized by American Peptide Company (Sunnyvale, CA) according to a solid-phase synthesis method, and purified by reversed phase high-performance liquid chromatography (HPLC). The quality of the peptides (purity of 90% or higher) was guaranteed by HPLC and mass spectrometry. The peptides were dissolved with dimethylsulfoxide (final concentration: 20 mg/ml) and stored at −80 degrees C.

In Vitro CTL Induction

Monocyte-derived dendritic cells (DCs) were used as the antigen-presenting cell to induce a specific cytotoxic T lymphocyte (CTL) against peptides presented on human leukocyte antigens (HLAs). As already reported in literatures, DCs were generated in vitro (Nakahara S et al., Cancer Res 2003, 63(14): 4112-8). Specifically, peripheral-blood mononuclear cells (PBMCs) collected from healthy volunteers (HLA-A*01:01-positive) were seeded in plastic tissue culture dishes (Corning) to let the monocytes in the PBMCs adhere to the dishes. This was cultured in the presence of 1000 IU/ml granulocyte macrophage colony-stimulating factor (R&D System) and 1000 IU/ml interleukin (IL)-4 (R&D System) for seven days. An AIM-V medium (Invitrogen) containing 5% inactivated AB-type serum (ABS) was used as the medium. DCs that were induced to differentiate from monocytes using the cytokines were pulsed with 20 micro-g/ml of each synthesized peptide (37 degrees C., three hours). Peptide pulsing was carried out in an AIM-V medium containing 3 micro-g/ml beta 2-microglobulin. These peptide-pulsed DCs were inactivated by X-ray irradiation (20 Gy), mixed in a 1:20 ratio with autologous CD8 positive T cells obtained by using the CD8 Positive Isolation Kit (Invitrogen) ($1.5\times10^4$ DCs and $3\times10^5$ CD8 positive T cells), and cultured in a 48-well plate (Corning). Each well contained 0.5 ml of the 5% ABS/AIM-V medium, and IL-7 (R&D System) was added thereto (final concentration: 10 ng/ml). Two days after the start of the culture, IL-2 (Novartis) was added (final concentration: 20 IU/ml). On day 7 and day 14 of culture, the CD8 positive T cells were further stimulated with peptide-pulsed DCs. The DCs were prepared at the time of use by the same method as above. After day 21 (after three DC stimulations), IFN-gamma production against the peptide-pulsed C1R-A01 was confirmed using enzyme-linked immunospot (ELISPOT) assay (Tanaka H et al., Br J Cancer 2001, 84(1): 94-9; Umano Y et al., Br J Cancer 2001, 84(8): 1052-7; Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).

CTL Propagation Procedure

CTLs were propagated using methods similar to those reported by Riddell et al. (Walter E A et al., N Engl J Med 1995, 333(16): 1038-44; Riddell S R et al., Nat Med 1996, 2(2): 216-23). The CTLs were cultured in 25 ml 5% ABS/AIM-V medium together with two types of Mitomycin C-treated human B lymphoblastoid cell lines ($5\times10^6$ cells/25 ml medium each) and an anti-CD3 antibody (final concentration: 40 ng/ml). On the day after beginning of the culturing, IL-2 (final concentration: 120 IU/ml) was added to the culture. On days 5, 8 and 11, the medium was changed to a 5% ABS/AIM-V medium containing IL-2 (final concentration: 30 IU/ml) (Tanaka H et al., Br J Cancer 2001, 84(1): 94-9; Umano Y et al., Br J Cancer 2001, 84(8): 1052-7; Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).

Establishment of CTL Clones

After induction of CTLs in vitro, the CTLs were seeded onto 96-well round-bottomed microplates (Nalge Nunc International) at 1 cell/well or 10 cells/well. The CTLs were cultured with two types of Mitomycin C-treated human B lymphoblastoid cell lines ($1\times10^4$ cells/well each) in a total of 150 micro-l/well 5% ABS/AIM-V medium with an anti-CD3 antibody (final concentration: 30 ng/ml) and IL-2 (final concentration: 125 IU/ml). Ten days later, 50 micro-l 5% ABS/AIM-V medium containing 500 IU/ml IL-2 was added to the culture. On day 14 or after, CTLs that showed peptide-specific IFN-gamma production in an ELISPOT assay were propagated using the same method as described above (Uchida N et al., Clin Cancer Res 2004, 10(24): 8577-86; Suda T et al., Cancer Sci 2006, 97(5): 411-9; Watanabe T et al., Cancer Sci 2005, 96(8): 498-506).

Confirmation of IFN-Gamma Production

To confirm the peptide-specific IFN-gamma production of CTLs induced with a peptide, an IFN-gamma ELISPOT assay and an IFN-gamma ELISA were performed. Peptide-pulsed C1R-A01 ($1\times10^4$ cells/well) was prepared as the target cell. The IFN-gamma ELISPOT assay and IFN-gamma ELISA were performed according to the assay kit manufacturer's manual.

Preparation of Target Cells Forcibly Expressing FOXM1 and HLA-A*01:01

A cDNA encoding the FOXM1 or HLA-A*01:01 gene was amplified by PCR. The PCR-amplified product was each incorporated into an expression vector. Either or both of the FOXM1 gene-expressing vector and the HLA-A*01:01 gene-expressing vector were introduced into COS7 cells, which is a cell line negative for HLA, using Lipofectamine 2000 (Invitrogen). On the day after gene introduction, COS7 cells were detached and harvested using versene (Invitrogen), and used as the target cell for confirmation of IFN-gamma production ($5\times10^4$ cells/well).

Results

Selection of FOXM1-Derived HLA-A*01:01-Binding Peptides

Tables 2a and 2b show FOXM1-derived 9mer and 10mer peptides that have been predicted to bind to HLA-A*01:01 by "NetMHC 3.4" in the descending order of binding affinity. A total of 16 peptides that potentially have an HLA-A*01:01-binding ability was used as epitope peptide candidates.

TABLE 2a

FOM1-derived 9mer peptides predicted to bind to MA-A*01:01

| Start Position | Amino Acid Sequence | Kd (uM) | SEQ ID NO |
|---|---|---|---|
| 233 | VSERPPYSY | 73 | 48 |
| 539 | CVDEPELLF | 666 | 49 |
| 631 | ASDPLPDPL | 1807 | 50 |
| 703 | LTEGLVEDT | 6665 | 51 |
| 231 | NSVSERPPY | 6867 | 52 |
| 663 | SSEPLDLIS | 9729 | 53 |
| 392 | SSELARHSK | 18415 | 54 |
| 494 | PTPRPKKSY | 19761 | 55 |
| 341 | KTELPLGAR | 20899 | 20 |

Number at Start Position indicates what number from the N terminus of FOXM1 protein the first amino acid of the peptide corresponds to.

The dissociation constant [Kd (nM)] is calculated using "NetMHC3.4".

TABLE 2b

FOXM1-derived 10mer peptides predicted to bind to HLA-A*01:01

| Start Position | Amino Acid Sequence | Kd (nM) | SEQ ID NO |
|---|---|---|---|
| 566 | SSDPASQLSY | 15 | 56 |
| 263 | YTWIEDHFPY | 156 | 57 |
| 308 | WTIHPSANRY | 554 | 58 |
| 732 | SVSERPPYSY | 1482 | 59 |

TABLE 2b-continued

| FOXM1-derived 10mer peptides predicted to bind to HLA-A*01:01 | | | |
|---|---|---|---|
| Start Position | Amino Acid Sequence | Kd (nM) | SEQ ID NO |
| 663 | SSEPIDLISV | 10539 | 60 |
| 265 | WIEDHFPYFK | 18243 | 42 |
| 341 | KTELPLGARR | 26951 | 61 |

Number at Start Position indicates what number from the N terminus of FOXM1 protein the first amino acid of the peptide corresponds to.

The dissociation constant [Kd (nM)] is calculated using "NetMHC3.4".

Induction of CTLs by the FOXM1-Derived HLA-A*01:01-Restricted Peptides

FOXM1-derived peptide-specific CTLs were induced according to the protocol described in "Materials and methods". The peptide-specific IFN-gamma production was confirmed by an ELISPOT assay (FIG. 5). Peptide-specific IFN-gamma production was observed in

- Well #3 with FOXM1-A01-9-233 (SEQ ID NO: 48) (a),
- Well #3 with FOXM1-A01-9-539 (SEQ ID NO: 49) (b),
- Well #3 with FOXM1-A01-9-631 (SEQ ID NO: 50) (c),
- Well #2 with FOXM1-A01-9-231 (SEQ ID NO: 52) (d),
- Well #2 with FOXM1-A01-9-663 (SEQ ID NO: 53) (e),
- Well #5 with FOXM1-A01-9-494 (SEQ ID NO: 55) (f),
- Well #2 with FOXM1-A01-9-341 (SEQ ID NO: 20) (g),
- Well #1 with FOXM1-A01-10-566 (SEQ ID NO: 56) (h),
- Well #2 with FOXM1-A01-10-263 (SEQ ID NO: 57) (i),
- Well #4 with FOXM1-A01-10-308 (SEQ ID NO: 58) (j),
- Well #6 with FOXM1-A01-10-232 (SEQ ID NO: 59) (k),
- Well #6 with FOXM1-A01-10-663 (SEQ ID NO: 60) (l) and
- Well #6 with FOXM1-A01-10-341 (SEQ ID NO: 61) (m). Meanwhile, specific IFN-gamma production against other peptides shown in Tables 1a and 1b was not observed. For example, specific IFN-gamma production was not observed against FOXM1-A01-10-265 (SEQ ID NO: 42) (n). As a result, although all the peptides had the potential of binding to HLA-A*01:01, 13 peptides were selected as peptides having CTL-inducing ability.

Establishment of CTL Lines and Clones Specific to HLA-A*01:01-Restricted FOXM1-Derived Peptides CTL lines were established by propagating cells in Well #1 which showed specific IFN-gamma production against FOXM1-A01-10-566 (SEQ ID NO: 56) in the IFN-gamma ELISPOT assay. As a result of measuring IFN-gamma by ELISA, IFN-gamma production by the CTL lines against target cells (C1R-A01) pulsed with FOXM1-A01-10-566 (SEQ ID NO: 56) was observed (FIG. 6). Further, CTL clones were established by the limiting dilution method. As a result of measuring IFN-gamma by ELISA, CTL clones stimulated with FOXM1-A01-9-233 (SEQ ID NO: 48) (a) or FOXM1-A01-10-566 (SEQ ID NO: 56) (b) each showed a peptide-specific IFN-gamma production (FIG. 7).

IFN-Gamma Production Against Target Cells Expressing FOXM1 and HLA-A*01:01

IFN-gamma production of the FOXM1-A01-10-566 (SEQ ID NO: 56)-specific CTL clone against target cells expressing FOXM1 and HLA-A*01:01 was investigated. COS7 cells expressing both FOXM1 and HLA-A*01:01 were prepared as the target cell. COS7 cells expressing either one of FOXM1 and HLA-A*01:01 were prepared as the negative control cell. The FOXM1-A01-10-566 (SEQ ID NO: 56)-specific CTL clone showed IFN-gamma production against COS7 cells expressing both FOXM1 and HLA-A*01:01 (FIG. 8). On the other hand, a significant IFN-gamma production was not observed against the negative control cells. This clearly proves that FOXM1-A01-10-566 (SEQ ID NO: 56) is a peptide generated by antigen processing, and is presented on the cell surface with the HLA-A*01:01 molecule and recognized by CTLs. This result suggests that FOXM1-A01-10-566 (SEQ ID NO: 56) may be useful as a cancer vaccine for patients in whom FOXM1 expression is enhanced in cancer cells.

Homology Analysis of Antigen Peptides

It has been confirmed that FOXM1-A01-9-233 (SEQ ID NO: 48), FOXM1-A01-9-539 (SEQ ID NO: 49), FOXM1-A01-9-631 (SEQ ID NO: 50), FOXM1-A01-9-231 (SEQ ID NO: 52), FOXM1-A01-9-663 (SEQ ID NO: 53), FOXM1-A01-9-494 (SEQ ID NO: 55), FOXM1-A01-9-341 (SEQ ID NO: 20), FOXM1-A01-10-566 (SEQ ID NO: 56), FOXM1-A01-10-263 (SEQ ID NO: 57), FOXM1-A01-10-308 (SEQ ID NO: 58), FOXM1-A01-10-232 (SEQ ID NO: 59), FOXM1-A01-10-663 (SEQ ID NO: 60) and FOXM1-A01-10-341 (SEQ ID NO: 61) may induce CTLs showing peptide-specific IFN-gamma production. Thus, to confirm that the FOXM1-A01-9-233 (SEQ ID NO: 48), FOXM1-A01-9-539 (SEQ ID NO: 49), FOXM1-A01-9-631 (SEQ ID NO: 50), FOXM1-A01-9-231 (SEQ ID NO: 52), FOXM1-A01-9-663 (SEQ ID NO: 53), FOXM1-A01-9-494 (SEQ ID NO: 55), FOXM1-A01-9-341 (SEQ ID NO: 20), FOXM1-A01-10-566 (SEQ ID NO: 56), FOXM1-A01-10-263 (SEQ ID NO: 57), FOXM1-A01-10-308 (SEQ ID NO: 58), FOXM1-A01-10-232 (SEQ ID NO: 59), FOXM1-A01-10-663 (SEQ ID NO: 60) and FOXM1-A01-10-341 (SEQ ID NO: 61) sequences are only derived from FOXM1, homology analysis of the peptide sequences was performed using the BLAST algorithm (blast.ncbi.nlm.nih.gov/Blast.cgi). As a result, the FOXM1-A01-9-233 (SEQ ID NO: 48), FOXM1-A01-9-539 (SEQ ID NO: 49), FOXM1-A01-9-631 (SEQ ID NO: 50), FOXM1-A01-9-231 (SEQ ID NO: 52), FOXM1-A01-9-663 (SEQ ID NO: 53), FOXM1-A01-9-494 (SEQ ID NO: 55), FOXM1-A01-9-341 (SEQ ID NO: 20), FOXM1-A01-10-566 (SEQ ID NO: 56), FOXM1-A01-10-263 (SEQ ID NO: 57), FOXM1-A01-10-308 (SEQ ID NO: 58), FOXM1-A01-10-232 (SEQ ID NO: 59), FOXM1-A01-10-663 (SEQ ID NO: 60) and FOXM1-A01-10-341 (SEQ ID NO: 61) sequences were only found in FOXM1. Therefore, to the knowledge of the present inventors, these peptides are specific to FOXM1, so that there is almost no possibility that these peptides would elicit an unintended immune reaction against molecules other than FOXM1 that are already known to sensitize the human immune system. In conclusion, novel FOXM1-derived HLA-A*01:01-restricted epitope peptides were identified. It was demonstrated that the FOXM1-derived epitope peptides are applicable for cancer immunotherapy.

Example 3

Preparation of Emulsion Formulations

A peptide was dissolved in an injection solvent or sterile physiological saline to become 1.0 mg/ml to 10.0 mg/ml, and collected into a syringe. This was connected via a connector to a syringe filled with an IFA in an amount equivalent to an injection solvent or sterile physiological saline, and mixed by alternately pushing the syringe plungers of the two connected syringes. After several minutes of mixing, completion of the emulsion was assessed by the drop test method. The drop test method can be performed by dropping one drop of the mixed sample on water. The emulsion is assessed as completed when the sample dropped on water does not immediately diffuse in water; and the emulsion is assessed as incompleted when the sample dropped on water diffuses right away in water. When the emulsion is assessed as incompleted, further mixing is carried out to complete the emulsion. The completed emulsion can be administered to a cancer patient by subcutaneous injection. The cancer patient subject to administration can be selected from patients affected by acute myeloid leukemia (AML), bladder cancer, breast cancer, cervical cancer, cholangiocellular cancer, chronic myeloid leukemia (CML), colon cancer, esophageal cancer, gastric cancer, diffuse gastric cancer, liver cancer, non-small-cell lung cancer (NSCLC), lymphoma, osteosarcoma, ovary cancer, pancreatic cancer, prostate cancer, kidney cancer, small-cell lung cancer (SCLC), soft tissue tumor, testicular tumor or such.

Preparation of Freeze-Dried Formulations

A peptide was dissolved in an injection solvent to become 1.0 mg/ml to 10.0 mg/ml, and sterilized by filtration. This was filled into a sterilized vial, and half-capped with a sterilized rubber plug. After this vial was freeze-dried, it was completely capped and seamed with an aluminum cap to produce a freeze-dried formulation. When in use, an injection solvent or sterile physiological saline was injected into the vial to re-dissolve the freeze-dried powder. The re-dissolved solution in the vial was collected using a syringe, and the syringe was connected via a connector with a syringe filled with an IFA in an amount equivalent to the collected re-dissolved solution. The re-dissolved solution and IFA were mixed by alternately pushing the syringe plungers of the two connected syringes. After several minutes of mixing, completion of the emulsion was assessed by the drop test method. The completed emulsion can be administered to a cancer patient by subcutaneous injection. The cancer patient subject to administration can be selected from patients affected by acute myeloid leukemia (AML), bladder cancer, breast cancer, cervical cancer, cholangiocellular cancer, chronic myeloid leukemia (CML), colon cancer, esophageal cancer, gastric cancer, diffuse gastric cancer, liver cancer, non-small-cell lung cancer (NSCLC), lymphoma, osteosarcoma, ovary cancer, pancreatic cancer, prostate cancer, kidney cancer, small-cell lung cancer (SCLC), soft tissue tumor, testicular tumor or such.

INDUSTRIAL APPLICABILITY

The present invention provides FOXM1-derived novel HLA-A33-restricted and HLA-A01-restricted epitope peptides that induce a potent and specific anti-tumor immune response and thus have applicability for a wide range of cancer types. The peptides, compositions, APCs, and CTLs in the present invention can be used as a peptide vaccine for cancer expressing FOXM1, for example, acute myeloid leukemia (AML), bladder cancer, breast cancer, cervical cancer, cholangiocellular cancer, chronic myeloid leukemia (CML), colon cancer, esophageal cancer, gastric cancer, diffuse gastric cancer, liver cancer, non-small-cell lung cancer (NSCLC), lymphoma, osteosarcoma, ovary cancer, pancreatic cancer, prostate cancer, kidney cancer, small-cell lung cancer (SCLC), soft tissue tumor and testicular tumor.

While the present invention is herein described in detail and with respect to specific embodiments thereof, it is to be understood that the foregoing description is exemplary and explanatory in nature and is intended to illustrate the present invention and its preferred embodiments. Through routine experimentation, one skilled in the art will readily recognize that various changes and modifications can be made therein without departing from the spirit and scope of the present invention, the metes and bounds of which are defined by the appended claims.

The invention claimed is:

1. A composition comprising a pharmaceutically acceptable carrier, an adjuvant in an amount effective for enhancing cellular immunity, and at least one ingredient selected from the group consisting of (a) to (d) below:

(a) a peptide;

(b) a polynucleotide encoding the peptide in an expressible form;

(c) an antigen-presenting cell (APC) that presents on its cell surface a complex of the peptide and an HLA antigen; and (d) an exosome that presents on its surface a complex of the peptide and an HLA antigen;

wherein the peptide is not phosphorylated, wherein the peptide has cytotoxic T cell (CTL)-inducing ability in an HLA-A01-restrictive manner, and wherein the peptide comprises an amino acid sequence selected from the group consisting of:

(i) the amino acid sequence of SEQ ID NO: 56; and (ii) the amino acid sequence of SEQ ID NO: 56 into which one or two amino acid substitutions are introduced.

2. A method of inducing a CTL(s), which comprises a step selected from the group consisting of: (a) co-culturing a CD8-positive T cell(s) with an APC(s) that presents on its surface a complex of an HLA antigen and a peptide; and (b) co-culturing a CD8-positive T cell(s) with an exosome(s) that presents on its surface a complex of an HLA antigen and the peptide;

wherein the peptide is not phosphorylated, wherein the peptide has cytotoxic T cell (CTL)-inducing ability in an HLA-A01-restrictive manner, and wherein the peptide comprises an amino acid sequence selected from the group consisting of:

(i) the amino acid sequence of SEQ ID NO: 56, and (ii) the amino acid sequence of SEQ ID NO: 56 into which one or two amino acid substitutions are introduced.

3. A method of inducing an immune response against cancer, which comprises administering to a subject at least one ingredient selected from the group consisting of (a) to (d) below: (a) a peptide; (b) a polynucleotide encoding the peptide in an expressible form; (c) an APC that presents on its cell surface a complex of the peptide and an HLA antigen; and (d) an exosome that presents on its surface a complex of the peptide and an HLA antigen;

wherein the peptide is not phosphorylated, wherein the peptide has cytotoxic T cell (CTL)-inducing ability in an HLA-A01-restrictive manner, and wherein the peptide comprises an amino acid sequence selected from the group consisting of:

(i) the amino acid sequence of SEQ ID NO: 56, and (ii) the amino acid sequence of SEQ ID NO: 56 into which one or two amino acid substitutions are introduced.

4. A method of treating cancer, which comprises administering to a subject at least one ingredient selected from the group consisting of (a) to (d) below: (a) a peptide; (b) a polynucleotide encoding the peptide in an expressible form; (c) an APC that presents on its cell surface a complex of the peptide and an HLA antigen; and (d) an exosome that presents on its surface a complex of the peptide and an HLA antigen;

wherein the peptide is not phosphorylated, wherein the peptide has cytotoxic T cell (CTL)-inducing ability in an HLA-A01-restrictive manner, and wherein the peptide comprises an amino acid sequence selected from the group consisting of:

(i) the amino acid sequence of SEQ ID NO: 56, and (ii) the amino acid sequence of SEQ ID NO: 56 into which one or two amino acid substitutions are introduced.

5. An emulsion comprising a peptide, a water-soluble carrier and an oil adjuvant in an amount effective for enhancing cellular immunity, wherein the peptide is not phosphorylated, wherein the peptide has cytotoxic T cell (CTL)-inducing ability in an HLA-A01-restrictive manner, and wherein the peptide comprises an amino acid sequence selected from the group consisting of:

(i) the amino acid sequence of SEQ ID NO: 56, and (ii) the amino acid sequence of SEQ ID NO: 56 into which one or two amino acid substitutions are introduced.

6. The composition of claim 1, wherein the peptide consists of the amino acid sequence of SEQ ID NO: 56.

7. The method of claim 2, wherein the peptide consists of the amino acid sequence of SEQ ID NO: 56.

8. The method of claim 3, wherein the peptide consists of the amino acid sequence of SEQ ID NO: 56.

9. The method of claim 4, wherein the peptide consists of the amino acid sequence of SEQ ID NO: 56.

10. The emulsion of claim 5, wherein the peptide consists of the amino acid sequence of SEQ ID NO: 56.

* * * * *

```
                    SEQUENCE LISTING

<160> NUMBER OF SEQ ID NOS: 76

<210> SEQ ID NO 1
<211> LENGTH: 9
<212> TYPE: PRT
<213> ORGANISM: Artificial Sequence
<220> FEATURE:
<223> OTHER INFORMATION: a peptide derived from FOXM1

<400> SEQUENCE: 1

Ser Leu Ser Asn Ile Gln Trp Leu Arg
1               5


<210> SEQ ID NO 2
<211> LENGTH: 9
<212> TYPE: PRT
<213> ORGANISM: Artificial Sequence
<220> FEATURE:
<223> OTHER INFORMATION: a peptide derived from FOXM1

<400> SEQUENCE: 2

Trp Thr Ile His Pro Ser Ala Asn Arg
1               5


<210> SEQ ID NO 3
<211> LENGTH: 9
<212> TYPE: PRT
```

<213> ORGANISM: Artificial Sequence
<220> FEATURE:
<223> OTHER INFORMATION: a peptide derived from FOXM1

<400> SEQUENCE: 3

Gln Val Ser Gly Leu Ala Ala Asn Arg
1               5

<210> SEQ ID NO 4
<211> LENGTH: 9
<212> TYPE: PRT
<213> ORGANISM: Artificial Sequence
<220> FEATURE:
<223> OTHER INFORMATION: a peptide derived from FOXM1

<400> SEQUENCE: 4

Met Ser Ser Asp Gly Leu Gly Ser Arg
1               5

<210> SEQ ID NO 5
<211> LENGTH: 9
<212> TYPE: PRT
<213> ORGANISM: Artificial Sequence
<220> FEATURE:
<223> OTHER INFORMATION: a peptide derived from FOXM1

<400> SEQUENCE: 5

Met Leu Val Ile Gln His Arg Glu Arg
1               5

<210> SEQ ID NO 6
<211> LENGTH: 9
<212> TYPE: PRT
<213> ORGANISM: Artificial Sequence
<220> FEATURE:
<223> OTHER INFORMATION: a peptide derived from FOXM1

<400> SEQUENCE: 6

Leu Val Ile Gln His Arg Glu Arg Arg
1               5

<210> SEQ ID NO 7
<211> LENGTH: 9
<212> TYPE: PRT
<213> ORGANISM: Artificial Sequence
<220> FEATURE:
<223> OTHER INFORMATION: a peptide derived from FOXM1

<400> SEQUENCE: 7

Ala Ala Arg Asp Val Asn Leu Pro Arg
1               5

<210> SEQ ID NO 8
<211> LENGTH: 9
<212> TYPE: PRT
<213> ORGANISM: Artificial Sequence
<220> FEATURE:
<223> OTHER INFORMATION: a peptide derived from FOXM1

<400> SEQUENCE: 8

Thr Leu Gly Pro Lys Pro Ala Ala Arg
1               5

<210> SEQ ID NO 9
<211> LENGTH: 9
<212> TYPE: PRT
<213> ORGANISM: Artificial Sequence
<220> FEATURE:
<223> OTHER INFORMATION: a peptide derived from FOXM1

<400> SEQUENCE: 9

Ser Leu Met Ser Ser Glu Leu Ala Arg
1 5

<210> SEQ ID NO 10
<211> LENGTH: 9
<212> TYPE: PRT
<213> ORGANISM: Artificial Sequence
<220> FEATURE:
<223> OTHER INFORMATION: a peptide derived from FOXM1

<400> SEQUENCE: 10

Gln Phe Ala Ile Asn Ser Thr Glu Arg
1 5

<210> SEQ ID NO 11
<211> LENGTH: 9
<212> TYPE: PRT
<213> ORGANISM: Artificial Sequence
<220> FEATURE:
<223> OTHER INFORMATION: a peptide derived from FOXM1

<400> SEQUENCE: 11

Leu Ser Leu His Asp Met Phe Val Arg
1 5

<210> SEQ ID NO 12
<211> LENGTH: 9
<212> TYPE: PRT
<213> ORGANISM: Artificial Sequence
<220> FEATURE:
<223> OTHER INFORMATION: a peptide derived from FOXM1

<400> SEQUENCE: 12

Ser Trp Gln Asn Ser Val Ser Glu Arg
1 5

<210> SEQ ID NO 13
<211> LENGTH: 9
<212> TYPE: PRT
<213> ORGANISM: Artificial Sequence
<220> FEATURE:
<223> OTHER INFORMATION: a peptide derived from FOXM1

<400> SEQUENCE: 13

Thr Gln Thr Ser Tyr Asp Ala Lys Arg
1 5

<210> SEQ ID NO 14
<211> LENGTH: 9
<212> TYPE: PRT
<213> ORGANISM: Artificial Sequence
<220> FEATURE:
<223> OTHER INFORMATION: a peptide derived from FOXM1

<400> SEQUENCE: 14

Asp Ser Ser Gln Ser Pro Thr Pro Arg
1 5

<210> SEQ ID NO 15
<211> LENGTH: 9
<212> TYPE: PRT
<213> ORGANISM: Artificial Sequence
<220> FEATURE:

<223> OTHER INFORMATION: a peptide derived from FOXM1

<400> SEQUENCE: 15

Phe Pro Tyr Phe Lys His Ile Ala Lys
1               5

<210> SEQ ID NO 16
<211> LENGTH: 9
<212> TYPE: PRT
<213> ORGANISM: Artificial Sequence
<220> FEATURE:
<223> OTHER INFORMATION: a peptide derived from FOXM1

<400> SEQUENCE: 16

Gln Val Lys Val Glu Glu Pro Ser Arg
1               5

<210> SEQ ID NO 17
<211> LENGTH: 9
<212> TYPE: PRT
<213> ORGANISM: Artificial Sequence
<220> FEATURE:
<223> OTHER INFORMATION: a peptide derived from FOXM1

<400> SEQUENCE: 17

Tyr Ser Gly Leu Arg Ser Pro Thr Arg
1               5

<210> SEQ ID NO 18
<211> LENGTH: 9
<212> TYPE: PRT
<213> ORGANISM: Artificial Sequence
<220> FEATURE:
<223> OTHER INFORMATION: a peptide derived from FOXM1

<400> SEQUENCE: 18

Asp Gln Val Phe Lys Gln Gln Lys Arg
1               5

<210> SEQ ID NO 19
<211> LENGTH: 9
<212> TYPE: PRT
<213> ORGANISM: Artificial Sequence
<220> FEATURE:
<223> OTHER INFORMATION: a peptide derived from FOXM1

<400> SEQUENCE: 19

Ser Glu Leu Ala Arg His Ser Lys Arg
1               5

<210> SEQ ID NO 20
<211> LENGTH: 9
<212> TYPE: PRT
<213> ORGANISM: Artificial Sequence
<220> FEATURE:
<223> OTHER INFORMATION: a peptide derived from FOXM1

<400> SEQUENCE: 20

Lys Thr Glu Leu Pro Leu Gly Ala Arg
1               5

<210> SEQ ID NO 21
<211> LENGTH: 9
<212> TYPE: PRT
<213> ORGANISM: Artificial Sequence
<220> FEATURE:
<223> OTHER INFORMATION: a peptide derived from FOXM1

<400> SEQUENCE: 21

Phe Ser Glu Gly Pro Ser Thr Ser Arg
1 5

<210> SEQ ID NO 22
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 22

Glu Met Leu Val Ile Gln His Arg Glu Arg
1 5 10

<210> SEQ ID NO 23
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 23

Glu Thr Leu Gly Pro Lys Pro Ala Ala Arg
1 5 10

<210> SEQ ID NO 24
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 24

Asn Ser Leu Ser Asn Ile Gln Trp Leu Arg
1 5 10

<210> SEQ ID NO 25
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 25

Asn Leu Ser Leu His Asp Met Phe Val Arg
1 5 10

<210> SEQ ID NO 26
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 26

Ser Tyr Ser Gly Leu Arg Ser Pro Thr Arg
1 5 10

<210> SEQ ID NO 27
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 27

Met Leu Val Ile Gln His Arg Glu Arg Arg
1 5 10

<210> SEQ ID NO 28
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 28

Phe Trp Thr Ile His Pro Ser Ala Asn Arg
1 5 10

<210> SEQ ID NO 29
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 29

His Ser Lys Arg Val Arg Ile Ala Pro Lys
1 5 10

<210> SEQ ID NO 30
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 30

Ile Gln Phe Ala Ile Asn Ser Thr Glu Arg
1 5 10

<210> SEQ ID NO 31
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 31

His Phe Pro Tyr Phe Lys His Ile Ala Lys
1 5 10

<210> SEQ ID NO 32
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 32

Gln Thr Gln Thr Ser Tyr Asp Ala Lys Arg
1 5 10

<210> SEQ ID NO 33
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 33

Ser Thr Pro Ser Lys Ser Val Leu Pro Arg
1 5 10

<210> SEQ ID NO 34
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 34

Glu Leu Ala Arg His Ser Lys Arg Val Arg
1 5 10

<210> SEQ ID NO 35
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 35

Phe Ala Ile Asn Ser Thr Glu Arg Lys Arg
1 5 10

<210> SEQ ID NO 36
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 36

Leu Phe Ser Glu Gly Pro Ser Thr Ser Arg
1 5 10

<210> SEQ ID NO 37
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 37

Ser Ser Glu Leu Ala Arg His Ser Lys Arg
1 5 10

<210> SEQ ID NO 38
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 38

Ala Ser Trp Gln Asn Ser Val Ser Glu Arg
1 5 10

<210> SEQ ID NO 39
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 39

Met Ser Ser Glu Leu Ala Arg His Ser Lys
1 5 10

<210> SEQ ID NO 40
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 40

Gln Gln Lys Arg Pro Asn Pro Glu Leu Arg
1 5 10

<210> SEQ ID NO 41
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 41

Glu Ser Trp Arg Leu Thr Pro Pro Ala Lys
1 5 10

<210> SEQ ID NO 42
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 42

Trp Ile Glu Asp His Phe Pro Tyr Phe Lys
1 5 10

<210> SEQ ID NO 43
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 43

Arg Pro Lys Lys Ser Tyr Ser Gly Leu Arg
1 5 10

<210> SEQ ID NO 44
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 44

Glu Trp Pro Ser Pro Ala Pro Ser Phe Lys
1 5 10

<210> SEQ ID NO 45
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 45

Ser Pro Arg Arg Pro Leu Ile Leu Lys Arg 1 5 10

<210> SEQ ID NO 46
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 46

Ala Ser Leu Met Ser Ser Glu Leu Ala Arg
1 5 10

<210> SEQ ID NO 47
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 47

Ser Ala Pro Pro Leu Glu Ser Pro Gln Arg
1 5 10

<210> SEQ ID NO 48
<211> LENGTH: 9
<212> TYPE: PRT
<213> ORGANISM: Artificial Sequence
<220> FEATURE:
<223> OTHER INFORMATION: a peptide derived from FOXM1

<400> SEQUENCE: 48

Val Ser Glu Arg Pro Pro Tyr Ser Tyr
1 5

<210> SEQ ID NO 49
<211> LENGTH: 9
<212> TYPE: PRT
<213> ORGANISM: Artificial Sequence
<220> FEATURE:
<223> OTHER INFORMATION: a peptide derived from FOXM1

<400> SEQUENCE: 49

Cys Val Asp Glu Pro Glu Leu Leu Phe
1 5

<210> SEQ ID NO 50
<211> LENGTH: 9
<212> TYPE: PRT
<213> ORGANISM: Artificial Sequence
<220> FEATURE:
<223> OTHER INFORMATION: a peptide derived from FOXM1

<400> SEQUENCE: 50

Ala Ser Asp Pro Leu Pro Asp Pro Leu
1 5

<210> SEQ ID NO 51
<211> LENGTH: 9
<212> TYPE: PRT
<213> ORGANISM: Artificial Sequence
<220> FEATURE:
<223> OTHER INFORMATION: a peptide derived from FOXM1

<400> SEQUENCE: 51

Leu Thr Glu Gly Leu Val Leu Asp Thr
1 5

<210> SEQ ID NO 52
<211> LENGTH: 9
<212> TYPE: PRT
<213> ORGANISM: Artificial Sequence
<220> FEATURE:
<223> OTHER INFORMATION: a peptide derived from FOXM1

<400> SEQUENCE: 52

Asn Ser Val Ser Glu Arg Pro Pro Tyr
1               5

<210> SEQ ID NO 53
<211> LENGTH: 9
<212> TYPE: PRT
<213> ORGANISM: Artificial Sequence
<220> FEATURE:
<223> OTHER INFORMATION: a peptide derived from FOXM1

<400> SEQUENCE: 53

Ser Ser Glu Pro Leu Asp Leu Ile Ser
1               5

<210> SEQ ID NO 54
<211> LENGTH: 9
<212> TYPE: PRT
<213> ORGANISM: Artificial Sequence
<220> FEATURE:
<223> OTHER INFORMATION: a peptide derived from FOXM1

<400> SEQUENCE: 54

Ser Ser Glu Leu Ala Arg His Ser Lys
1               5

<210> SEQ ID NO 55
<211> LENGTH: 9
<212> TYPE: PRT
<213> ORGANISM: Artificial Sequence
<220> FEATURE:
<223> OTHER INFORMATION: a peptide derived from FOXM1

<400> SEQUENCE: 55

Pro Thr Pro Arg Pro Lys Lys Ser Tyr
1               5

<210> SEQ ID NO 56
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 56

Ser Ser Asp Pro Ala Ser Gln Leu Ser Tyr
1               5                   10

<210> SEQ ID NO 57
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 57

Tyr Thr Trp Ile Glu Asp His Phe Pro Tyr
1               5                   10

<210> SEQ ID NO 58
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 58

Trp Thr Ile His Pro Ser Ala Asn Arg Tyr
1 5 10

<210> SEQ ID NO 59
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 59

Ser Val Ser Glu Arg Pro Pro Tyr Ser Tyr
1 5 10

<210> SEQ ID NO 60
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 60

Ser Ser Glu Pro Leu Asp Leu Ile Ser Val
1 5 10

<210> SEQ ID NO 61
<211> LENGTH: 10
<212> TYPE: PRT
<213> ORGANISM: Artificial Sequence
<220> FEATURE:
<223> OTHER INFORMATION: a peptide derived from FOXM1

<400> SEQUENCE: 61

Lys Thr Glu Leu Pro Leu Gly Ala Arg Arg
1 5 10

<210> SEQ ID NO 62
<211> LENGTH: 22
<212> TYPE: DNA
<213> ORGANISM: Artificial Sequence
<220> FEATURE:
<223> OTHER INFORMATION: a PCR primer for the TCR analysis

<400> SEQUENCE: 62
gtctaccagg cattcgcttc at 22

<210> SEQ ID NO 63
<211> LENGTH: 24
<212> TYPE: DNA
<213> ORGANISM: Artificial Sequence
<220> FEATURE:
<223> OTHER INFORMATION: a PCR primer for the TCR analysis

<400> SEQUENCE: 63
tcagctggac cacagccgca gcgt 24

<210> SEQ ID NO 64
<211> LENGTH: 21

```
<212> TYPE: DNA
<213> ORGANISM: Artificial Sequence
<220> FEATURE:
<223> OTHER INFORMATION: a PCR primer for the TCR analysis

<400> SEQUENCE: 64

tcagaaatcc tttctcttga c                                              21


<210> SEQ ID NO 65
<211> LENGTH: 24
<212> TYPE: DNA
<213> ORGANISM: Artificial Sequence
<220> FEATURE:
<223> OTHER INFORMATION: a PCR primer for the TCR analysis

<400> SEQUENCE: 65

ctagcctctg gaatcctttc tctt                                           24


<210> SEQ ID NO 66
<211> LENGTH: 3506
<212> TYPE: DNA
<213> ORGANISM: Homo sapiens
<220> FEATURE:
<221> NAME/KEY: CDS
<222> LOCATION: (284)..(2530)

<400> SEQUENCE: 66

tttcaaacag cggaacaaac tgaaagctcc ggtgccagac cccacccccg gccccggccc     60

gggacccccct ccccctcccgg gatccccccgg ggttcccacc ccgcccgcac cgccggggac    120

ccggccggtc cggcgcgagc ccccgtccgg ggccctggct cggcccccag gttggaggag    180

cccggagccc gccttcggag ctacggccta acggcggcgg cgactgcagt ctggagggtc    240

cacacttgtg attctcaatg gagagtgaaa acgcagattc ata atg aaa act agc      295
                                            Met Lys Thr Ser
                                            1

ccc cgt cgg cca ctg att ctc aaa aga cgg agg ctg ccc ctt cct gtt      343
Pro Arg Arg Pro Leu Ile Leu Lys Arg Arg Arg Leu Pro Leu Pro Val
5                   10                  15                  20

caa aat gcc cca agt gaa aca tca gag gag gaa cct aag aga tcc cct      391
Gln Asn Ala Pro Ser Glu Thr Ser Glu Glu Glu Pro Lys Arg Ser Pro
                25                  30                  35

gcc caa cag gag tct aat caa gca gag gcc tcc aag gaa gtg gca gag      439
Ala Gln Gln Glu Ser Asn Gln Ala Glu Ala Ser Lys Glu Val Ala Glu
            40                  45                  50

tcc aac tct tgc aag ttt cca gct ggg atc aag att att aac cac ccc      487
Ser Asn Ser Cys Lys Phe Pro Ala Gly Ile Lys Ile Ile Asn His Pro
        55                  60                  65

acc atg ccc aac acg caa gta gtg gcc atc ccc aac aat gct aat att      535
Thr Met Pro Asn Thr Gln Val Val Ala Ile Pro Asn Asn Ala Asn Ile
    70                  75                  80

cac agc atc atc aca gca ctg act gcc aag gga aaa gag agt ggc agt      583
His Ser Ile Ile Thr Ala Leu Thr Ala Lys Gly Lys Glu Ser Gly Ser
85                  90                  95                  100

agt ggg ccc aac aaa ttc atc ctc atc agc tgt ggg gga gcc cca act      631
Ser Gly Pro Asn Lys Phe Ile Leu Ile Ser Cys Gly Gly Ala Pro Thr
                105                 110                 115

cag cct cca gga ctc cgg cct caa acc caa acc agc tat gat gcc aaa      679
Gln Pro Pro Gly Leu Arg Pro Gln Thr Gln Thr Ser Tyr Asp Ala Lys
            120                 125                 130

agg aca gaa gtg acc ctg gag acc ttg gga cca aaa cct gca gct agg      727
Arg Thr Glu Val Thr Leu Glu Thr Leu Gly Pro Lys Pro Ala Ala Arg
        135                 140                 145
```

```
gat gtg aat ctt cct aga cca cct gga gcc ctt tgc gag cag aaa cgg      775
Asp Val Asn Leu Pro Arg Pro Pro Gly Ala Leu Cys Glu Gln Lys Arg
    150                 155                 160

gag acc tgt gca gat ggt gag gca gca ggc tgc act atc aac aat agc      823
Glu Thr Cys Ala Asp Gly Glu Ala Ala Gly Cys Thr Ile Asn Asn Ser
165                 170                 175                 180

cta tcc aac atc cag tgg ctt cga aag atg agt tct gat gga ctg ggc      871
Leu Ser Asn Ile Gln Trp Leu Arg Lys Met Ser Ser Asp Gly Leu Gly
                185                 190                 195

tcc cgc agc atc aag caa gag atg gag gaa aag gag aat tgt cac ctg      919
Ser Arg Ser Ile Lys Gln Glu Met Glu Glu Lys Glu Asn Cys His Leu
            200                 205                 210

gag cag cga cag gtt aag gtt gag gag cct tcg aga cca tca gcg tcc      967
Glu Gln Arg Gln Val Lys Val Glu Glu Pro Ser Arg Pro Ser Ala Ser
        215                 220                 225

tgg cag aac tct gtg tct gag cgg cca ccc tac tct tac atg gcc atg     1015
Trp Gln Asn Ser Val Ser Glu Arg Pro Pro Tyr Ser Tyr Met Ala Met
    230                 235                 240

ata caa ttc gcc atc aac agc act gag agg aag cgc atg act ttg aaa     1063
Ile Gln Phe Ala Ile Asn Ser Thr Glu Arg Lys Arg Met Thr Leu Lys
245                 250                 255                 260

gac atc tat acg tgg att gag gac cac ttt ccc tac ttt aag cac att     1111
Asp Ile Tyr Thr Trp Ile Glu Asp His Phe Pro Tyr Phe Lys His Ile
                265                 270                 275

gcc aag cca ggc tgg aag aac tcc atc cgc cac aac ctt tcc ctg cac     1159
Ala Lys Pro Gly Trp Lys Asn Ser Ile Arg His Asn Leu Ser Leu His
            280                 285                 290

gac atg ttt gtc cgg gag acg tct gcc aat ggc aag gtc tcc ttc tgg     1207
Asp Met Phe Val Arg Glu Thr Ser Ala Asn Gly Lys Val Ser Phe Trp
        295                 300                 305

acc att cac ccc agt gcc aac cgc tac ttg aca ttg gac cag gtg ttt     1255
Thr Ile His Pro Ser Ala Asn Arg Tyr Leu Thr Leu Asp Gln Val Phe
    310                 315                 320

aag cag cag aaa cga ccg aat cca gag ctc cgc cgg aac atg acc atc     1303
Lys Gln Gln Lys Arg Pro Asn Pro Glu Leu Arg Arg Asn Met Thr Ile
325                 330                 335                 340

aaa acc gaa ctc ccc ctg ggc gca cgg cgg aag atg aag cca ctg cta     1351
Lys Thr Glu Leu Pro Leu Gly Ala Arg Arg Lys Met Lys Pro Leu Leu
                345                 350                 355

cca cgg gtc agc tca tac ctg gta cct atc cag ttc ccg gtg aac cag     1399
Pro Arg Val Ser Ser Tyr Leu Val Pro Ile Gln Phe Pro Val Asn Gln
            360                 365                 370

tca ctg gtg ttg cag ccc tcg gtg aag gtg cca ttg ccc ctg gcg gct     1447
Ser Leu Val Leu Gln Pro Ser Val Lys Val Pro Leu Pro Leu Ala Ala
        375                 380                 385

tcc ctc atg agc tca gag ctt gcc cgc cat agc aag cga gtc cgc att     1495
Ser Leu Met Ser Ser Glu Leu Ala Arg His Ser Lys Arg Val Arg Ile
    390                 395                 400

gcc ccc aag gtg ctg cta gct gag gag ggg ata gct cct ctt tct tct     1543
Ala Pro Lys Val Leu Leu Ala Glu Glu Gly Ile Ala Pro Leu Ser Ser
405                 410                 415                 420

gca gga cca ggg aaa gag gag aaa ctc ctg ttt gga gaa ggg ttt tct     1591
Ala Gly Pro Gly Lys Glu Glu Lys Leu Leu Phe Gly Glu Gly Phe Ser
                425                 430                 435

cct ttg ctt cca gtt cag act atc aag gag gaa gaa atc cag cct ggg     1639
Pro Leu Leu Pro Val Gln Thr Ile Lys Glu Glu Glu Ile Gln Pro Gly
            440                 445                 450

gag gaa atg cca cac tta gcg aga ccc atc aaa gtg gag agc cct ccc     1687
Glu Glu Met Pro His Leu Ala Arg Pro Ile Lys Val Glu Ser Pro Pro
```

```
        455                 460                 465

ttg gaa gag tgg ccc tcc ccg gcc cca tct ttc aaa gag gaa tca tct     1735
Leu Glu Glu Trp Pro Ser Pro Ala Pro Ser Phe Lys Glu Glu Ser Ser
    470                 475                 480

cac tcc tgg gag gat tcg tcc caa tct ccc acc cca aga ccc aag aag     1783
His Ser Trp Glu Asp Ser Ser Gln Ser Pro Thr Pro Arg Pro Lys Lys
485                 490                 495                 500

tcc tac agt ggg ctt agg tcc cca acc cgg tgt gtc tcg gaa atg ctt     1831
Ser Tyr Ser Gly Leu Arg Ser Pro Thr Arg Cys Val Ser Glu Met Leu
            505                 510                 515

gtg att caa cac agg gag agg agg gag agg agc cgg tct cgg agg aaa     1879
Val Ile Gln His Arg Glu Arg Arg Glu Arg Ser Arg Ser Arg Arg Lys
            520                 525                 530

cag cat cta ctg cct ccc tgt gtg gat gag ccg gag ctg ctc ttc tca     1927
Gln His Leu Leu Pro Pro Cys Val Asp Glu Pro Glu Leu Leu Phe Ser
        535                 540                 545

gag ggg ccc agt act tcc cgc tgg gcc gca gag ctc ccg ttc cca gca     1975
Glu Gly Pro Ser Thr Ser Arg Trp Ala Ala Glu Leu Pro Phe Pro Ala
    550                 555                 560

gac tcc tct gac cct gcc tcc cag ctc agc tac tcc cag gaa gtg gga     2023
Asp Ser Ser Asp Pro Ala Ser Gln Leu Ser Tyr Ser Gln Glu Val Gly
565                 570                 575                 580

gga cct ttt aag aca ccc att aag gaa acg ctg ccc atc tcc tcc acc     2071
Gly Pro Phe Lys Thr Pro Ile Lys Glu Thr Leu Pro Ile Ser Ser Thr
            585                 590                 595

ccg agc aaa tct gtc ctc ccc aga acc cct gaa tcc tgg agg ctc acg     2119
Pro Ser Lys Ser Val Leu Pro Arg Thr Pro Glu Ser Trp Arg Leu Thr
            600                 605                 610

ccc cca gcc aaa gta ggg gga ctg gat ttc agc cca gta caa acc tcc     2167
Pro Pro Ala Lys Val Gly Gly Leu Asp Phe Ser Pro Val Gln Thr Ser
        615                 620                 625

cag ggt gcc tct gac ccc ttg cct gac ccc ctg ggg ctg atg gat ctc     2215
Gln Gly Ala Ser Asp Pro Leu Pro Asp Pro Leu Gly Leu Met Asp Leu
    630                 635                 640

agc acc act ccc ttg caa agt gct ccc ccc ctt gaa tca ccg caa agg     2263
Ser Thr Thr Pro Leu Gln Ser Ala Pro Pro Leu Glu Ser Pro Gln Arg
645                 650                 655                 660

ctc ctc agt tca gaa ccc tta gac ctc atc tcc gtc ccc ttt ggc aac     2311
Leu Leu Ser Ser Glu Pro Leu Asp Leu Ile Ser Val Pro Phe Gly Asn
            665                 670                 675

tct tct ccc tca gat ata gac gtc ccc aag cca ggc tcc ccg gag cca     2359
Ser Ser Pro Ser Asp Ile Asp Val Pro Lys Pro Gly Ser Pro Glu Pro
            680                 685                 690

cag gtt tct ggc ctt gca gcc aat cgt tct ctg aca gaa ggc ctg gtc     2407
Gln Val Ser Gly Leu Ala Ala Asn Arg Ser Leu Thr Glu Gly Leu Val
        695                 700                 705

ctg gac aca atg aat gac agc ctc agc aag atc ctg ctg gac atc agc     2455
Leu Asp Thr Met Asn Asp Ser Leu Ser Lys Ile Leu Leu Asp Ile Ser
    710                 715                 720

ttt cct ggc ctg gac gag gac cca ctg ggc cct gac aac atc aac tgg     2503
Phe Pro Gly Leu Asp Glu Asp Pro Leu Gly Pro Asp Asn Ile Asn Trp
725                 730                 735                 740

tcc cag ttt att cct gag cta cag tag agccctgccc ttgcccctgt           2550
Ser Gln Phe Ile Pro Glu Leu Gln
            745

gctcaagctg tccaccatcc cgggcactcc aaggctcagt gcaccccaag cctctgagtg   2610

aggacagcag gcagggactg ttctgctcct catagctccc tgctgcctga ttatgcaaaa   2670

gtagcagtca caccctagcc actgctggga ccttgtgttc cccaagagta tctgattcct   2730
```

```
ctgctgtccc tgccaggagc tgaagggtgg gaacaacaaa ggcaatggtg aaaagagatt   2790

aggaaccccc cagcctgttt ccattctctg cccagcagtc tcttaccttc cctgatcttt   2850

gcagggtggt ccgtgtaaat agtataaatt ctccaaatta tcctctaatt ataaatgtaa   2910

gcttatttcc ttagatcatt atccagagac tgccagaagg tgggtaggat gacctggggt   2970

ttcaattgac ttctgttcct tgcttttagt tttgatagaa gggaagacct gcagtgcacg   3030

gtttcttcca ggctgaggta cctggatctt gggttcttca ctgcagggac ccagacaagt   3090

ggatctgctt gccagagtcc tttttgcccc tccctgccac ctccccgtgt ttccaagtca   3150

gctttcctgc aagaagaaat cctggttaaa aaagtctttt gtattgggtc aggagttgaa   3210

tttggggtgg gaggatggat gcaactgaag cagagtgtgg gtgcccagat gtgcgctatt   3270

agatgtttct ctgataatgt ccccaatcat accagggaga ctggcattga cgagaactca   3330

ggtggaggct tgagaaggcc gaaagggccc ctgacctgcc tggcttcctt agcttgcccc   3390

tcagctttgc aaagagccac cctaggcccc agctgaccgc atgggtgtga gccagcttga   3450

gaacactaac tactcaataa aagcgaaggt ggacatgaaa aaaaaaaaaa aaaaaa       3506
```

<210> SEQ ID NO 67
<211> LENGTH: 748
<212> TYPE: PRT
<213> ORGANISM: Homo sapiens

<400> SEQUENCE: 67

```
Met Lys Thr Ser Pro Arg Arg Pro Leu Ile Leu Lys Arg Arg Arg Leu
1               5                   10                  15

Pro Leu Pro Val Gln Asn Ala Pro Ser Glu Thr Ser Glu Glu Glu Pro
            20                  25                  30

Lys Arg Ser Pro Ala Gln Gln Glu Ser Asn Gln Ala Glu Ala Ser Lys
        35                  40                  45

Glu Val Ala Glu Ser Asn Ser Cys Lys Phe Pro Ala Gly Ile Lys Ile
    50                  55                  60

Ile Asn His Pro Thr Met Pro Asn Thr Gln Val Val Ala Ile Pro Asn
65                  70                  75                  80

Asn Ala Asn Ile His Ser Ile Ile Thr Ala Leu Thr Ala Lys Gly Lys
                85                  90                  95

Glu Ser Gly Ser Ser Gly Pro Asn Lys Phe Ile Leu Ile Ser Cys Gly
            100                 105                 110

Gly Ala Pro Thr Gln Pro Pro Gly Leu Arg Pro Gln Thr Gln Thr Ser
        115                 120                 125

Tyr Asp Ala Lys Arg Thr Glu Val Thr Leu Glu Thr Leu Gly Pro Lys
    130                 135                 140

Pro Ala Ala Arg Asp Val Asn Leu Pro Arg Pro Pro Gly Ala Leu Cys
145                 150                 155                 160

Glu Gln Lys Arg Glu Thr Cys Ala Asp Gly Glu Ala Ala Gly Cys Thr
                165                 170                 175

Ile Asn Asn Ser Leu Ser Asn Ile Gln Trp Leu Arg Lys Met Ser Ser
            180                 185                 190

Asp Gly Leu Gly Ser Arg Ser Ile Lys Gln Glu Met Glu Glu Lys Glu
        195                 200                 205

Asn Cys His Leu Glu Gln Arg Gln Val Lys Val Glu Glu Pro Ser Arg
    210                 215                 220

Pro Ser Ala Ser Trp Gln Asn Ser Val Ser Glu Arg Pro Pro Tyr Ser
225                 230                 235                 240
```

```
Tyr Met Ala Met Ile Gln Phe Ala Ile Asn Ser Thr Glu Arg Lys Arg
                245                 250                 255

Met Thr Leu Lys Asp Ile Tyr Thr Trp Ile Glu Asp His Phe Pro Tyr
            260                 265                 270

Phe Lys His Ile Ala Lys Pro Gly Trp Lys Asn Ser Ile Arg His Asn
        275                 280                 285

Leu Ser Leu His Asp Met Phe Val Arg Glu Thr Ser Ala Asn Gly Lys
    290                 295                 300

Val Ser Phe Trp Thr Ile His Pro Ser Ala Asn Arg Tyr Leu Thr Leu
305                 310                 315                 320

Asp Gln Val Phe Lys Gln Gln Lys Arg Pro Asn Pro Glu Leu Arg Arg
                325                 330                 335

Asn Met Thr Ile Lys Thr Glu Leu Pro Leu Gly Ala Arg Arg Lys Met
            340                 345                 350

Lys Pro Leu Leu Pro Arg Val Ser Ser Tyr Leu Val Pro Ile Gln Phe
        355                 360                 365

Pro Val Asn Gln Ser Leu Val Leu Gln Pro Ser Val Lys Val Pro Leu
    370                 375                 380

Pro Leu Ala Ala Ser Leu Met Ser Ser Glu Leu Ala Arg His Ser Lys
385                 390                 395                 400

Arg Val Arg Ile Ala Pro Lys Val Leu Leu Ala Glu Glu Gly Ile Ala
                405                 410                 415

Pro Leu Ser Ser Ala Gly Pro Gly Lys Glu Glu Lys Leu Leu Phe Gly
            420                 425                 430

Glu Gly Phe Ser Pro Leu Leu Pro Val Gln Thr Ile Lys Glu Glu Glu
        435                 440                 445

Ile Gln Pro Gly Glu Glu Met Pro His Leu Ala Arg Pro Ile Lys Val
    450                 455                 460

Glu Ser Pro Pro Leu Glu Glu Trp Pro Ser Pro Ala Pro Ser Phe Lys
465                 470                 475                 480

Glu Glu Ser Ser His Ser Trp Glu Asp Ser Ser Gln Ser Pro Thr Pro
                485                 490                 495

Arg Pro Lys Lys Ser Tyr Ser Gly Leu Arg Ser Pro Thr Arg Cys Val
            500                 505                 510

Ser Glu Met Leu Val Ile Gln His Arg Glu Arg Arg Glu Arg Ser Arg
        515                 520                 525

Ser Arg Arg Lys Gln His Leu Leu Pro Pro Cys Val Asp Glu Pro Glu
    530                 535                 540

Leu Leu Phe Ser Glu Gly Pro Ser Thr Ser Arg Trp Ala Ala Glu Leu
545                 550                 555                 560

Pro Phe Pro Ala Asp Ser Ser Asp Pro Ala Ser Gln Leu Ser Tyr Ser
                565                 570                 575

Gln Glu Val Gly Gly Pro Phe Lys Thr Pro Ile Lys Glu Thr Leu Pro
            580                 585                 590

Ile Ser Ser Thr Pro Ser Lys Ser Val Leu Pro Arg Thr Pro Glu Ser
        595                 600                 605

Trp Arg Leu Thr Pro Pro Ala Lys Val Gly Gly Leu Asp Phe Ser Pro
    610                 615                 620

Val Gln Thr Ser Gln Gly Ala Ser Asp Pro Leu Pro Asp Pro Leu Gly
625                 630                 635                 640

Leu Met Asp Leu Ser Thr Thr Pro Leu Gln Ser Ala Pro Pro Leu Glu
                645                 650                 655
```

```
Ser Pro Gln Arg Leu Leu Ser Ser Glu Pro Leu Asp Leu Ile Ser Val
            660                 665                 670

Pro Phe Gly Asn Ser Ser Pro Ser Asp Ile Asp Val Pro Lys Pro Gly
        675                 680                 685

Ser Pro Glu Pro Gln Val Ser Gly Leu Ala Ala Asn Arg Ser Leu Thr
    690                 695                 700

Glu Gly Leu Val Leu Asp Thr Met Asn Asp Ser Leu Ser Lys Ile Leu
705                 710                 715                 720

Leu Asp Ile Ser Phe Pro Gly Leu Asp Glu Asp Pro Leu Gly Pro Asp
                725                 730                 735

Asn Ile Asn Trp Ser Gln Phe Ile Pro Glu Leu Gln
            740                 745


<210> SEQ ID NO 68
<211> LENGTH: 3506
<212> TYPE: DNA
<213> ORGANISM: Homo sapiens
<220> FEATURE:
<221> NAME/KEY: CDS
<222> LOCATION: (284)..(2530)

<400> SEQUENCE: 68

tttcaaacag cggaacaaac tgaaagctcc ggtgccagac cccacccccg gccccggccc      60

gggacccccct cccctcccgg gatcccccgg ggttcccacc ccgcccgcac cgccggggac    120

ccggccggtc cggcgcgagc ccccgtccgg ggccctggct cggcccccag gttggaggag    180

cccggagccc gccttcggag ctacggccta acggcggcgg cgactgcagt ctggagggtc    240

cacacttgtg attctcaatg gagagtgaaa acgcagattc ata atg aaa act agc      295
                                                Met Lys Thr Ser
                                                1

ccc cgt cgg cca ctg att ctc aaa aga cgg agg ctg ccc ctt cct gtt      343
Pro Arg Arg Pro Leu Ile Leu Lys Arg Arg Arg Leu Pro Leu Pro Val
5                   10                  15                  20

caa aat gcc cca agt gaa aca tca gag gag gaa cct aag aga tcc cct      391
Gln Asn Ala Pro Ser Glu Thr Ser Glu Glu Glu Pro Lys Arg Ser Pro
                25                  30                  35

gcc caa cag gag tct aat caa gca gag gcc tcc aag gaa gtg gca gag      439
Ala Gln Gln Glu Ser Asn Gln Ala Glu Ala Ser Lys Glu Val Ala Glu
            40                  45                  50

tcc aac tct tgc aag ttt cca gct ggg atc aag att att aac cac ccc      487
Ser Asn Ser Cys Lys Phe Pro Ala Gly Ile Lys Ile Ile Asn His Pro
        55                  60                  65

acc atg ccc aac acg caa gta gtg gcc atc ccc aac aat gct aat att      535
Thr Met Pro Asn Thr Gln Val Val Ala Ile Pro Asn Asn Ala Asn Ile
    70                  75                  80

cac agc atc atc aca gca ctg act gcc aag gga aaa gag agt ggc agt      583
His Ser Ile Ile Thr Ala Leu Thr Ala Lys Gly Lys Glu Ser Gly Ser
85                  90                  95                  100

agt ggg ccc aac aaa ttc atc ctc atc agc tgt ggg gga gcc cca act      631
Ser Gly Pro Asn Lys Phe Ile Leu Ile Ser Cys Gly Gly Ala Pro Thr
                105                 110                 115

cag cct cca gga ctc cgg cct caa acc caa acc agc tat gat gcc aaa      679
Gln Pro Pro Gly Leu Arg Pro Gln Thr Gln Thr Ser Tyr Asp Ala Lys
            120                 125                 130

agg aca gaa gtg acc ctg gag acc ttg gga cca aaa cct gca gct agg      727
Arg Thr Glu Val Thr Leu Glu Thr Leu Gly Pro Lys Pro Ala Ala Arg
        135                 140                 145

gat gtg aat ctt cct aga cca cct gga gcc ctt tgc gag cag aaa cgg      775
Asp Val Asn Leu Pro Arg Pro Pro Gly Ala Leu Cys Glu Gln Lys Arg
```

```
    150                 155                 160

gag acc tgt gat ggt gag gca gca ggc tgc act atc aac aat agc cta       823
Glu Thr Cys Asp Gly Glu Ala Ala Gly Cys Thr Ile Asn Asn Ser Leu
165                 170                 175                 180

tcc aac atc cag tgg ctt cga aag atg agt tct gat gga ctg ggc tcc       871
Ser Asn Ile Gln Trp Leu Arg Lys Met Ser Ser Asp Gly Leu Gly Ser
                185                 190                 195

cgc agc atc aag caa gag atg gag gaa aag gag aat tgt cac ctg gag       919
Arg Ser Ile Lys Gln Glu Met Glu Glu Lys Glu Asn Cys His Leu Glu
            200                 205                 210

cag cga cag gtt aag gtt gag gag cct tcg aga cca tca gcg tcc tgg       967
Gln Arg Gln Val Lys Val Glu Glu Pro Ser Arg Pro Ser Ala Ser Trp
        215                 220                 225

cag aac tct gtg tct gag cgg cca ccc tac tct tac atg gcc atg ata      1015
Gln Asn Ser Val Ser Glu Arg Pro Pro Tyr Ser Tyr Met Ala Met Ile
    230                 235                 240

caa ttc gcc atc aac agc act gag agg aag cgc atg act ttg aaa gac      1063
Gln Phe Ala Ile Asn Ser Thr Glu Arg Lys Arg Met Thr Leu Lys Asp
245                 250                 255                 260

atc tat acg tgg att gag gac cac ttt ccc tac ttt aag cac att gcc      1111
Ile Tyr Thr Trp Ile Glu Asp His Phe Pro Tyr Phe Lys His Ile Ala
                265                 270                 275

aag cca ggc tgg aag aac tcc atc cgc cac aac ctt tcc ctg cac gac      1159
Lys Pro Gly Trp Lys Asn Ser Ile Arg His Asn Leu Ser Leu His Asp
            280                 285                 290

atg ttt gtc cgg gag acg tct gcc aat ggc aag gtc tcc ttc tgg acc      1207
Met Phe Val Arg Glu Thr Ser Ala Asn Gly Lys Val Ser Phe Trp Thr
        295                 300                 305

att cac ccc agt gcc aac cgc tac ttg aca ttg gac cag gtg ttt aag      1255
Ile His Pro Ser Ala Asn Arg Tyr Leu Thr Leu Asp Gln Val Phe Lys
    310                 315                 320

cag cag cag aaa cga ccg aat cca gag ctc cgc cgg aac atg acc atc      1303
Gln Gln Gln Lys Arg Pro Asn Pro Glu Leu Arg Arg Asn Met Thr Ile
325                 330                 335                 340

aaa acc gaa ctc ccc ctg ggc gca cgg cgg aag atg aag cca ctg cta      1351
Lys Thr Glu Leu Pro Leu Gly Ala Arg Arg Lys Met Lys Pro Leu Leu
                345                 350                 355

cca cgg gtc agc tca tac ctg gta cct atc cag ttc ccg gtg aac cag      1399
Pro Arg Val Ser Ser Tyr Leu Val Pro Ile Gln Phe Pro Val Asn Gln
            360                 365                 370

tca ctg gtg ttg cag ccc tcg gtg aag gtg cca ttg ccc ctg gcg gct      1447
Ser Leu Val Leu Gln Pro Ser Val Lys Val Pro Leu Pro Leu Ala Ala
        375                 380                 385

tcc ctc atg agc tca gag ctt gcc cgc cat agc aag cga gtc cgc att      1495
Ser Leu Met Ser Ser Glu Leu Ala Arg His Ser Lys Arg Val Arg Ile
    390                 395                 400

gcc ccc aag gtg ctg cta gct gag gag ggg ata gct cct ctt tct tct      1543
Ala Pro Lys Val Leu Leu Ala Glu Glu Gly Ile Ala Pro Leu Ser Ser
405                 410                 415                 420

gca gga cca ggg aaa gag gag aaa ctc ctg ttt gga gaa ggg ttt tct      1591
Ala Gly Pro Gly Lys Glu Glu Lys Leu Leu Phe Gly Glu Gly Phe Ser
                425                 430                 435

cct ttg ctt cca gtt cag act atc aag gag gaa gaa atc cag cct ggg      1639
Pro Leu Leu Pro Val Gln Thr Ile Lys Glu Glu Glu Ile Gln Pro Gly
            440                 445                 450

gag gaa atg cca cac tta gcg aga ccc atc aaa gtg gag agc cct ccc      1687
Glu Glu Met Pro His Leu Ala Arg Pro Ile Lys Val Glu Ser Pro Pro
        455                 460                 465

ttg gaa gag tgg ccc tcc ccg gcc cca tct ttc aaa gag gaa tca tct      1735
```

```
Leu Glu Glu Trp Pro Ser Pro Ala Pro Ser Phe Lys Glu Glu Ser Ser
    470                 475                 480

cac tcc tgg gag gat tcg tcc caa tct ccc acc cca aga ccc aag aag      1783
His Ser Trp Glu Asp Ser Ser Gln Ser Pro Thr Pro Arg Pro Lys Lys
485                 490                 495                 500

tcc tac agt ggg ctt agg tcc cca acc cgg tgt gtc tcg gaa atg ctt      1831
Ser Tyr Ser Gly Leu Arg Ser Pro Thr Arg Cys Val Ser Glu Met Leu
                505                 510                 515

gtg att caa cac agg gag agg agg gag agg agc cgg tct cgg agg aaa      1879
Val Ile Gln His Arg Glu Arg Arg Glu Arg Ser Arg Ser Arg Arg Lys
            520                 525                 530

cag cat cta ctg cct ccc tgt gtg gat gag ccg gag ctg ctc ttc tca      1927
Gln His Leu Leu Pro Pro Cys Val Asp Glu Pro Glu Leu Leu Phe Ser
        535                 540                 545

gag ggg ccc agt act tcc cgc tgg gcc gca gag ctc ccg ttc cca gca      1975
Glu Gly Pro Ser Thr Ser Arg Trp Ala Ala Glu Leu Pro Phe Pro Ala
    550                 555                 560

gac tcc tct gac cct gcc tcc cag ctc agc tac tcc cag gaa gtg gga      2023
Asp Ser Ser Asp Pro Ala Ser Gln Leu Ser Tyr Ser Gln Glu Val Gly
565                 570                 575                 580

gga cct ttt aag aca ccc att aag gaa acg ctg ccc atc tcc tcc acc      2071
Gly Pro Phe Lys Thr Pro Ile Lys Glu Thr Leu Pro Ile Ser Ser Thr
                585                 590                 595

ccg agc aaa tct gtc ctc ccc aga acc cct gaa tcc tgg agg ctc acg      2119
Pro Ser Lys Ser Val Leu Pro Arg Thr Pro Glu Ser Trp Arg Leu Thr
            600                 605                 610

ccc cca gcc aaa gta ggg gga ctg gat ttc agc cca gta caa acc tcc      2167
Pro Pro Ala Lys Val Gly Gly Leu Asp Phe Ser Pro Val Gln Thr Ser
        615                 620                 625

cag ggt gcc tct gac ccc ttg cct gac ccc ctg ggg ctg atg gat ctc      2215
Gln Gly Ala Ser Asp Pro Leu Pro Asp Pro Leu Gly Leu Met Asp Leu
    630                 635                 640

agc acc act ccc ttg caa agt gct ccc ccc ctt gaa tca ccg caa agg      2263
Ser Thr Thr Pro Leu Gln Ser Ala Pro Pro Leu Glu Ser Pro Gln Arg
645                 650                 655                 660

ctc ctc agt tca gaa ccc tta gac ctc atc tcc gtc ccc ttt ggc aac      2311
Leu Leu Ser Ser Glu Pro Leu Asp Leu Ile Ser Val Pro Phe Gly Asn
                665                 670                 675

tct tct ccc tca gat ata gac gtc ccc aag cca ggc tcc ccg gag cca      2359
Ser Ser Pro Ser Asp Ile Asp Val Pro Lys Pro Gly Ser Pro Glu Pro
            680                 685                 690

cag gtt tct ggc ctt gca gcc aat cgt tct ctg aca gaa ggc ctg gtc      2407
Gln Val Ser Gly Leu Ala Ala Asn Arg Ser Leu Thr Glu Gly Leu Val
        695                 700                 705

ctg gac aca atg aat gac agc ctc agc aag atc ctg ctg gac atc agc      2455
Leu Asp Thr Met Asn Asp Ser Leu Ser Lys Ile Leu Leu Asp Ile Ser
    710                 715                 720

ttt cct ggc ctg gac gag gac cca ctg ggc cct gac aac atc aac tgg      2503
Phe Pro Gly Leu Asp Glu Asp Pro Leu Gly Pro Asp Asn Ile Asn Trp
725                 730                 735                 740

tcc cag ttt att cct gag cta cag tag agccctgccc ttgcccctgt           2550
Ser Gln Phe Ile Pro Glu Leu Gln
                745

gctcaagctg tccaccatcc cgggcactcc aaggctcagt gcaccccaag cctctgagtg   2610

aggacagcag gcagggactg ttctgctcct catagctccc tgctgcctga ttatgcaaaa   2670

gtagcagtca caccctagcc actgctggga ccttgtgttc cccaagagta tctgattcct   2730

ctgctgtccc tgccaggagc tgaagggtgg gaacaacaaa ggcaatggtg aaaagagatt   2790
```

```
aggaaccccc cagcctgttt ccattctctg cccagcagtc tcttaccttc cctgatcttt   2850

gcagggtggt ccgtgtaaat agtataaatt ctccaaatta tcctctaatt ataaatgtaa   2910

gcttatttcc ttagatcatt atccagagac tgccagaagg tgggtaggat gacctggggt   2970

ttcaattgac ttctgttcct tgcttttagt tttgatagaa gggaagacct gcagtgcacg   3030

gtttcttcca ggctgaggta cctggatctt gggttcttca ctgcagggac ccagacaagt   3090

ggatctgctt gccagagtcc tttttgcccc tccctgccac ctccccgtgt ttccaagtca   3150

gctttcctgc aagaagaaat cctggttaaa aaagtctttt gtattgggtc aggagttgaa   3210

tttggggtgg gaggatggat gcaactgaag cagagtgtgg gtgcccagat gtgcgctatt   3270

agatgtttct ctgataatgt ccccaatcat accagggaga ctggcattga cgagaactca   3330

ggtggaggct tgagaaggcc gaaagggccc ctgacctgcc tggcttcctt agcttgcccc   3390

tcagctttgc aaagagccac cctaggcccc agctgaccgc atgggtgtga gccagcttga   3450

gaacactaac tactcaataa aagcgaaggt ggacatgaaa aaaaaaaaaa aaaaaa       3506
```

<210> SEQ ID NO 69
<211> LENGTH: 748
<212> TYPE: PRT
<213> ORGANISM: Homo sapiens

<400> SEQUENCE: 69

```
Met Lys Thr Ser Pro Arg Arg Pro Leu Ile Leu Lys Arg Arg Arg Leu
1               5                   10                  15

Pro Leu Pro Val Gln Asn Ala Pro Ser Glu Thr Ser Glu Glu Glu Pro
            20                  25                  30

Lys Arg Ser Pro Ala Gln Gln Glu Ser Asn Gln Ala Glu Ala Ser Lys
        35                  40                  45

Glu Val Ala Glu Ser Asn Ser Cys Lys Phe Pro Ala Gly Ile Lys Ile
    50                  55                  60

Ile Asn His Pro Thr Met Pro Asn Thr Gln Val Val Ala Ile Pro Asn
65                  70                  75                  80

Asn Ala Asn Ile His Ser Ile Ile Thr Ala Leu Thr Ala Lys Gly Lys
                85                  90                  95

Glu Ser Gly Ser Ser Gly Pro Asn Lys Phe Ile Leu Ile Ser Cys Gly
            100                 105                 110

Gly Ala Pro Thr Gln Pro Pro Gly Leu Arg Pro Gln Thr Gln Thr Ser
        115                 120                 125

Tyr Asp Ala Lys Arg Thr Glu Val Thr Leu Glu Thr Leu Gly Pro Lys
    130                 135                 140

Pro Ala Ala Arg Asp Val Asn Leu Pro Arg Pro Pro Gly Ala Leu Cys
145                 150                 155                 160

Glu Gln Lys Arg Glu Thr Cys Asp Gly Glu Ala Ala Gly Cys Thr Ile
                165                 170                 175

Asn Asn Ser Leu Ser Asn Ile Gln Trp Leu Arg Lys Met Ser Ser Asp
            180                 185                 190

Gly Leu Gly Ser Arg Ser Ile Lys Gln Glu Met Glu Glu Lys Glu Asn
        195                 200                 205

Cys His Leu Glu Gln Arg Gln Val Lys Val Glu Glu Pro Ser Arg Pro
    210                 215                 220

Ser Ala Ser Trp Gln Asn Ser Val Ser Glu Arg Pro Pro Tyr Ser Tyr
225                 230                 235                 240

Met Ala Met Ile Gln Phe Ala Ile Asn Ser Thr Glu Arg Lys Arg Met
                245                 250                 255
```

```
Thr Leu Lys Asp Ile Tyr Thr Trp Ile Glu Asp His Phe Pro Tyr Phe
            260                 265                 270

Lys His Ile Ala Lys Pro Gly Trp Lys Asn Ser Ile Arg His Asn Leu
        275                 280                 285

Ser Leu His Asp Met Phe Val Arg Glu Thr Ser Ala Asn Gly Lys Val
    290                 295                 300

Ser Phe Trp Thr Ile His Pro Ser Ala Asn Arg Tyr Leu Thr Leu Asp
305                 310                 315                 320

Gln Val Phe Lys Gln Gln Gln Lys Arg Pro Asn Pro Glu Leu Arg Arg
                325                 330                 335

Asn Met Thr Ile Lys Thr Glu Leu Pro Leu Gly Ala Arg Arg Lys Met
            340                 345                 350

Lys Pro Leu Leu Pro Arg Val Ser Ser Tyr Leu Val Pro Ile Gln Phe
        355                 360                 365

Pro Val Asn Gln Ser Leu Val Leu Gln Pro Ser Val Lys Val Pro Leu
    370                 375                 380

Pro Leu Ala Ala Ser Leu Met Ser Ser Glu Leu Ala Arg His Ser Lys
385                 390                 395                 400

Arg Val Arg Ile Ala Pro Lys Val Leu Leu Ala Glu Glu Gly Ile Ala
                405                 410                 415

Pro Leu Ser Ser Ala Gly Pro Gly Lys Glu Glu Lys Leu Leu Phe Gly
            420                 425                 430

Glu Gly Phe Ser Pro Leu Leu Pro Val Gln Thr Ile Lys Glu Glu Glu
        435                 440                 445

Ile Gln Pro Gly Glu Glu Met Pro His Leu Ala Arg Pro Ile Lys Val
    450                 455                 460

Glu Ser Pro Pro Leu Glu Glu Trp Pro Ser Pro Ala Pro Ser Phe Lys
465                 470                 475                 480

Glu Glu Ser Ser His Ser Trp Glu Asp Ser Ser Gln Ser Pro Thr Pro
                485                 490                 495

Arg Pro Lys Lys Ser Tyr Ser Gly Leu Arg Ser Pro Thr Arg Cys Val
            500                 505                 510

Ser Glu Met Leu Val Ile Gln His Arg Glu Arg Arg Glu Arg Ser Arg
        515                 520                 525

Ser Arg Arg Lys Gln His Leu Leu Pro Pro Cys Val Asp Glu Pro Glu
    530                 535                 540

Leu Leu Phe Ser Glu Gly Pro Ser Thr Ser Arg Trp Ala Ala Glu Leu
545                 550                 555                 560

Pro Phe Pro Ala Asp Ser Ser Asp Pro Ala Ser Gln Leu Ser Tyr Ser
                565                 570                 575

Gln Glu Val Gly Gly Pro Phe Lys Thr Pro Ile Lys Glu Thr Leu Pro
            580                 585                 590

Ile Ser Ser Thr Pro Ser Lys Ser Val Leu Pro Arg Thr Pro Glu Ser
        595                 600                 605

Trp Arg Leu Thr Pro Pro Ala Lys Val Gly Gly Leu Asp Phe Ser Pro
    610                 615                 620

Val Gln Thr Ser Gln Gly Ala Ser Asp Pro Leu Pro Asp Pro Leu Gly
625                 630                 635                 640

Leu Met Asp Leu Ser Thr Thr Pro Leu Gln Ser Ala Pro Pro Leu Glu
                645                 650                 655

Ser Pro Gln Arg Leu Leu Ser Ser Glu Pro Leu Asp Leu Ile Ser Val
            660                 665                 670
```

```
Pro Phe Gly Asn Ser Ser Pro Ser Asp Ile Asp Val Pro Lys Pro Gly
        675                 680                 685

Ser Pro Glu Pro Gln Val Ser Gly Leu Ala Ala Asn Arg Ser Leu Thr
    690                 695                 700

Glu Gly Leu Val Leu Asp Thr Met Asn Asp Ser Leu Ser Lys Ile Leu
705                 710                 715                 720

Leu Asp Ile Ser Phe Pro Gly Leu Asp Glu Asp Pro Leu Gly Pro Asp
                725                 730                 735

Asn Ile Asn Trp Ser Gln Phe Ile Pro Glu Leu Gln
            740                 745


<210> SEQ ID NO 70
<211> LENGTH: 3503
<212> TYPE: DNA
<213> ORGANISM: Homo sapiens
<220> FEATURE:
<221> NAME/KEY: CDS
<222> LOCATION: (284)..(2527)

<400> SEQUENCE: 70

tttcaaacag cggaacaaac tgaaagctcc ggtgccagac cccacccccg gccccggccc     60

gggacccccct cccctcccgg gatccccccgg ggttcccacc ccgcccgcac cgccggggac    120

ccggccggtc cggcgcgagc ccccgtccgg ggccctggct cggcccccag gttggaggag    180

cccggagccc gccttcggag ctacggccta acggcggcgg cgactgcagt ctggagggtc    240

cacacttgtg attctcaatg gagagtgaaa acgcagattc ata atg aaa act agc      295
                                            Met Lys Thr Ser
                                            1

ccc cgt cgg cca ctg att ctc aaa aga cgg agg ctg ccc ctt cct gtt      343
Pro Arg Arg Pro Leu Ile Leu Lys Arg Arg Arg Leu Pro Leu Pro Val
5                   10                  15                  20

caa aat gcc cca agt gaa aca tca gag gag gaa cct aag aga tcc cct      391
Gln Asn Ala Pro Ser Glu Thr Ser Glu Glu Glu Pro Lys Arg Ser Pro
                25                  30                  35

gcc caa cag gag tct aat caa gca gag gcc tcc aag gaa gtg gca gag      439
Ala Gln Gln Glu Ser Asn Gln Ala Glu Ala Ser Lys Glu Val Ala Glu
            40                  45                  50

tcc aac tct tgc aag ttt cca gct ggg atc aag att att aac cac ccc      487
Ser Asn Ser Cys Lys Phe Pro Ala Gly Ile Lys Ile Ile Asn His Pro
        55                  60                  65

acc atg ccc aac acg caa gta gtg gcc atc ccc aac aat gct aat att      535
Thr Met Pro Asn Thr Gln Val Val Ala Ile Pro Asn Asn Ala Asn Ile
    70                  75                  80

cac agc atc atc aca gca ctg act gcc aag gga aaa gag agt ggc agt      583
His Ser Ile Ile Thr Ala Leu Thr Ala Lys Gly Lys Glu Ser Gly Ser
85                  90                  95                  100

agt ggg ccc aac aaa ttc atc ctc atc agc tgt ggg gga gcc cca act      631
Ser Gly Pro Asn Lys Phe Ile Leu Ile Ser Cys Gly Gly Ala Pro Thr
                105                 110                 115

cag cct cca gga ctc cgg cct caa acc caa acc agc tat gat gcc aaa      679
Gln Pro Pro Gly Leu Arg Pro Gln Thr Gln Thr Ser Tyr Asp Ala Lys
            120                 125                 130

agg aca gaa gtg acc ctg gag acc ttg gga cca aaa cct gca gct agg      727
Arg Thr Glu Val Thr Leu Glu Thr Leu Gly Pro Lys Pro Ala Ala Arg
        135                 140                 145

gat gtg aat ctt cct aga cca cct gga gcc ctt tgc gag cag aaa cgg      775
Asp Val Asn Leu Pro Arg Pro Pro Gly Ala Leu Cys Glu Gln Lys Arg
    150                 155                 160

gag acc tgt gat ggt gag gca gca ggc tgc act atc aac aat agc cta      823
```

```
Glu Thr Cys Asp Gly Glu Ala Ala Gly Cys Thr Ile Asn Asn Ser Leu
165                 170                 175                 180

tcc aac atc cag tgg ctt cga aag atg agt tct gat gga ctg ggc tcc      871
Ser Asn Ile Gln Trp Leu Arg Lys Met Ser Ser Asp Gly Leu Gly Ser
                185                 190                 195

cgc agc atc aag caa gag atg gag gaa aag gag aat tgt cac ctg gag      919
Arg Ser Ile Lys Gln Glu Met Glu Glu Lys Glu Asn Cys His Leu Glu
            200                 205                 210

cag cga cag gtt aag gtt gag gag cct tcg aga cca tca gcg tcc tgg      967
Gln Arg Gln Val Lys Val Glu Glu Pro Ser Arg Pro Ser Ala Ser Trp
        215                 220                 225

cag aac tct gtg tct gag cgg cca ccc tac tct tac atg gcc atg ata     1015
Gln Asn Ser Val Ser Glu Arg Pro Pro Tyr Ser Tyr Met Ala Met Ile
    230                 235                 240

caa ttc gcc atc aac agc act gag agg aag cgc atg act ttg aaa gac     1063
Gln Phe Ala Ile Asn Ser Thr Glu Arg Lys Arg Met Thr Leu Lys Asp
245                 250                 255                 260

atc tat acg tgg att gag gac cac ttt ccc tac ttt aag cac att gcc     1111
Ile Tyr Thr Trp Ile Glu Asp His Phe Pro Tyr Phe Lys His Ile Ala
                265                 270                 275

aag cca ggc tgg aag aac tcc atc cgc cac aac ctt tcc ctg cac gac     1159
Lys Pro Gly Trp Lys Asn Ser Ile Arg His Asn Leu Ser Leu His Asp
            280                 285                 290

atg ttt gtc cgg gag acg tct gcc aat ggc aag gtc tcc ttc tgg acc     1207
Met Phe Val Arg Glu Thr Ser Ala Asn Gly Lys Val Ser Phe Trp Thr
        295                 300                 305

att cac ccc agt gcc aac cgc tac ttg aca ttg gac cag gtg ttt aag     1255
Ile His Pro Ser Ala Asn Arg Tyr Leu Thr Leu Asp Gln Val Phe Lys
    310                 315                 320

cag cag aaa cga ccg aat cca gag ctc cgc cgg aac atg acc atc aaa     1303
Gln Gln Lys Arg Pro Asn Pro Glu Leu Arg Arg Asn Met Thr Ile Lys
325                 330                 335                 340

acc gaa ctc ccc ctg ggc gca cgg cgg aag atg aag cca ctg cta cca     1351
Thr Glu Leu Pro Leu Gly Ala Arg Arg Lys Met Lys Pro Leu Leu Pro
                345                 350                 355

cgg gtc agc tca tac ctg gta cct atc cag ttc ccg gtg aac cag tca     1399
Arg Val Ser Ser Tyr Leu Val Pro Ile Gln Phe Pro Val Asn Gln Ser
            360                 365                 370

ctg gtg ttg cag ccc tcg gtg aag gtg cca ttg ccc ctg gcg gct tcc     1447
Leu Val Leu Gln Pro Ser Val Lys Val Pro Leu Pro Leu Ala Ala Ser
        375                 380                 385

ctc atg agc tca gag ctt gcc cgc cat agc aag cga gtc cgc att gcc     1495
Leu Met Ser Ser Glu Leu Ala Arg His Ser Lys Arg Val Arg Ile Ala
    390                 395                 400

ccc aag gtg ctg cta gct gag gag ggg ata gct cct ctt tct tct gca     1543
Pro Lys Val Leu Leu Ala Glu Glu Gly Ile Ala Pro Leu Ser Ser Ala
405                 410                 415                 420

gga cca ggg aaa gag gag aaa ctc ctg ttt gga gaa ggg ttt tct cct     1591
Gly Pro Gly Lys Glu Glu Lys Leu Leu Phe Gly Glu Gly Phe Ser Pro
                425                 430                 435

ttg ctt cca gtt cag act atc aag gag gaa gaa atc cag cct ggg gag     1639
Leu Leu Pro Val Gln Thr Ile Lys Glu Glu Glu Ile Gln Pro Gly Glu
            440                 445                 450

gaa atg cca cac tta gcg aga ccc atc aaa gtg gag agc cct ccc ttg     1687
Glu Met Pro His Leu Ala Arg Pro Ile Lys Val Glu Ser Pro Pro Leu
        455                 460                 465

gaa gag tgg ccc tcc ccg gcc cca tct ttc aaa gag gaa tca tct cac     1735
Glu Glu Trp Pro Ser Pro Ala Pro Ser Phe Lys Glu Glu Ser Ser His
    470                 475                 480
```

```
tcc tgg gag gat tcg tcc caa tct ccc acc cca aga ccc aag aag tcc     1783
Ser Trp Glu Asp Ser Ser Gln Ser Pro Thr Pro Arg Pro Lys Lys Ser
485                 490                 495                 500

tac agt ggg ctt agg tcc cca acc cgg tgt gtc tcg gaa atg ctt gtg     1831
Tyr Ser Gly Leu Arg Ser Pro Thr Arg Cys Val Ser Glu Met Leu Val
                505                 510                 515

att caa cac agg gag agg agg gag agg agc cgg tct cgg agg aaa cag     1879
Ile Gln His Arg Glu Arg Arg Glu Arg Ser Arg Ser Arg Arg Lys Gln
            520                 525                 530

cat cta ctg cct ccc tgt gtg gat gag ccg gag ctg ctc ttc tca gag     1927
His Leu Leu Pro Pro Cys Val Asp Glu Pro Glu Leu Leu Phe Ser Glu
        535                 540                 545

ggg ccc agt act tcc cgc tgg gcc gca gag ctc ccg ttc cca gca gac     1975
Gly Pro Ser Thr Ser Arg Trp Ala Ala Glu Leu Pro Phe Pro Ala Asp
    550                 555                 560

tcc tct gac cct gcc tcc cag ctc agc tac tcc cag gaa gtg gga gga     2023
Ser Ser Asp Pro Ala Ser Gln Leu Ser Tyr Ser Gln Glu Val Gly Gly
565                 570                 575                 580

cct ttt aag aca ccc att aag gaa acg ctg ccc atc tcc tcc acc ccg     2071
Pro Phe Lys Thr Pro Ile Lys Glu Thr Leu Pro Ile Ser Ser Thr Pro
                585                 590                 595

agc aaa tct gtc ctc ccc aga acc cct gaa tcc tgg agg ctc acg ccc     2119
Ser Lys Ser Val Leu Pro Arg Thr Pro Glu Ser Trp Arg Leu Thr Pro
            600                 605                 610

cca gcc aaa gta ggg gga ctg gat ttc agc cca gta caa acc tcc cag     2167
Pro Ala Lys Val Gly Gly Leu Asp Phe Ser Pro Val Gln Thr Ser Gln
        615                 620                 625

ggt gcc tct gac ccc ttg cct gac ccc ctg ggg ctg atg gat ctc agc     2215
Gly Ala Ser Asp Pro Leu Pro Asp Pro Leu Gly Leu Met Asp Leu Ser
    630                 635                 640

acc act ccc ttg caa agt gct ccc ccc ctt gaa tca ccg caa agg ctc     2263
Thr Thr Pro Leu Gln Ser Ala Pro Pro Leu Glu Ser Pro Gln Arg Leu
645                 650                 655                 660

ctc agt tca gaa ccc tta gac ctc atc tcc gtc ccc ttt ggc aac tct     2311
Leu Ser Ser Glu Pro Leu Asp Leu Ile Ser Val Pro Phe Gly Asn Ser
                665                 670                 675

tct ccc tca gat ata gac gtc ccc aag cca ggc tcc ccg gag cca cag     2359
Ser Pro Ser Asp Ile Asp Val Pro Lys Pro Gly Ser Pro Glu Pro Gln
            680                 685                 690

gtt tct ggc ctt gca gcc aat cgt tct ctg aca gaa ggc ctg gtc ctg     2407
Val Ser Gly Leu Ala Ala Asn Arg Ser Leu Thr Glu Gly Leu Val Leu
        695                 700                 705

gac aca atg aat gac agc ctc agc aag atc ctg ctg gac atc agc ttt     2455
Asp Thr Met Asn Asp Ser Leu Ser Lys Ile Leu Leu Asp Ile Ser Phe
    710                 715                 720

cct ggc ctg gac gag gac cca ctg ggc cct gac aac atc aac tgg tcc     2503
Pro Gly Leu Asp Glu Asp Pro Leu Gly Pro Asp Asn Ile Asn Trp Ser
725                 730                 735                 740

cag ttt att cct gag cta cag tag agccctgccc ttgcccctgt gctcaagctg    2557
Gln Phe Ile Pro Glu Leu Gln
                745

tccaccatcc cgggcactcc aaggctcagt gcaccccaag cctctgagtg aggacagcag   2617

gcagggactg ttctgctcct catagctccc tgctgcctga ttatgcaaaa gtagcagtca   2677

caccctagcc actgctggga ccttgtgttc cccaagagta tctgattcct ctgctgtccc   2737

tgccaggagc tgaagggtgg gaacaacaaa ggcaatggtg aaaagagatt aggaaccccc   2797

cagcctgttt ccattctctg cccagcagtc tcttaccttc cctgatcttt gcagggtggt   2857

ccgtgtaaat agtataaatt ctccaaatta tcctctaatt ataaatgtaa gcttatttcc   2917
```

ttagatcatt atccagagac tgccagaagg tgggtaggat gacctggggt ttcaattgac 2977 ttctgttcct tgcttttagt tttgatagaa gggaagacct gcagtgcacg gtttcttcca 3037 ggctgaggta cctggatctt gggttcttca ctgcagggac ccagacaagt ggatctgctt 3097 gccagagtcc tttttgcccc tccctgccac ctccccgtgt ttccaagtca gctttcctgc 3157 aagaagaaat cctggttaaa aaagtctttt gtattgggtc aggagttgaa tttggggtgg 3217 gaggatggat gcaactgaag cagagtgtgg gtgcccagat gtgcgctatt agatgtttct 3277 ctgataatgt ccccaatcat accagggaga ctggcattga cgagaactca ggtggaggct 3337 tgagaaggcc gaaagggccc ctgacctgcc tggcttcctt agcttgcccc tcagctttgc 3397 aaagagccac cctaggcccc agctgaccgc atgggtgtga gccagcttga gaacactaac 3457 tactcaataa aagcgaaggt ggacatgaaa aaaaaaaaaa aaaaaa 3503

<210> SEQ ID NO 71
<211> LENGTH: 747
<212> TYPE: PRT
<213> ORGANISM: Homo sapiens

<400> SEQUENCE: 71

Met Lys Thr Ser Pro Arg Arg Pro Leu Ile Leu Lys Arg Arg Arg Leu
1 5 10 15

Pro Leu Pro Val Gln Asn Ala Pro Ser Glu Thr Ser Glu Glu Glu Pro
20 25 30

Lys Arg Ser Pro Ala Gln Gln Glu Ser Asn Gln Ala Glu Ala Ser Lys
35 40 45

Glu Val Ala Glu Ser Asn Ser Cys Lys Phe Pro Ala Gly Ile Lys Ile
50 55 60

Ile Asn His Pro Thr Met Pro Asn Thr Gln Val Val Ala Ile Pro Asn
65 70 75 80

Asn Ala Asn Ile His Ser Ile Ile Thr Ala Leu Thr Ala Lys Gly Lys
85 90 95

Glu Ser Gly Ser Ser Gly Pro Asn Lys Phe Ile Leu Ile Ser Cys Gly
100 105 110

Gly Ala Pro Thr Gln Pro Pro Gly Leu Arg Pro Gln Thr Gln Thr Ser
115 120 125

Tyr Asp Ala Lys Arg Thr Glu Val Thr Leu Glu Thr Leu Gly Pro Lys
130 135 140

Pro Ala Ala Arg Asp Val Asn Leu Pro Arg Pro Pro Gly Ala Leu Cys
145 150 155 160

Glu Gln Lys Arg Glu Thr Cys Asp Gly Glu Ala Ala Gly Cys Thr Ile
165 170 175

Asn Asn Ser Leu Ser Asn Ile Gln Trp Leu Arg Lys Met Ser Ser Asp
180 185 190

Gly Leu Gly Ser Arg Ser Ile Lys Gln Glu Met Glu Glu Lys Glu Asn
195 200 205

Cys His Leu Glu Gln Arg Gln Val Lys Val Glu Glu Pro Ser Arg Pro
210 215 220

Ser Ala Ser Trp Gln Asn Ser Val Ser Glu Arg Pro Pro Tyr Ser Tyr
225 230 235 240

Met Ala Met Ile Gln Phe Ala Ile Asn Ser Thr Glu Arg Lys Arg Met
245 250 255

Thr Leu Lys Asp Ile Tyr Thr Trp Ile Glu Asp His Phe Pro Tyr Phe
260 265 270

Lys His Ile Ala Lys Pro Gly Trp Lys Asn Ser Ile Arg His Asn Leu
        275                 280                 285

Ser Leu His Asp Met Phe Val Arg Glu Thr Ser Ala Asn Gly Lys Val
    290                 295                 300

Ser Phe Trp Thr Ile His Pro Ser Ala Asn Arg Tyr Leu Thr Leu Asp
305                 310                 315                 320

Gln Val Phe Lys Gln Gln Lys Arg Pro Asn Pro Glu Leu Arg Arg Asn
                325                 330                 335

Met Thr Ile Lys Thr Glu Leu Pro Leu Gly Ala Arg Arg Lys Met Lys
            340                 345                 350

Pro Leu Leu Pro Arg Val Ser Ser Tyr Leu Val Pro Ile Gln Phe Pro
        355                 360                 365

Val Asn Gln Ser Leu Val Leu Gln Pro Ser Val Lys Val Pro Leu Pro
    370                 375                 380

Leu Ala Ala Ser Leu Met Ser Ser Glu Leu Ala Arg His Ser Lys Arg
385                 390                 395                 400

Val Arg Ile Ala Pro Lys Val Leu Leu Ala Glu Glu Gly Ile Ala Pro
                405                 410                 415

Leu Ser Ser Ala Gly Pro Gly Lys Glu Glu Lys Leu Leu Phe Gly Glu
            420                 425                 430

Gly Phe Ser Pro Leu Leu Pro Val Gln Thr Ile Lys Glu Glu Glu Ile
        435                 440                 445

Gln Pro Gly Glu Glu Met Pro His Leu Ala Arg Pro Ile Lys Val Glu
    450                 455                 460

Ser Pro Pro Leu Glu Glu Trp Pro Ser Pro Ala Pro Ser Phe Lys Glu
465                 470                 475                 480

Glu Ser Ser His Ser Trp Glu Asp Ser Ser Gln Ser Pro Thr Pro Arg
                485                 490                 495

Pro Lys Lys Ser Tyr Ser Gly Leu Arg Ser Pro Thr Arg Cys Val Ser
            500                 505                 510

Glu Met Leu Val Ile Gln His Arg Glu Arg Arg Glu Arg Ser Arg Ser
        515                 520                 525

Arg Arg Lys Gln His Leu Leu Pro Pro Cys Val Asp Glu Pro Glu Leu
    530                 535                 540

Leu Phe Ser Glu Gly Pro Ser Thr Ser Arg Trp Ala Ala Glu Leu Pro
545                 550                 555                 560

Phe Pro Ala Asp Ser Ser Asp Pro Ala Ser Gln Leu Ser Tyr Ser Gln
                565                 570                 575

Glu Val Gly Gly Pro Phe Lys Thr Pro Ile Lys Glu Thr Leu Pro Ile
            580                 585                 590

Ser Ser Thr Pro Ser Lys Ser Val Leu Pro Arg Thr Pro Glu Ser Trp
        595                 600                 605

Arg Leu Thr Pro Pro Ala Lys Val Gly Gly Leu Asp Phe Ser Pro Val
    610                 615                 620

Gln Thr Ser Gln Gly Ala Ser Asp Pro Leu Pro Asp Pro Leu Gly Leu
625                 630                 635                 640

Met Asp Leu Ser Thr Thr Pro Leu Gln Ser Ala Pro Pro Leu Glu Ser
                645                 650                 655

Pro Gln Arg Leu Leu Ser Ser Glu Pro Leu Asp Leu Ile Ser Val Pro
            660                 665                 670

Phe Gly Asn Ser Ser Pro Ser Asp Ile Asp Val Pro Lys Pro Gly Ser
        675                 680                 685

```
Pro Glu Pro Gln Val Ser Gly Leu Ala Ala Asn Arg Ser Leu Thr Glu
    690                 695                 700

Gly Leu Val Leu Asp Thr Met Asn Asp Ser Leu Ser Lys Ile Leu Leu
705                 710                 715                 720

Asp Ile Ser Phe Pro Gly Leu Asp Glu Asp Pro Leu Gly Pro Asp Asn
                725                 730                 735

Ile Asn Trp Ser Gln Phe Ile Pro Glu Leu Gln
            740                 745


<210> SEQ ID NO 72
<211> LENGTH: 3551
<212> TYPE: DNA
<213> ORGANISM: Homo sapiens
<220> FEATURE:
<221> NAME/KEY: CDS
<222> LOCATION: (284)..(2575)

<400> SEQUENCE: 72

tttcaaacag cggaacaaac tgaaagctcc ggtgccagac cccacccccg gccccggccc      60

gggacccccct cccctcccgg gatcccccgg ggttcccacc ccgcccgcac cgccggggac    120

ccggccggtc cggcgcgagc ccccgtccgg ggccctggct cggcccccag gttggaggag    180

cccggagccc gccttcggag ctacggccta acggcggcgg cgactgcagt ctggagggtc    240

cacacttgtg attctcaatg gagagtgaaa acgcagattc ata atg aaa act agc      295
                                                Met Lys Thr Ser
                                                1

ccc cgt cgg cca ctg att ctc aaa aga cgg agg ctg ccc ctt cct gtt      343
Pro Arg Arg Pro Leu Ile Leu Lys Arg Arg Arg Leu Pro Leu Pro Val
5                   10                  15                  20

caa aat gcc cca agt gaa aca tca gag gag gaa cct aag aga tcc cct      391
Gln Asn Ala Pro Ser Glu Thr Ser Glu Glu Glu Pro Lys Arg Ser Pro
                25                  30                  35

gcc caa cag gag tct aat caa gca gag gcc tcc aag gaa gtg gca gag      439
Ala Gln Gln Glu Ser Asn Gln Ala Glu Ala Ser Lys Glu Val Ala Glu
            40                  45                  50

tcc aac tct tgc aag ttt cca gct ggg atc aag att att aac cac ccc      487
Ser Asn Ser Cys Lys Phe Pro Ala Gly Ile Lys Ile Ile Asn His Pro
        55                  60                  65

acc atg ccc aac acg caa gta gtg gcc atc ccc aac aat gct aat att      535
Thr Met Pro Asn Thr Gln Val Val Ala Ile Pro Asn Asn Ala Asn Ile
    70                  75                  80

cac agc atc atc aca gca ctg act gcc aag gga aaa gag agt ggc agt      583
His Ser Ile Ile Thr Ala Leu Thr Ala Lys Gly Lys Glu Ser Gly Ser
85                  90                  95                  100

agt ggg ccc aac aaa ttc atc ctc atc agc tgt ggg gga gcc cca act      631
Ser Gly Pro Asn Lys Phe Ile Leu Ile Ser Cys Gly Gly Ala Pro Thr
                105                 110                 115

cag cct cca gga ctc cgg cct caa acc caa acc agc tat gat gcc aaa      679
Gln Pro Pro Gly Leu Arg Pro Gln Thr Gln Thr Ser Tyr Asp Ala Lys
            120                 125                 130

agg aca gaa gtg acc ctg gag acc ttg gga cca aaa cct gca gct agg      727
Arg Thr Glu Val Thr Leu Glu Thr Leu Gly Pro Lys Pro Ala Ala Arg
        135                 140                 145

gat gtg aat ctt cct aga cca cct gga gcc ctt tgc gag cag aaa cgg      775
Asp Val Asn Leu Pro Arg Pro Pro Gly Ala Leu Cys Glu Gln Lys Arg
    150                 155                 160

gag acc tgt gca gat ggt gag gca gca ggc tgc act atc aac aat agc      823
Glu Thr Cys Ala Asp Gly Glu Ala Ala Gly Cys Thr Ile Asn Asn Ser
165                 170                 175                 180
```

```
cta tcc aac atc cag tgg ctt cga aag atg agt tct gat gga ctg ggc      871
Leu Ser Asn Ile Gln Trp Leu Arg Lys Met Ser Ser Asp Gly Leu Gly
                185                 190                 195

tcc cgc agc atc aag caa gag atg gag gaa aag gag aat tgt cac ctg      919
Ser Arg Ser Ile Lys Gln Glu Met Glu Glu Lys Glu Asn Cys His Leu
            200                 205                 210

gag cag cga cag gtt aag gtt gag gag cct tcg aga cca tca gcg tcc      967
Glu Gln Arg Gln Val Lys Val Glu Glu Pro Ser Arg Pro Ser Ala Ser
        215                 220                 225

tgg cag aac tct gtg tct gag cgg cca ccc tac tct tac atg gcc atg     1015
Trp Gln Asn Ser Val Ser Glu Arg Pro Pro Tyr Ser Tyr Met Ala Met
    230                 235                 240

ata caa ttc gcc atc aac agc act gag agg aag cgc atg act ttg aaa     1063
Ile Gln Phe Ala Ile Asn Ser Thr Glu Arg Lys Arg Met Thr Leu Lys
245                 250                 255                 260

gac atc tat acg tgg att gag gac cac ttt ccc tac ttt aag cac att     1111
Asp Ile Tyr Thr Trp Ile Glu Asp His Phe Pro Tyr Phe Lys His Ile
                265                 270                 275

gcc aag cca ggc tgg aag aac tcc atc cgc cac aac ctt tcc ctg cac     1159
Ala Lys Pro Gly Trp Lys Asn Ser Ile Arg His Asn Leu Ser Leu His
            280                 285                 290

gac atg ttt gtc cgg gag acg tct gcc aat ggc aag gtc tcc ttc tgg     1207
Asp Met Phe Val Arg Glu Thr Ser Ala Asn Gly Lys Val Ser Phe Trp
        295                 300                 305

acc att cac ccc agt gcc aac cgc tac ttg aca ttg gac cag gtg ttt     1255
Thr Ile His Pro Ser Ala Asn Arg Tyr Leu Thr Leu Asp Gln Val Phe
    310                 315                 320

aag cca ctg gac cca ggg tct cca caa ttg ccc gag cac ttg gaa tca     1303
Lys Pro Leu Asp Pro Gly Ser Pro Gln Leu Pro Glu His Leu Glu Ser
325                 330                 335                 340

cag cag aaa cga ccg aat cca gag ctc cgc cgg aac atg acc atc aaa     1351
Gln Gln Lys Arg Pro Asn Pro Glu Leu Arg Arg Asn Met Thr Ile Lys
                345                 350                 355

acc gaa ctc ccc ctg ggc gca cgg cgg aag atg aag cca ctg cta cca     1399
Thr Glu Leu Pro Leu Gly Ala Arg Arg Lys Met Lys Pro Leu Leu Pro
            360                 365                 370

cgg gtc agc tca tac ctg gta cct atc cag ttc ccg gtg aac cag tca     1447
Arg Val Ser Ser Tyr Leu Val Pro Ile Gln Phe Pro Val Asn Gln Ser
        375                 380                 385

ctg gtg ttg cag ccc tcg gtg aag gtg cca ttg ccc ctg gcg gct tcc     1495
Leu Val Leu Gln Pro Ser Val Lys Val Pro Leu Pro Leu Ala Ala Ser
    390                 395                 400

ctc atg agc tca gag ctt gcc cgc cat agc aag cga gtc cgc att gcc     1543
Leu Met Ser Ser Glu Leu Ala Arg His Ser Lys Arg Val Arg Ile Ala
405                 410                 415                 420

ccc aag gtg ctg cta gct gag gag ggg ata gct cct ctt tct tct gca     1591
Pro Lys Val Leu Leu Ala Glu Glu Gly Ile Ala Pro Leu Ser Ser Ala
                425                 430                 435

gga cca ggg aaa gag gag aaa ctc ctg ttt gga gaa ggg ttt tct cct     1639
Gly Pro Gly Lys Glu Glu Lys Leu Leu Phe Gly Glu Gly Phe Ser Pro
            440                 445                 450

ttg ctt cca gtt cag act atc aag gag gaa gaa atc cag cct ggg gag     1687
Leu Leu Pro Val Gln Thr Ile Lys Glu Glu Glu Ile Gln Pro Gly Glu
        455                 460                 465

gaa atg cca cac tta gcg aga ccc atc aaa gtg gag agc cct ccc ttg     1735
Glu Met Pro His Leu Ala Arg Pro Ile Lys Val Glu Ser Pro Pro Leu
    470                 475                 480

gaa gag tgg ccc tcc ccg gcc cca tct ttc aaa gag gaa tca tct cac     1783
Glu Glu Trp Pro Ser Pro Ala Pro Ser Phe Lys Glu Glu Ser Ser His
485                 490                 495                 500
```

```
tcc tgg gag gat tcg tcc caa tct ccc acc cca aga ccc aag aag tcc     1831
Ser Trp Glu Asp Ser Ser Gln Ser Pro Thr Pro Arg Pro Lys Lys Ser
                505                 510                 515

tac agt ggg ctt agg tcc cca acc cgg tgt gtc tcg gaa atg ctt gtg     1879
Tyr Ser Gly Leu Arg Ser Pro Thr Arg Cys Val Ser Glu Met Leu Val
            520                 525                 530

att caa cac agg gag agg agg gag agg agc cgg tct cgg agg aaa cag     1927
Ile Gln His Arg Glu Arg Arg Glu Arg Ser Arg Ser Arg Arg Lys Gln
        535                 540                 545

cat cta ctg cct ccc tgt gtg gat gag ccg gag ctg ctc ttc tca gag     1975
His Leu Leu Pro Pro Cys Val Asp Glu Pro Glu Leu Leu Phe Ser Glu
    550                 555                 560

ggg ccc agt act tcc cgc tgg gcc gca gag ctc ccg ttc cca gca gac     2023
Gly Pro Ser Thr Ser Arg Trp Ala Ala Glu Leu Pro Phe Pro Ala Asp
565                 570                 575                 580

tcc tct gac cct gcc tcc cag ctc agc tac tcc cag gaa gtg gga gga     2071
Ser Ser Asp Pro Ala Ser Gln Leu Ser Tyr Ser Gln Glu Val Gly Gly
                585                 590                 595

cct ttt aag aca ccc att aag gaa acg ctg ccc atc tcc tcc acc ccg     2119
Pro Phe Lys Thr Pro Ile Lys Glu Thr Leu Pro Ile Ser Ser Thr Pro
            600                 605                 610

agc aaa tct gtc ctc ccc aga acc cct gaa tcc tgg agg ctc acg ccc     2167
Ser Lys Ser Val Leu Pro Arg Thr Pro Glu Ser Trp Arg Leu Thr Pro
        615                 620                 625

cca gcc aaa gta ggg gga ctg gat ttc agc cca gta caa acc tcc cag     2215
Pro Ala Lys Val Gly Gly Leu Asp Phe Ser Pro Val Gln Thr Ser Gln
    630                 635                 640

ggt gcc tct gac ccc ttg cct gac ccc ctg ggg ctg atg gat ctc agc     2263
Gly Ala Ser Asp Pro Leu Pro Asp Pro Leu Gly Leu Met Asp Leu Ser
645                 650                 655                 660

acc act ccc ttg caa agt gct ccc ccc ctt gaa tca ccg caa agg ctc     2311
Thr Thr Pro Leu Gln Ser Ala Pro Pro Leu Glu Ser Pro Gln Arg Leu
                665                 670                 675

ctc agt tca gaa ccc tta gac ctc atc tcc gtc ccc ttt ggc aac tct     2359
Leu Ser Ser Glu Pro Leu Asp Leu Ile Ser Val Pro Phe Gly Asn Ser
            680                 685                 690

tct ccc tca gat ata gac gtc ccc aag cca ggc tcc ccg gag cca cag     2407
Ser Pro Ser Asp Ile Asp Val Pro Lys Pro Gly Ser Pro Glu Pro Gln
        695                 700                 705

gtt tct ggc ctt gca gcc aat cgt tct ctg aca gaa ggc ctg gtc ctg     2455
Val Ser Gly Leu Ala Ala Asn Arg Ser Leu Thr Glu Gly Leu Val Leu
    710                 715                 720

gac aca atg aat gac agc ctc agc aag atc ctg ctg gac atc agc ttt     2503
Asp Thr Met Asn Asp Ser Leu Ser Lys Ile Leu Leu Asp Ile Ser Phe
725                 730                 735                 740

cct ggc ctg gac gag gac cca ctg ggc cct gac aac atc aac tgg tcc     2551
Pro Gly Leu Asp Glu Asp Pro Leu Gly Pro Asp Asn Ile Asn Trp Ser
                745                 750                 755

cag ttt att cct gag cta cag tag agccctgccc ttgcccctgt gctcaagctg    2605
Gln Phe Ile Pro Glu Leu Gln
            760

tccaccatcc cgggcactcc aaggctcagt gcaccccaag cctctgagtg aggacagcag   2665

gcagggactg ttctgctcct catagctccc tgctgcctga ttatgcaaaa gtagcagtca   2725

caccctagcc actgctggga ccttgtgttc cccaagagta tctgattcct ctgctgtccc   2785

tgccaggagc tgaagggtgg gaacaacaaa ggcaatggtg aaaagagatt aggaaccccc   2845

cagcctgttt ccattctctg cccagcagtc tcttaccttc cctgatcttt gcagggtggt   2905
```

```
ccgtgtaaat agtataaatt ctccaaatta tcctctaatt ataaatgtaa gcttatttcc   2965

ttagatcatt atccagagac tgccagaagg tgggtaggat gacctggggt ttcaattgac   3025

ttctgttcct tgcttttagt tttgatagaa gggaagacct gcagtgcacg gtttcttcca   3085

ggctgaggta cctggatctt gggttcttca ctgcagggac ccagacaagt ggatctgctt   3145

gccagagtcc tttttgcccc tccctgccac ctccccgtgt ttccaagtca gctttcctgc   3205

aagaagaaat cctggttaaa aaagtctttt gtattgggtc aggagttgaa tttggggtgg   3265

gaggatggat gcaactgaag cagagtgtgg gtgcccagat gtgcgctatt agatgtttct   3325

ctgataatgt ccccaatcat accagggaga ctggcattga cgagaactca ggtggaggct   3385

tgagaaggcc gaaagggccc ctgacctgcc tggcttcctt agcttgcccc tcagctttgc   3445

aaagagccac cctaggcccc agctgaccgc atgggtgtga gccagcttga gaacactaac   3505

tactcaataa aagcgaaggt ggacatgaaa aaaaaaaaaa aaaaaa                  3551
```

```
<210> SEQ ID NO 73
<211> LENGTH: 763
<212> TYPE: PRT
<213> ORGANISM: Homo sapiens

<400> SEQUENCE: 73

Met Lys Thr Ser Pro Arg Arg Pro Leu Ile Leu Lys Arg Arg Arg Leu
1               5                   10                  15

Pro Leu Pro Val Gln Asn Ala Pro Ser Glu Thr Ser Glu Glu Glu Pro
            20                  25                  30

Lys Arg Ser Pro Ala Gln Gln Glu Ser Asn Gln Ala Glu Ala Ser Lys
        35                  40                  45

Glu Val Ala Glu Ser Asn Ser Cys Lys Phe Pro Ala Gly Ile Lys Ile
    50                  55                  60

Ile Asn His Pro Thr Met Pro Asn Thr Gln Val Val Ala Ile Pro Asn
65                  70                  75                  80

Asn Ala Asn Ile His Ser Ile Ile Thr Ala Leu Thr Ala Lys Gly Lys
                85                  90                  95

Glu Ser Gly Ser Ser Gly Pro Asn Lys Phe Ile Leu Ile Ser Cys Gly
            100                 105                 110

Gly Ala Pro Thr Gln Pro Pro Gly Leu Arg Pro Gln Thr Gln Thr Ser
        115                 120                 125

Tyr Asp Ala Lys Arg Thr Glu Val Thr Leu Glu Thr Leu Gly Pro Lys
    130                 135                 140

Pro Ala Ala Arg Asp Val Asn Leu Pro Arg Pro Pro Gly Ala Leu Cys
145                 150                 155                 160

Glu Gln Lys Arg Glu Thr Cys Ala Asp Gly Glu Ala Ala Gly Cys Thr
                165                 170                 175

Ile Asn Asn Ser Leu Ser Asn Ile Gln Trp Leu Arg Lys Met Ser Ser
            180                 185                 190

Asp Gly Leu Gly Ser Arg Ser Ile Lys Gln Glu Met Glu Glu Lys Glu
        195                 200                 205

Asn Cys His Leu Glu Gln Arg Gln Val Lys Val Glu Glu Pro Ser Arg
    210                 215                 220

Pro Ser Ala Ser Trp Gln Asn Ser Val Ser Glu Arg Pro Pro Tyr Ser
225                 230                 235                 240

Tyr Met Ala Met Ile Gln Phe Ala Ile Asn Ser Thr Glu Arg Lys Arg
                245                 250                 255

Met Thr Leu Lys Asp Ile Tyr Thr Trp Ile Glu Asp His Phe Pro Tyr
```

```
            260                 265                 270

Phe Lys His Ile Ala Lys Pro Gly Trp Lys Asn Ser Ile Arg His Asn
        275                 280                 285

Leu Ser Leu His Asp Met Phe Val Arg Glu Thr Ser Ala Asn Gly Lys
    290                 295                 300

Val Ser Phe Trp Thr Ile His Pro Ser Ala Asn Arg Tyr Leu Thr Leu
305                 310                 315                 320

Asp Gln Val Phe Lys Pro Leu Asp Pro Gly Ser Pro Gln Leu Pro Glu
                325                 330                 335

His Leu Glu Ser Gln Gln Lys Arg Pro Asn Pro Glu Leu Arg Arg Asn
            340                 345                 350

Met Thr Ile Lys Thr Glu Leu Pro Leu Gly Ala Arg Arg Lys Met Lys
        355                 360                 365

Pro Leu Leu Pro Arg Val Ser Ser Tyr Leu Val Pro Ile Gln Phe Pro
    370                 375                 380

Val Asn Gln Ser Leu Val Leu Gln Pro Ser Val Lys Val Pro Leu Pro
385                 390                 395                 400

Leu Ala Ala Ser Leu Met Ser Ser Glu Leu Ala Arg His Ser Lys Arg
                405                 410                 415

Val Arg Ile Ala Pro Lys Val Leu Leu Ala Glu Glu Gly Ile Ala Pro
            420                 425                 430

Leu Ser Ser Ala Gly Pro Gly Lys Glu Glu Lys Leu Leu Phe Gly Glu
        435                 440                 445

Gly Phe Ser Pro Leu Leu Pro Val Gln Thr Ile Lys Glu Glu Glu Ile
    450                 455                 460

Gln Pro Gly Glu Glu Met Pro His Leu Ala Arg Pro Ile Lys Val Glu
465                 470                 475                 480

Ser Pro Pro Leu Glu Glu Trp Pro Ser Pro Ala Pro Ser Phe Lys Glu
                485                 490                 495

Glu Ser Ser His Ser Trp Glu Asp Ser Ser Gln Ser Pro Thr Pro Arg
            500                 505                 510

Pro Lys Lys Ser Tyr Ser Gly Leu Arg Ser Pro Thr Arg Cys Val Ser
        515                 520                 525

Glu Met Leu Val Ile Gln His Arg Glu Arg Arg Glu Arg Ser Arg Ser
    530                 535                 540

Arg Arg Lys Gln His Leu Leu Pro Pro Cys Val Asp Glu Pro Glu Leu
545                 550                 555                 560

Leu Phe Ser Glu Gly Pro Ser Thr Ser Arg Trp Ala Ala Glu Leu Pro
                565                 570                 575

Phe Pro Ala Asp Ser Ser Asp Pro Ala Ser Gln Leu Ser Tyr Ser Gln
            580                 585                 590

Glu Val Gly Gly Pro Phe Lys Thr Pro Ile Lys Glu Thr Leu Pro Ile
        595                 600                 605

Ser Ser Thr Pro Ser Lys Ser Val Leu Pro Arg Thr Pro Glu Ser Trp
    610                 615                 620

Arg Leu Thr Pro Pro Ala Lys Val Gly Gly Leu Asp Phe Ser Pro Val
625                 630                 635                 640

Gln Thr Ser Gln Gly Ala Ser Asp Pro Leu Pro Asp Pro Leu Gly Leu
                645                 650                 655

Met Asp Leu Ser Thr Thr Pro Leu Gln Ser Ala Pro Pro Leu Glu Ser
            660                 665                 670

Pro Gln Arg Leu Leu Ser Ser Glu Pro Leu Asp Leu Ile Ser Val Pro
        675                 680                 685
```

Phe Gly Asn Ser Ser Pro Ser Asp Ile Asp Val Pro Lys Pro Gly Ser
690 695 700

Pro Glu Pro Gln Val Ser Gly Leu Ala Ala Asn Arg Ser Leu Thr Glu
705 710 715 720

Gly Leu Val Leu Asp Thr Met Asn Asp Ser Leu Ser Lys Ile Leu Leu
725 730 735

Asp Ile Ser Phe Pro Gly Leu Asp Glu Asp Pro Leu Gly Pro Asp Asn
740 745 750

Ile Asn Trp Ser Gln Phe Ile Pro Glu Leu Gln
755 760

<210> SEQ ID NO 74
<211> LENGTH: 3665
<212> TYPE: DNA
<213> ORGANISM: Homo sapiens
<220> FEATURE:
<221> NAME/KEY: CDS
<222> LOCATION: (284)..(2689)

<400> SEQUENCE: 74
tttcaaacag cggaacaaac tgaaagctcc ggtgccagac cccacccccg gccccggccc 60 gggacccccct cccctcccgg gatcccccgg ggttcccacc ccgcccgcac cgccggggac 120
ccggccggtc cggcgcgagc ccccgtccgg ggccctggct cggcccccag gttggaggag 180
cccggagccc gccttcggag ctacggccta acggcggcgg cgactgcagt ctggagggtc 240
cacacttgtg attctcaatg gagagtgaaa acgcagattc ata atg aaa act agc 295
Met Lys Thr Ser
1 ccc cgt cgg cca ctg att ctc aaa aga cgg agg ctg ccc ctt cct gtt 343
Pro Arg Arg Pro Leu Ile Leu Lys Arg Arg Arg Leu Pro Leu Pro Val
5 10 15 20 caa aat gcc cca agt gaa aca tca gag gag gaa cct aag aga tcc cct 391
Gln Asn Ala Pro Ser Glu Thr Ser Glu Glu Glu Pro Lys Arg Ser Pro
25 30 35 gcc caa cag gag tct aat caa gca gag gcc tcc aag gaa gtg gca gag 439
Ala Gln Gln Glu Ser Asn Gln Ala Glu Ala Ser Lys Glu Val Ala Glu
40 45 50 tcc aac tct tgc aag ttt cca gct ggg atc aag att att aac cac ccc 487
Ser Asn Ser Cys Lys Phe Pro Ala Gly Ile Lys Ile Ile Asn His Pro
55 60 65 acc atg ccc aac acg caa gta gtg gcc atc ccc aac aat gct aat att 535
Thr Met Pro Asn Thr Gln Val Val Ala Ile Pro Asn Asn Ala Asn Ile
70 75 80 cac agc atc atc aca gca ctg act gcc aag gga aaa gag agt ggc agt 583
His Ser Ile Ile Thr Ala Leu Thr Ala Lys Gly Lys Glu Ser Gly Ser
85 90 95 100 agt ggg ccc aac aaa ttc atc ctc atc agc tgt ggg gga gcc cca act 631
Ser Gly Pro Asn Lys Phe Ile Leu Ile Ser Cys Gly Gly Ala Pro Thr
105 110 115 cag cct cca gga ctc cgg cct caa acc caa acc agc tat gat gcc aaa 679
Gln Pro Pro Gly Leu Arg Pro Gln Thr Gln Thr Ser Tyr Asp Ala Lys
120 125 130 agg aca gaa gtg acc ctg gag acc ttg gga cca aaa cct gca gct agg 727
Arg Thr Glu Val Thr Leu Glu Thr Leu Gly Pro Lys Pro Ala Ala Arg
135 140 145 gat gtg aat ctt cct aga cca cct gga gcc ctt tgc gag cag aaa cgg 775
Asp Val Asn Leu Pro Arg Pro Pro Gly Ala Leu Cys Glu Gln Lys Arg
150 155 160

```
gag acc tgt gca gat ggt gag gca gca ggc tgc act atc aac aat agc      823
Glu Thr Cys Ala Asp Gly Glu Ala Ala Gly Cys Thr Ile Asn Asn Ser
165                 170                 175                 180

cta tcc aac atc cag tgg ctt cga aag atg agt tct gat gga ctg ggc      871
Leu Ser Asn Ile Gln Trp Leu Arg Lys Met Ser Ser Asp Gly Leu Gly
                185                 190                 195

tcc cgc agc atc aag caa gag atg gag gaa aag gag aat tgt cac ctg      919
Ser Arg Ser Ile Lys Gln Glu Met Glu Glu Lys Glu Asn Cys His Leu
            200                 205                 210

gag cag cga cag gtt aag gtt gag gag cct tcg aga cca tca gcg tcc      967
Glu Gln Arg Gln Val Lys Val Glu Glu Pro Ser Arg Pro Ser Ala Ser
        215                 220                 225

tgg cag aac tct gtg tct gag cgg cca ccc tac tct tac atg gcc atg     1015
Trp Gln Asn Ser Val Ser Glu Arg Pro Pro Tyr Ser Tyr Met Ala Met
    230                 235                 240

ata caa ttc gcc atc aac agc act gag agg aag cgc atg act ttg aaa     1063
Ile Gln Phe Ala Ile Asn Ser Thr Glu Arg Lys Arg Met Thr Leu Lys
245                 250                 255                 260

gac atc tat acg tgg att gag gac cac ttt ccc tac ttt aag cac att     1111
Asp Ile Tyr Thr Trp Ile Glu Asp His Phe Pro Tyr Phe Lys His Ile
                265                 270                 275

gcc aag cca ggc tgg aag aac tcc atc cgc cac aac ctt tcc ctg cac     1159
Ala Lys Pro Gly Trp Lys Asn Ser Ile Arg His Asn Leu Ser Leu His
            280                 285                 290

gac atg ttt gtc cgg gag acg tct gcc aat ggc aag gtc tcc ttc tgg     1207
Asp Met Phe Val Arg Glu Thr Ser Ala Asn Gly Lys Val Ser Phe Trp
        295                 300                 305

acc att cac ccc agt gcc aac cgc tac ttg aca ttg gac cag gtg ttt     1255
Thr Ile His Pro Ser Ala Asn Arg Tyr Leu Thr Leu Asp Gln Val Phe
    310                 315                 320

aag cca ctg gac cca ggg tct cca caa ttg ccc gag cac ttg gaa tca     1303
Lys Pro Leu Asp Pro Gly Ser Pro Gln Leu Pro Glu His Leu Glu Ser
325                 330                 335                 340

cag cag aaa cga ccg aat cca gag ctc cgc cgg aac atg acc atc aaa     1351
Gln Gln Lys Arg Pro Asn Pro Glu Leu Arg Arg Asn Met Thr Ile Lys
                345                 350                 355

acc gaa ctc ccc ctg ggc gca cgg cgg aag atg aag cca ctg cta cca     1399
Thr Glu Leu Pro Leu Gly Ala Arg Arg Lys Met Lys Pro Leu Leu Pro
            360                 365                 370

cgg gtc agc tca tac ctg gta cct atc cag ttc ccg gtg aac cag tca     1447
Arg Val Ser Ser Tyr Leu Val Pro Ile Gln Phe Pro Val Asn Gln Ser
        375                 380                 385

ctg gtg ttg cag ccc tcg gtg aag gtg cca ttg ccc ctg gcg gct tcc     1495
Leu Val Leu Gln Pro Ser Val Lys Val Pro Leu Pro Leu Ala Ala Ser
    390                 395                 400

ctc atg agc tca gag ctt gcc cgc cat agc aag cga gtc cgc att gcc     1543
Leu Met Ser Ser Glu Leu Ala Arg His Ser Lys Arg Val Arg Ile Ala
405                 410                 415                 420

ccc aag gtt ttt ggg gaa cag gtg gtg ttt ggt tac atg agt aag ttc     1591
Pro Lys Val Phe Gly Glu Gln Val Val Phe Gly Tyr Met Ser Lys Phe
                425                 430                 435

ttt agt ggc gat ctg cga gat ttt ggt aca ccc atc acc agc ttg ttt     1639
Phe Ser Gly Asp Leu Arg Asp Phe Gly Thr Pro Ile Thr Ser Leu Phe
            440                 445                 450

aat ttt atc ttt ctt tgt tta tca gtg ctg cta gct gag gag ggg ata     1687
Asn Phe Ile Phe Leu Cys Leu Ser Val Leu Leu Ala Glu Glu Gly Ile
        455                 460                 465

gct cct ctt tct tct gca gga cca ggg aaa gag gag aaa ctc ctg ttt     1735
Ala Pro Leu Ser Ser Ala Gly Pro Gly Lys Glu Glu Lys Leu Leu Phe
    470                 475                 480
```

```
gga gaa ggg ttt tct cct ttg ctt cca gtt cag act atc aag gag gaa      1783
Gly Glu Gly Phe Ser Pro Leu Leu Pro Val Gln Thr Ile Lys Glu Glu
485                 490                 495                 500

gaa atc cag cct ggg gag gaa atg cca cac tta gcg aga ccc atc aaa      1831
Glu Ile Gln Pro Gly Glu Glu Met Pro His Leu Ala Arg Pro Ile Lys
                505                 510                 515

gtg gag agc cct ccc ttg gaa gag tgg ccc tcc ccg gcc cca tct ttc      1879
Val Glu Ser Pro Pro Leu Glu Glu Trp Pro Ser Pro Ala Pro Ser Phe
            520                 525                 530

aaa gag gaa tca tct cac tcc tgg gag gat tcg tcc caa tct ccc acc      1927
Lys Glu Glu Ser Ser His Ser Trp Glu Asp Ser Ser Gln Ser Pro Thr
        535                 540                 545

cca aga ccc aag aag tcc tac agt ggg ctt agg tcc cca acc cgg tgt      1975
Pro Arg Pro Lys Lys Ser Tyr Ser Gly Leu Arg Ser Pro Thr Arg Cys
    550                 555                 560

gtc tcg gaa atg ctt gtg att caa cac agg gag agg agg gag agg agc      2023
Val Ser Glu Met Leu Val Ile Gln His Arg Glu Arg Arg Glu Arg Ser
565                 570                 575                 580

cgg tct cgg agg aaa cag cat cta ctg cct ccc tgt gtg gat gag ccg      2071
Arg Ser Arg Arg Lys Gln His Leu Leu Pro Pro Cys Val Asp Glu Pro
                585                 590                 595

gag ctg ctc ttc tca gag ggg ccc agt act tcc cgc tgg gcc gca gag      2119
Glu Leu Leu Phe Ser Glu Gly Pro Ser Thr Ser Arg Trp Ala Ala Glu
            600                 605                 610

ctc ccg ttc cca gca gac tcc tct gac cct gcc tcc cag ctc agc tac      2167
Leu Pro Phe Pro Ala Asp Ser Ser Asp Pro Ala Ser Gln Leu Ser Tyr
        615                 620                 625

tcc cag gaa gtg gga gga cct ttt aag aca ccc att aag gaa acg ctg      2215
Ser Gln Glu Val Gly Gly Pro Phe Lys Thr Pro Ile Lys Glu Thr Leu
    630                 635                 640

ccc atc tcc tcc acc ccg agc aaa tct gtc ctc ccc aga acc cct gaa      2263
Pro Ile Ser Ser Thr Pro Ser Lys Ser Val Leu Pro Arg Thr Pro Glu
645                 650                 655                 660

tcc tgg agg ctc acg ccc cca gcc aaa gta ggg gga ctg gat ttc agc      2311
Ser Trp Arg Leu Thr Pro Pro Ala Lys Val Gly Gly Leu Asp Phe Ser
                665                 670                 675

cca gta caa acc tcc cag ggt gcc tct gac ccc ttg cct gac ccc ctg      2359
Pro Val Gln Thr Ser Gln Gly Ala Ser Asp Pro Leu Pro Asp Pro Leu
            680                 685                 690

ggg ctg atg gat ctc agc acc act ccc ttg caa agt gct ccc ccc ctt      2407
Gly Leu Met Asp Leu Ser Thr Thr Pro Leu Gln Ser Ala Pro Pro Leu
        695                 700                 705

gaa tca ccg caa agg ctc ctc agt tca gaa ccc tta gac ctc atc tcc      2455
Glu Ser Pro Gln Arg Leu Leu Ser Ser Glu Pro Leu Asp Leu Ile Ser
    710                 715                 720

gtc ccc ttt ggc aac tct tct ccc tca gat ata gac gtc ccc aag cca      2503
Val Pro Phe Gly Asn Ser Ser Pro Ser Asp Ile Asp Val Pro Lys Pro
725                 730                 735                 740

ggc tcc ccg gag cca cag gtt tct ggc ctt gca gcc aat cgt tct ctg      2551
Gly Ser Pro Glu Pro Gln Val Ser Gly Leu Ala Ala Asn Arg Ser Leu
                745                 750                 755

aca gaa ggc ctg gtc ctg gac aca atg aat gac agc ctc agc aag atc      2599
Thr Glu Gly Leu Val Leu Asp Thr Met Asn Asp Ser Leu Ser Lys Ile
            760                 765                 770

ctg ctg gac atc agc ttt cct ggc ctg gac gag gac cca ctg ggc cct      2647
Leu Leu Asp Ile Ser Phe Pro Gly Leu Asp Glu Asp Pro Leu Gly Pro
        775                 780                 785

gac aac atc aac tgg tcc cag ttt att cct gag cta cag tag              2689
Asp Asn Ile Asn Trp Ser Gln Phe Ile Pro Glu Leu Gln
```

```
    790                 795                 800

agccctgccc ttgcccctgt gctcaagctg tccaccatcc cgggcactcc aaggctcagt   2749

gcaccccaag cctctgagtg aggacagcag gcagggactg ttctgctcct catagctccc   2809

tgctgcctga ttatgcaaaa gtagcagtca caccctagcc actgctggga ccttgtgttc   2869

cccaagagta tctgattcct ctgctgtccc tgccaggagc tgaagggtgg gaacaacaaa   2929

ggcaatggtg aaaagagatt aggaaccccc cagcctgttt ccattctctg cccagcagtc   2989

tcttaccttc cctgatcttt gcagggtggt ccgtgtaaat agtataaatt ctccaaatta   3049

tcctctaatt ataaatgtaa gcttatttcc ttagatcatt atccagagac tgccagaagg   3109

tgggtaggat gacctggggt ttcaattgac ttctgttcct tgcttttagt tttgatagaa   3169

gggaagacct gcagtgcacg gtttcttcca ggctgaggta cctggatctt gggttcttca   3229

ctgcagggac ccagacaagt ggatctgctt gccagagtcc tttttgcccc tccctgccac   3289

ctccccgtgt ttccaagtca gctttcctgc aagaagaaat cctggttaaa aaagtctttt   3349

gtattgggtc aggagttgaa tttggggtgg gaggatggat gcaactgaag cagagtgtgg   3409

gtgcccagat gtgcgctatt agatgtttct ctgataatgt ccccaatcat accagggaga   3469

ctggcattga cgagaactca ggtggaggct tgagaaggcc gaaagggccc ctgacctgcc   3529

tggcttcctt agcttgcccc tcagctttgc aaagagccac cctaggcccc agctgaccgc   3589

atgggtgtga gccagcttga gaacactaac tactcaataa aagcgaaggt ggacatgaaa   3649

aaaaaaaaaa aaaaaa                                                    3665


<210> SEQ ID NO 75
<211> LENGTH: 801
<212> TYPE: PRT
<213> ORGANISM: Homo sapiens

<400> SEQUENCE: 75

Met Lys Thr Ser Pro Arg Arg Pro Leu Ile Leu Lys Arg Arg Arg Leu
1               5                   10                  15

Pro Leu Pro Val Gln Asn Ala Pro Ser Glu Thr Ser Glu Glu Glu Pro
            20                  25                  30

Lys Arg Ser Pro Ala Gln Gln Glu Ser Asn Gln Ala Glu Ala Ser Lys
        35                  40                  45

Glu Val Ala Glu Ser Asn Ser Cys Lys Phe Pro Ala Gly Ile Lys Ile
    50                  55                  60

Ile Asn His Pro Thr Met Pro Asn Thr Gln Val Val Ala Ile Pro Asn
65                  70                  75                  80

Asn Ala Asn Ile His Ser Ile Ile Thr Ala Leu Thr Ala Lys Gly Lys
                85                  90                  95

Glu Ser Gly Ser Ser Gly Pro Asn Lys Phe Ile Leu Ile Ser Cys Gly
            100                 105                 110

Gly Ala Pro Thr Gln Pro Pro Gly Leu Arg Pro Gln Thr Gln Thr Ser
        115                 120                 125

Tyr Asp Ala Lys Arg Thr Glu Val Thr Leu Glu Thr Leu Gly Pro Lys
    130                 135                 140

Pro Ala Ala Arg Asp Val Asn Leu Pro Arg Pro Pro Gly Ala Leu Cys
145                 150                 155                 160

Glu Gln Lys Arg Glu Thr Cys Ala Asp Gly Glu Ala Ala Gly Cys Thr
                165                 170                 175

Ile Asn Asn Ser Leu Ser Asn Ile Gln Trp Leu Arg Lys Met Ser Ser
            180                 185                 190
```

```
Asp Gly Leu Gly Ser Arg Ser Ile Lys Gln Glu Met Glu Glu Lys Glu
        195                 200                 205

Asn Cys His Leu Glu Gln Arg Gln Val Lys Val Glu Glu Pro Ser Arg
    210                 215                 220

Pro Ser Ala Ser Trp Gln Asn Ser Val Ser Glu Arg Pro Pro Tyr Ser
225                 230                 235                 240

Tyr Met Ala Met Ile Gln Phe Ala Ile Asn Ser Thr Glu Arg Lys Arg
                245                 250                 255

Met Thr Leu Lys Asp Ile Tyr Thr Trp Ile Glu Asp His Phe Pro Tyr
            260                 265                 270

Phe Lys His Ile Ala Lys Pro Gly Trp Lys Asn Ser Ile Arg His Asn
        275                 280                 285

Leu Ser Leu His Asp Met Phe Val Arg Glu Thr Ser Ala Asn Gly Lys
    290                 295                 300

Val Ser Phe Trp Thr Ile His Pro Ser Ala Asn Arg Tyr Leu Thr Leu
305                 310                 315                 320

Asp Gln Val Phe Lys Pro Leu Asp Pro Gly Ser Pro Gln Leu Pro Glu
                325                 330                 335

His Leu Glu Ser Gln Gln Lys Arg Pro Asn Pro Glu Leu Arg Arg Asn
            340                 345                 350

Met Thr Ile Lys Thr Glu Leu Pro Leu Gly Ala Arg Arg Lys Met Lys
        355                 360                 365

Pro Leu Leu Pro Arg Val Ser Ser Tyr Leu Val Pro Ile Gln Phe Pro
    370                 375                 380

Val Asn Gln Ser Leu Val Leu Gln Pro Ser Val Lys Val Pro Leu Pro
385                 390                 395                 400

Leu Ala Ala Ser Leu Met Ser Ser Glu Leu Ala Arg His Ser Lys Arg
                405                 410                 415

Val Arg Ile Ala Pro Lys Val Phe Gly Glu Gln Val Val Phe Gly Tyr
            420                 425                 430

Met Ser Lys Phe Phe Ser Gly Asp Leu Arg Asp Phe Gly Thr Pro Ile
        435                 440                 445

Thr Ser Leu Phe Asn Phe Ile Phe Leu Cys Leu Ser Val Leu Leu Ala
    450                 455                 460

Glu Glu Gly Ile Ala Pro Leu Ser Ser Ala Gly Pro Gly Lys Glu Glu
465                 470                 475                 480

Lys Leu Leu Phe Gly Glu Gly Phe Ser Pro Leu Leu Pro Val Gln Thr
                485                 490                 495

Ile Lys Glu Glu Glu Ile Gln Pro Gly Glu Glu Met Pro His Leu Ala
            500                 505                 510

Arg Pro Ile Lys Val Glu Ser Pro Pro Leu Glu Glu Trp Pro Ser Pro
        515                 520                 525

Ala Pro Ser Phe Lys Glu Glu Ser Ser His Ser Trp Glu Asp Ser Ser
    530                 535                 540

Gln Ser Pro Thr Pro Arg Pro Lys Lys Ser Tyr Ser Gly Leu Arg Ser
545                 550                 555                 560

Pro Thr Arg Cys Val Ser Glu Met Leu Val Ile Gln His Arg Glu Arg
                565                 570                 575

Arg Glu Arg Ser Arg Ser Arg Arg Lys Gln His Leu Leu Pro Pro Cys
            580                 585                 590

Val Asp Glu Pro Glu Leu Leu Phe Ser Glu Gly Pro Ser Thr Ser Arg
        595                 600                 605
```

```
Trp Ala Ala Glu Leu Pro Phe Pro Ala Asp Ser Ser Asp Pro Ala Ser
    610                 615                 620

Gln Leu Ser Tyr Ser Gln Glu Val Gly Gly Pro Phe Lys Thr Pro Ile
625                 630                 635                 640

Lys Glu Thr Leu Pro Ile Ser Ser Thr Pro Ser Lys Ser Val Leu Pro
                645                 650                 655

Arg Thr Pro Glu Ser Trp Arg Leu Thr Pro Pro Ala Lys Val Gly Gly
            660                 665                 670

Leu Asp Phe Ser Pro Val Gln Thr Ser Gln Gly Ala Ser Asp Pro Leu
        675                 680                 685

Pro Asp Pro Leu Gly Leu Met Asp Leu Ser Thr Thr Pro Leu Gln Ser
    690                 695                 700

Ala Pro Pro Leu Glu Ser Pro Gln Arg Leu Leu Ser Ser Glu Pro Leu
705                 710                 715                 720

Asp Leu Ile Ser Val Pro Phe Gly Asn Ser Ser Pro Ser Asp Ile Asp
                725                 730                 735

Val Pro Lys Pro Gly Ser Pro Glu Pro Gln Val Ser Gly Leu Ala Ala
            740                 745                 750

Asn Arg Ser Leu Thr Glu Gly Leu Val Leu Asp Thr Met Asn Asp Ser
        755                 760                 765

Leu Ser Lys Ile Leu Leu Asp Ile Ser Phe Pro Gly Leu Asp Glu Asp
    770                 775                 780

Pro Leu Gly Pro Asp Asn Ile Asn Trp Ser Gln Phe Ile Pro Glu Leu
785                 790                 795                 800

Gln


<210> SEQ ID NO 76
<211> LENGTH: 4
<212> TYPE: PRT
<213> ORGANISM: Artificial Sequence
<220> FEATURE:
<223> OTHER INFORMATION: a linker peptide

<400> SEQUENCE: 76

Asn Lys Arg Lys
1
```